(12) United States Patent
Baker et al.

(10) Patent No.: US 6,632,836 B1
(45) Date of Patent: Oct. 14, 2003

(54) CARBOCYCLIC POTASSIUM CHANNEL INHIBITORS

(75) Inventors: Robert K. Baker, Cranford, NJ (US); Jianming Bao, Scotch Plains, NJ (US); Jennifer Chee, Princeton, NJ (US); Maria L. Garcia, Edison, NJ (US); Gregory J. Kaczorowski, Edison, NJ (US); Frank Kayser, Hoboken, NJ (US); Andrew Kotliar, Highland Park, NJ (US); Chou Juitsai Liu, Fanwood, NJ (US); Shouwu Miao, Edison, NJ (US); William H. Parsons, Belle Mead, NJ (US); Kathleen M. Rupprecht, Cranford, NJ (US); William A. Schmalhofer, South Plainfield, NJ (US); Christopher F. Claiborne, Lansdale, PA (US); David A. Claremon, Maple Glen, PA (US); Nigel Liverton, Harleysville, PA (US); Wayne J. Thompson, Lansdale, PA (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 09/422,143

(22) Filed: Oct. 21, 1999

Related U.S. Application Data

(60) Provisional application No. 60/106,416, filed on Oct. 30, 1998.

(51) Int. Cl.[7] .................. A61K 31/16; A61K 31/24; A01N 37/18; A01N 37/12; A01N 37/44
(52) U.S. Cl. .................. 514/539; 514/563; 514/616; 514/622; 560/42; 562/451; 564/158; 564/176
(58) Field of Search .................. 564/123, 32, 57, 564/86, 155, 177, 158, 176; 548/530, 215; 549/330, 434; 558/272, 431, 245; 560/157, 158, 24, 42; 514/539, 563, 616, 622; 562/451

(56) References Cited

U.S. PATENT DOCUMENTS 5,618,938 A  4/1997  Emonds-Alt et al.

FOREIGN PATENT DOCUMENTS

| EP | 0 284 174 A1 | 9/1988 |
| EP | 0 286 278 A1 | 10/1988 |
| EP | 0 317 321 A2 | 5/1989 |
| EP | 0 471 493 A1 | 2/1992 |
| EP | 0 472 053 A2 | 2/1992 |
| WO | 96/21640 | 7/1996 |
| WO | 98/04135 | 2/1998 |
| WO | 98/04521 | 2/1998 |

OTHER PUBLICATIONS

Database CAPLUS on STN, Acc. No. 1989:192811, Bruneau et al., 'Preparation of 1,2-dihiydro-3H-indazol-3-ones as lipoxygenase inhibitors.' EP 284174 (abstract).*
Database CAPLUS on STN, Acc. No. 1975:139935, Markaryan et al., Arm. Khim. Zh. (1974), 27(9), p. 779–84 (abstract).*
Ott, et al., J. Med. Chem., vol. 11, pp. 777–787, 1968.
Dupin, C., et al., Bull. Soc. Chim. Fr., 1964, pp. 1993–2000.
Dupin, C., et al., Chemical Abstracts Plus, 1965, 62:461c–h, 462a–d (cumulative with Dupin et al above).
Mndzhoyan, A.L. et al.: Chem. Heterocycl. Compd. (Engl. Transl.), vol. 5, 1969, pp. 395–397.
Mndzhoyan, A.L. et al.: Chem. Heterocycl. Compd. (Engl. Transl.), vol. 7, 1971, pp. 596–599.
Shirai, H.; Yashiro, T.; Aoyama, T.: Chem. Pharm. Bull., vol. 20, No. 1, 1972, pp. 41–46.
Markaryan, et al., Arm. Khim. Zh., vol. 27, No. 9, pp. 779–784 (1974).
Purchase, T.S. et al., Bioorganic & Medicinal Chemistry, vol. 5, No. 4, pp. 739–747 (1997).
Avetisyan, et al., Arm. Khim, Zh., vol. 34(12), pp. 1007–1010, 1981 (attached English Abstract).

* cited by examiner

Primary Examiner—Brian Davis
(74) Attorney, Agent, or Firm—J. Antonio Garcia-Rivas; Valerie J. Camara; Richard S. Parr

(57) ABSTRACT

The present invention relates to a class of carbocyclic compounds of Formula I that are useful as potassium channel inhibitors to treat autoimmune disorders, cardiac arrhythmias, and the like.

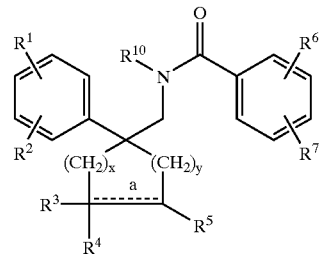

23 Claims, No Drawings

CARBOCYCLIC POTASSIUM CHANNEL INHIBITORS

This application claims benefit from provisional application No. 60/106,416 filed Oct. 30, 1998.

BACKGROUND OF THE INVENTION

The present invention relates to a class of carbocyclic compounds that are useful as potassium channel inhibitors to treat autoimmune disorders, cardiac arrhythmias and the like.

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma.

Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates. Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A (CsA), which was approved by the US FDA in 1983 is currently the leading drug used to prevent rejection of transplanted organs. In 1993, FK-506 (Prograf) was approved by the US FDA for the prevention of rejection in liver transplantation. CsA and FK-506 act by inhibiting the body's immune system from mobilizing its vast arsenal of natural protecting agents to reject the transplant's foreign protein. In 1994, CsA was approved by the US FDA for the treatment of severe psoriasis and has been approved by European regulatory agencies for the treatment of atopic dermatitis. Though they are effective in fighting transplant rejection, CsA and FK-506 are known to cause several undesirable side effects including nephrotoxicity, neurotoxicity, and gastrointestinal discomfort. Therefore, a selective immunossuppressant without these side effects still remains to be developed. Potassium channel inhibitors promise to be the solution to this problem.

The importance of potassium channels was first recognized almost fifty years ago when Hodgkin and Huxley discovered that potassium ions contributed to the current that excited the squid giant axon. Research in the area, however, was hampered by the lack of selective, high affinity ligands for potassium channels. But the advent of recombinant DNA techniques and single cell and whole cell voltage clamp techniques has changed the slow pace of the field. Potassium channels have turned out to be the most diverse family of ion channels discovered to date. They modulate a number of cellular events such as muscle contraction, neuro-endocrine secretion, frequency and duration of action potentials, electrolyte homeostasis, and resting membrane potential.

Potassium channels have been classified according to their biophysical and pharmacological characteristics. Salient among these are the voltage dependent potassium channels, such as $K_v1$. The $K_v1$ class of potassium channels is further subdivided depending on the molecular sequence of the channel, for example $K_v1.1$, $K_v1.3$, $K_v1.5$. Functional voltage-gated $K^+$ channels can exist as multimeric structures formed by the association of either identical or dissimilar subunits. This phenomena is thought to account for the wide diversity of $K^+$ channels. However, subunit compositions of native $K^+$ channels and the physiologic role that particular channels play are, in most cases, still unclear.

Membrane depolarization by $K_v1.3$ inhibition has been shown to be an effective method to prevent T-cell proliferation and therefore has applications in many autoimmune conditions. Inhibition of $K^+$ channels in the plasma membrane of human T-lymphocytes has been postulated to play a role in eliciting immunosuppressive responses by regulating intracellular $Ca^{++}$ homeostasis, which has been found to be important in T-cell activation.

The $K_v1.3$ voltage-gated potassium channel is found in neurons, blood cells, osteoclasts and T-lymphocytes. The Chandy and Cahalan laboratories proposed a hypothesis that blocking the $K_v1.3$ channel would elicit an immunosuppressant response. (Chandy et al., *J. Exp. Med.* 160, 369, 1984; Decoursey et al., Nature, 307, 465, 1984). However, the K+ channel blockers employed in their studies were nonselective. Until research with the peptide margatoxin, a peptide found in scorpion venom, no specific inhibitor of the $K_v1.3$ channel existed to test this hypothesis. Although a laboratory (Price et al., *Proc. Natl. Acad. Sci. USA*, 86, 10171, 1989) showed that charybdotoxin would block $K_v1.3$ in human T cells, charybdotoxin was subsequently shown to inhibit four different $K^+$ channels ($K_v1.3$ and three distinct small conductance $Ca^{++}$ activated $K^+$ channels) in human T-lymphocytes, limiting the use of this toxin as a probe for the physiological role of $K_v1.3$ (Leonard et al., *Proc. Natl. Acad. Sci. USA*, 89, 10094, 1992). Margatoxin, on the other hand, blocks only $K_v1.3$ in T-cells, and has immunosuppressant activity in both in vitro and in vivo models. (Lin et al., *J. Exp. Med*, 177, 637, 1993). The therapeutic utility of this compound, however, is limited by its potent toxicity. Recently, a class of compounds has been reported that may be an attractive alternative to the above-mentioned drugs, see for example U.S. Pat. Nos. 5,670,504; 5,631,282; 5,696,156; 5,679,705; and 5,696,156. While addressing some of the activity/toxicity problems of previous drugs, these compounds tend to be of large molecular weight and are generally produced by synthetic manipulation of a natural product, isolation of which is cumbersome and labor intensive.

Atrial fibrillation (AF) is the most common sustained cardiac arrhythmia in clinical practice and is likely to increase in prevalence with the aging of the population. Currently, AF affects more than 1 million Americans annually, represents over 5% of all admissions for cardiovascular diseases and causes more than 80,000 strokes each year in the United States. While AF is rarely a lethal arrhythmia, it is responsible for substantial morbidity and can lead to complications such as the development of congestive heart failure or thromboembolism. Currently available Class I and Class III antiarrhythmic drugs reduce the rate of recurrence of AF, but are of limited use because of a variety of potentially adverse effects including ventricular proarrhythmia. Because current therapy is inadequate and fraught with side effects, there is a clear need to develop new therapeutic approaches.

Antiarrhythmic agents of Class III are drugs that cause a selective prolongation of the duration of the action potential without significant cardiac depression. Available drugs in this class are limited in number. Examples such as sotalol and amiodarone have been shown to possess interesting Class III properties (Singh B. N., Vaughan Williams E. M. "A Third Class Of Anti-Arrhythmic Action: Effects On Atrial And Ventricular Intracellular Potentials And Other Pharmacological Actions On Cardiac Muscle, of MJ 1999 and AH 3747" Br. *J. Pharmacol* 1970; 39:675–689. and Singh B. N., Vaughan Williams E. M, "The Effect Of Amiodarone, A New Anti-Anginal Drug, On Cardiac Muscle", Br *J. Pharmacol* 1970; 39:657–667.), but these are not selective Class III agents. Sotalol also possesses Class II effects which may cause cardiac depression and is contraindicated in certain susceptible patients. Amiodarone, also is not a selective Class III antiarrhythmic agent because it possesses multiple electrophysiological actions and is severely limited by side effects (Nademanee, K. "The Amiodarone Odessey". *J. Am. Coll. Cardiol.* 1992; 20:1063–1065.) Drugs of this class are expected to be effective in preventing ventricular fibrillation. Selective class III agents, by definition, are not considered to cause myocardial depression or an induction of arrhythmias due to inhibition of conduction of the action potential as seen with Class I antiarrhythmic agents.

Class III agents increase myocardial refractoriness via a prolongation of cardiac action potential duration. Theoretically, prolongation of the cardiac action potential can be achieved by enhancing inward currents (i.e. Na$^+$ or Ca$^{2+}$ currents; hereinafter I$_{Na}$ and I$_{Ca}$, respectively) or by reducing outward repolarizing potassium (K$^+$) currents. The delayed rectifier (I$_K$) K$^+$ current is the main outward current involved in the overall repolarization process during the action potential plateau, whereas the transient outward (I$_{to}$) and inward rectifier (I$_{K1}$) K$^+$ currents are responsible for the rapid initial and terminal phases of repolarization, respectively. Cellular electrophysiologic studies have demonstrated that I$_K$ consists of two pharmacologically and kinetically distinct K$^+$ current subtypes, I$_{Kr}$ (rapidly activating and deactivating) and I$_{Ks}$ (slowly activating and deactivating) (Sanguinetti and Jurkiewicz, Two Components Of Cardiac Delayed Rectifier K+ Current: Differential Sensitivity To Block By Class III Antiarrhythmic Agents, *J Gen Physiol* 1990, 96:195–215). Class III antiarrhythmic agents currently in development, including d-sotalol, dofetilide (UK-68,798), almokalant (H234/09), E-4031 and methanesulfonamide-N-[1'-6-cyano-1,2,3,4-tetrahydro-2-naphthalenyl)-3,4-dihydro-4-hydroxyspiro[2H-1-benzopyran-2,4'-piperidin]-6yl]monochloride, predominantly, if not exclusively, block I$_{Kr}$. Although, amiodarone is a blocker of I$_{Ks}$ (Balser J. R. Bennett, P. B., Hondeghem, L. M. and Roden, D. M. "Suppression Of Time-Dependent Outward Current In Guinea Pig Ventricular Myocytes: Actions Of Quinidine And Amiodarone. *Circ. Res.* 1991, 69:519–529), it also blocks I$_{Na}$ and I$_{Ca}$, effects thyroid function, is as a nonspecific adrenergic blocker, and acts as an inhibitor of the enzyme phospholipase (Nademanee, K. "The Amiodarone Odessey". *J. Am. Coll. Cardiol.* 1992; 20:1063–1065). Therefore, its method of treating arrhythmia is uncertain Most Class III agents that are known to be in development predominantly block I$_{Kr}$.

Reentrant excitation (reentry) has been shown to be a prominent mechanism underlying supraventricular arrhythmias in man. Reentrant excitation requires a critical balance between slow conduction velocity and sufficiently brief refractory periods to allow for the initiation and maintenance of multiple reentry circuits to coexist simultaneously and sustain AF. Increasing myocardial refractoriness by prolonging action potential duration (APD), prevents and/or terminates reentrant arrhythmias. Most selective Class III antiarrhythmic agents currently in development, such as d-sotalol and dofetilide predominantly, if not exclusively, block I$_{kr}$, the rapidly activating component of I$_K$ found both in atrium and ventricle in man.

Since these I$_{kr}$ blockers increase APD and refractoriness both in atria and ventricle without affecting conduction per se, theoretically they represent potential useful agents for the treatment of arrhythmias like AF. These agents have a liability in that they have an enhanced risk of proarrhythmia at slow heart rates. For example, torsades de points has been observed when these compounds are utilized (Roden, D. M. "Current Status of Class III Antiarrhythmic Drug Therapy", *Am J. Cardiol*, 1993; 72:44B–49B). This exaggerated effect at slow heart rates has been termed "reverse frequency-dependence", and is in contrast to frequency-independent or frequency-dependent actions (Hondeghem, L. M. "Development of Class III Antiarrhythmic Agents". *J. Cadiovasc. Cardiol.* 20 (Suppl. 2): S17–S22).

The slowly activating component of the delayed rectifier (I$_{ks}$) potentially overcomes some of the limitations of I$_{kr}$ blockers associated with ventricular arrhythmias. Because of its slow activation kinetics however, the role of I$_{ks}$ in atrial repolarization may be limited due to the relatively short APD of the atrium. Consequently, although I$_{ks}$ blockers may provide distinct advantage in the case of ventricular arrhythmias, their ability to affect SVT is considered to be minimal.

The ultra-rapidly activating delayed rectifier K$^+$ current (I$_{kur}$) is believed to represent the native counterpart to a cloned potassium channel designated Kv1.5 and, while present in human atrium, it appears to be absent in human ventricle. Furthermore, because of its rapidity of activation and limited slow inactivation, I$_{kur}$ is believed to contribute significantly to repolarization in human atrium. Consequently, a specific blocker Of I$_{kur}$, that is a compound which blocks Kv1.5, would overcome the short coming of other compounds by prolonging refractoriness by retarding repolarization in the human atrium without causing the delays in ventricular reporlarization that underlie arrhythmogenic afterdepolarizations and acquired long QT syndrome observed during treatment with current Class III drugs.

In intact human atrial myocytes an ultra-rapidly activating delayed rectifier K$^+$ current I$_{kur}$ which is also known as the sustained outward current, I$_{sus}$ or I$_{so}$, has been identified and this current has properties and kinetics identical to those expressed by the human K$^+$ channel clone (hKv1.5, HK2) when isolated from human heart and stably expressed in human (HEK-293) cell lines. (Wang, Fermini and Natel, 1993, Circ Res 73:1061–1076; Fedida et al., 1993, Circ Res 73:210–216; Snyders, Tamkun and Bennet, 1993, J Gen Physiol 101:513–543) and originally cloned from rat brain (Swanson et al., 10, Neuron 4:929–939). Although various antiarrythmic agents are now available on the market, those having both satisfactory efficacy and a high margin of safety have not been obtained. For example, antiarrythmic agents of Class I according to the classification scheme of Vaughan-Williams ("Classification Of Antiarrhythmic Drugs" In: Cardiac Arrhythmias, edited by: E. Sandoe, E. Flensted-Jensen, K. Olesen; Sweden, Astra, Sodertalje, pp449–472, 1981) which cause a selective inhibition of the maximum velocity of the upstroke of the action potential (max) are inadequate for preventing ventricular fibrillation. In addition, they have problems regarding safety, namely, they cause a depression of myocardial contractility and have a tendency to induce arrhythmias due to an inhibition of impulse conduction. Beta-adrenoceptor blockers and calcium antagonists which belong to Class II and IV, respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

The method of treatment of atrial arrhythmia presented herein provides for greater safety and efficacy as well preferentially providing treatment at fast heart rates when treatment of this type is most desired.

SUMMARY OF THE INVENTION

This invention relates to carbocyclic potassium channel inhibitors of general structural Formula I.

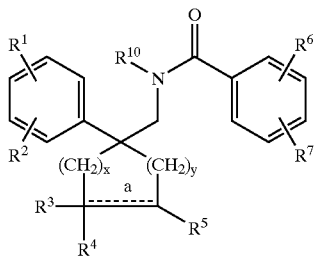

I

The compounds of this invention are useful in the treatment of autoimmune diseases, the prevention of rejection of foreign organ transplants and related afflictions, diseases and illnesses. Also within the scope of this invention are pharmaceutical formulations comprising a compound of Formula I and a pharmaceutical carrier, as well as pharmaceutical formulations comprising a compound of Formula I, one or more immunosuppressive compounds and a pharmaceutical carrier.

DETAILED DESCRIPTION OF THE INVENTION

An embodiment of the present invention is a compound of structural Formula I:

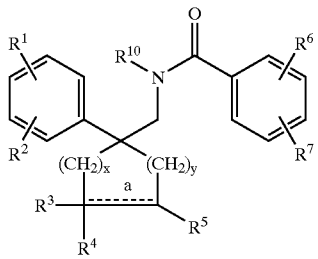

I or a pharmaceutically acceptable salt, crystal form, or hydrate, wherein a is a single bond or a double bond when $R^4$ is absent, and represented by ----- in the structure above, with the proviso that a is a single bond when x+y=0;

n is: 0, 1, 2 or 3;

r is: 0 or 1;
s is: 0 or 1;
x and y are independently 0, 1, or 2;
$R^1$, $R^2$, $R^6$ and $R^7$ are independently:
(1) halo, wherein halo is fluoro, chloro, bromo, or iodo,
(2) hydroxy,
(3) $(C_1-C_6)$-alkyl,
(4) $HO(C_1-C_6)$-alkyloxy,
(5) $(C_1-C_4)$-perfluoroalkyl,
(6) $(C_2-C_6)$-alkenyl,
(7) $(C_2-C_6)$-alkynyl,
(8) $O[(C=O)O_r]_s(C_1-C_6)$-alkyl,
(9) $(C_1-C_6)$-alkyl-$S(O)_n$—,
(10) —$(O)_r(C_0-C_6)$-alkyl-aryl, wherein aryl is phenyl or naphthyl unsubstituted or substituted with up to three substitutents selected from $(C_1-C_3)$alkyl, trifluoromethyl, and halo;
(11) —$(O)_r$-heteroaryl, wherein heteroaryl is pyridinyl or pyrryl,
(12) cyano,
(13) nitro,
(14) $CO_2H$,
(15) $CO(C_1-C_6)$-alkyl,
(16) $CO_2(C_1-C_6)$-alkyl,
(17) $CONR^8R^9$,
(18) $NR^8R^9$,
(20) $(C_2-C_6)$-alkenyloxy,
(21) (CO)-aryl, wherein aryl is phenyl, naphthyl, benzothienyl, or a benzophenone radical and is unsubstituted or substituted with up to two substitutents selected from halo, trifluromethyl, and $(C_1-C_3)$ alkyl,
(22) hydrogen,
(23) $OCF_3$,
(24) —$(CH_2)$—O—N=$C(CH_3)$(aryl), wherein aryl is phenyl or naphthyl and is unsubstituted or substituted with up to three halogen substituents,
(25) —$S(O)_n$—N $R^8R^9$, or
(26) $R^1$ and $R^2$ or $R^6$ and $R^7$ can be taken together when on adjacent carbons to form a fused benzo, dihydrofuranyl, furanyl, pyrrolidyl, dihydropyrrolidyl or 1,3-dioxolan group;

$R^3$ and $R^4$ are independently:
(1) halo, wherein halo is fluoro, chloro, bromo, or iodo,
(2) hydroxy, when a is a single bond,
(3) $HO(C_1-C_6)$-alkyloxy,
(4) $(C_1-C_4)$-perfluoroalkyl,
(5) $O(CO)CCl_3$,
(6) $(C_1-C_6)$-alkyl-$S(O)_n$—,
(7) phenyl-$(CH_2)_r$—$S(O)_n$—,
(8) cyano,
(9) nitro,
(10) $CO_2H$,
(11) $CO(C_1-C_6)$-alkyl,
(12) $CO_2(C_1-C_6)$-alkyl,
(13) $CONR^8R^9$,
(14) $NR^8R^9$,
(15) $O(CO)NR^8R^9$,
(16) azido,
(17) $NR^8(CO)NR^8R^9$,
(18) hydrogen,
(19) $(C_1-C_{10})$-alkyl, wherein alkyl includes cyclic as well as acyclic groups and is unsubstituted or substituted with one or two of the substituents selected from the group consisting of:
(a) halo, wherein halo is fluoro, chloro, bromo, or iodo, (b) hydroxy,
(c) oxo,
(d) O[(C=O)O$_r$]$_s$(C$_1$–C$_6$)-alkyl,
(e) (C$_1$–C$_6$)-alkyl-S(O)$_n$—,
(f) aryl-(C$_1$–C$_6$)-alkyloxy,
(g) cyano,
(h) nitro,
(i) vinyl,
(j) NR$^8$R$^9$,
(k) O(CO)NR$^8$R$^9$,
(l) CHO,
(m) CO$_2$H,
(n) CO(C$_1$–C$_6$)-alkyl,
(o) CO$_2$(C$_1$–C$_6$)-alkyl,
(p) CONR$^8$R$^9$,
(q) aryl, wherein aryl is defined as phenyl or naphthyl, unsubstituted or substituted with one, two or three of the substituents selected from the group consisting of:
  (a') halo, as defined above,
  (b') hydroxy,
  (c') (C$_1$–C$_6$)-alkyl,
  (d') (C1–C4)-perfluoroalkyl,
  (e') (C$_2$–C$_6$)-alkenyl,
  (f') (C$_2$–C$_6$)-alkynyl,
  (g') (C$_1$–C$_6$)-alkyloxy,
  (h') (C$_1$–C$_6$)-alkyl-S(O)$_n$—,
  (i') phenyl,
  (j') phenoxy,
  (k') cyano,
  (l') nitro,
  (m') CO$_2$H,
  (n') CO(C$_1$–C$_6$)-alkyl,
  (o') CO$_2$(C$_1$–C$_6$)-alkyl,
  (p') CONR$^8$R$^9$, and
  (q') NR$^8$R$^9$,
(r) heteroaryl, wherein heteroaryl is defined as an unsubstituted, monosubstituted, or disubstituted five or six membered aromatic heterocycle containing from 1 to 3 heteroatoms selected from the group consisting of O, N and S and wherein the substituents are members selected from the group consisting of:
  (a') halo, as defined above,
  (b') hydroxy,
  (c') (C$_1$–C$_6$)-alkyl,
  (d') (C1–C4)-perfluoroalkyl,
  (e') (C$_2$–C$_6$)-alkenyl,
  (f') (C$_2$–C$_6$)-alkynyl,
  (g') (C$_1$–C$_6$)-alkyloxy,
  (h') (C$_1$–C$_6$)-alkyl-S(O)$_n$—,
  (i') phenyl,
  (j') phenoxy,
  (k') cyano,
  (l') nitro,
  (m') CO$_2$H,
  (n') CO(C$_1$–C$_6$)-alkyl,
  (o') CO$_2$(C$_1$–C$_6$)-alkyl,
  (p') CONR$^8$R$^9$,
  (q') NR$^8$R$^9$, and
  (r') fused benzo or pyridyl group,
(s) heterocyclyl, wherein heterocyclyl is defined as a 3 to 7 atom cyclic, non-aromatic substituent containing from 1 to 3 heteroatoms selected from the group consisting of O, N, and S, said heterocycle being unsubstituted or substituted with one, two or three substituents selected from the group consisting of:
  (a') halo, as defined above,
  (b') hydroxy,
  (c') (C$_1$–C$_6$)-alkyl,
  (d') (C1–C4)-perfluoroalkyl,
  (e') (C$_2$–C$_6$)-alkenyl,
  (f') (C$_2$–C$_6$)-alkynyl,
  (g') (C$_1$–C$_6$)-alkyloxy,
  (h') (C$_1$–C$_6$)-alkyl-S(O)$_n$—,
  (i') phenyl,
  (j') phenoxy,
  (k') cyano,
  (l') nitro,
  (m') CO$_2$H,
  (n') CO(C$_1$–C$_6$)-alkyl,
  (o') CO$_2$(C$_1$–C$_6$)-alkyl,
  (p') CONR$^8$R$^9$,
  (q') NR$^8$R$^9$,
  (r') NR$^8$CO(C$_1$–C$_6$)-alkyl,
  (s') oxo,
  (t') fused benzo, and
  (u') fused pyridyl group;
(t) benzyl-S(O)$_n$—,
(u) O[(C=O)O$_r$]$_s$(C$_2$–C$_6$)-alkenyl,
(v) O[(C=O)O$_r$]$_s$aryl,
(w) O[(C=O)O$_r$]$_s$heteroaryl,
(x) O(CH$_2$)$_n$heteroaryl, or
(y) O(CH$_2$)$_n$aryl;
(20) (C$_2$–C$_{10}$)-alkenyl, wherein alkenyl is unsubstituted or substituted with one or two of the substituents selected from the group consisting of:
  (a) halo, wherein halo is fluoro, chloro, bromo, or iodo,
  (b) hydroxy,
  (c) oxo,
  (e) (C$_1$–C$_6$)-alkyl-S(O)$_n$—,
  (f) phenyl-(C$_1$–C$_6$)-alkyloxy,
  (g) cyano,
  (h) nitro,
  (i) NR$^8$R$^9$,
  (j) CHO,
  (k) CO$_2$H,
  (l) CO(C$_1$–C$_6$)-alkyl,
  (m) CO$_2$(C$_1$–C$_6$)-alkyl,
  (n) CONR$^8$R$^9$,
  (o) aryl, wherein aryl is as defined above,
  (p) heteroaryl, wherein heteroaryl is as defined above,
  (q) heterocyclyl, wherein heterocyclyl is as defined above,
  (r) O[(C=O)O$_r$]$_s$(C$_1$–C$_6$)-alkyl, alkyl as defined above,
  (s) O[(C=O)O$_r$]$_s$(C$_2$–C$_6$)-alkenyl, as defined above,
  (t) O[(C=O)O$_r$]$_s$aryl, aryl as defined above,
  (u) O[(C=O)O$_r$]$_s$heteroaryl, heteroaryl as defined above,
  (v) O(CH$_2$)$_n$heteroaryl, heteroaryl as defined above, and
  (w) O(CH$_2$)$_n$aryl, aryl as defined above;
(21) (C$_2$–C$_{10}$)-alkynyl, wherein alkynyl is unsubstituted or substituted with one or two of the substituents selected from the group consisting of:
  (a) halo, wherein halo is fluoro, chloro, bromo, or iodo,
  (b) hydroxy,
  (c) oxo,
  (d) (C$_1$–C$_6$)-alkyloxy,
  (e) (C$_1$–C$_6$)—S(O)$_n$—, (f) phenyl-($C_1$-$C_6$)-alkyloxy,
(g) cyano,
(h) nitro,
(i) vinyl,
(j) $NR^8R^9$,
(k) $NR^8CO(C_1$-$C_6)$-alkyl,
(l) CHO,
(m) $CO_2H$,
(n) $CO(C_1$-$C_6)$-alkyl,
(o) $CO_2C(C_1$-$C_6)$-alkyl,
(p) $CONR^8R^9$,
(q) aryl, wherein aryl is as defined above,
(r) heteroaryl, wherein heteroaryl is as defined above,
(s) heterocyclyl, wherein heterocyclyl is as defined above,
(t) $O[(C=O)O_r]_s(C_1$-$C_6)$-alkyl, alkyl as defined above,
(u) $O[(C=O)O_r]_s(C_2$-$C_6)$-alkenyl, as defined above,
(v) $O[(C=O)O_r]_s$aryl, aryl as defined above,
(w) $O[(C=O)O_r]_s$heteroaryl, heteroaryl as defined above
(x) $O(CH_2)_n$heteroaryl, heteroaryl as defined above, and
(y) $O(CH_2)_n$aryl, aryl as defined above,
(22) $O[(C=O)O_r]_s(C_1$-$C_6)$-alkyl, alkyl as defined above,
(23) $O[(C=O)O_r]_s(C_2$-$C_6)$-alkenyl, as defined above,
(24) $O[(C=O)O_r]_s$aryl, aryl as defined above,
(25) $O[(C=O)O_r]_s$heteroaryl, heteroaryl as defined above
(26) $O(CH_2)_n$heteroaryl, heteroaryl as defined above,
(27) aryl, wherein aryl is as defined above,
(28) $O[(C=O)O_r]_s$heteroaryl, heteroaryl as defined above,
(29) $O(CO)NH(CH2$—$CO$—$NR^8R^9)$, or
(30) $O(CH_2)_n$aryl, aryl as defined above;
$R^3$ can also be any of the following when a is a single bond and $R^4$ is absent:
(31) oxo,
(32) =CH—($C_1$-$C_6$)-alkyl, wherein alkyl is as defined above,
(33) =CH—($C_2$-$C_6$)-alkenyl, wherein alkenyl is as defined above,
(34) =CH-aryl, wherein aryl is as defined above,
(35) =$CH_2$, or
$R^3$ and $R^4$ can be taken together to form a spiro-fused heterocyclyl group, wherein heterocyclyl is as defined above, or
$R^3$ and $R^5$ can be taken together to form a fused oxirane when a is a single bond, with the proviso that $R^4$ is absent when a is a double bond;
$R^5$ is:
(1) hydrogen,
(2) halogen,
(3) ($C_2$-$C_6$)-alkenyl,
(4) hydroxy,
(5) $O[(C=O)O_r]_s(C_1$-$C_6)$-alkyl,
(6) $O(CO) NR^8R^9$,
(7) oxo, when a is a single bond, or
$R^5$ and $R^3$ can be taken together to form a fused oxirane when a is a single bond;
$R^8$ and $R^9$ are independently selected from the group consisting of:
(1) hydrogen,
(2) $[(C=O)O_r]_s$aryl, wherein aryl is as defined above,
(3) $[(C=O)O_r]_s(C_2$-$C_8)$-alkenyl, wherein alkenyl is as defined above,
(4) $[(C=O)O_r]_s(C_1$-$C_8)$-alkyl, wherein alkyl is as defined above,
(5) $(C=O)_rS(O)_n(C_1$-$C_8)$-alkyl, wherein alkyl is as defined above,
(6) $(C=O)_rS(O)_n$aryl, wherein aryl is as defined above, and
(7) heterocyclyl, wherein heterocyclyl is defined above;
$R^{10}$ is:
(1) hydrogen,
(2) $[(C=O)O_r]_s$aryl, wherein aryl is as defined above, or
(3) $[(C=O)O_r]_s(C_1$-$C_6)$-alkyl, wherein alkyl is as defined above.

A preferred embodiment is the compound of Formula II below wherein x is 2 and y is 1.

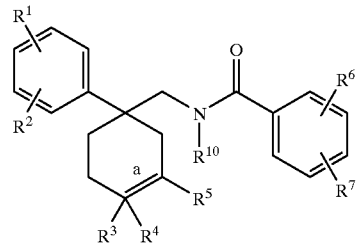

II

Yet another preferred embodiment is the compound of Formula II above, wherein a is further defined as a single bond;

$R^1$, $R^2$, $R^6$ and $R^7$ are independently:
(1) halo, wherein halo is fluoro, chloro, bromo, or iodo,
(2) hydroxy,
(3) ($C_1$-$C_6$)-alkyl,
(4) $HO(C_1$-$C_6)$-alkyloxy,
(5) ($C_1$-$C_6$)-alkyloxy, wherein the alkyl is cyclic or straight-chained,
(6) acetoxy,
(7) nitro,
(8) $NR^8R^9$,
(9) —$(O)_r(C_0$-$C_3)$-aryl, wherein aryl is phenyl or naphthyl unsubstituted or substituted with up to three substitutents selected from ($C_1$-$C_3$)alkyl, trifluoromethyl, and halo,
(10) hydrogen,
(11) $(O)_rCF_3$,
(12) ($C_1$-$C_6$)-alkyl-$S(O)_n$—, wherein n is 0, 1, 2 or 3,
(13) $(CO_2)$—($C_1$-$C_6$)-alkyl,
(14) —$(O)_r$-heteroaryl, wherein heteroaryl is pyridinyl or pyrryl,
(15) (CO)-aryl, wherein aryl is phenyl, naphthyl, benzothienyl, or benzophenone radical and is unsubstituted or substituted with up to two substituents selected from halo, trifluromethyl, and ($C_1$-$C_3$)alkyl,
(16) —$(CH_2)$—O—N=$C(CH_3)$(aryl), wherein aryl is phenyl, unsubstituted or substituted with up to three halogen substituents,
(17) —$S(O)_n$—N $R^8R^9$, or
(18) $R^1$ and $R^2$ or $R^6$ and $R^7$ can an be taken together to form a fused benzo, dihydrofuranyl, furanyl, pyrrolidyl, dihydropyrrolidyl or 1,3-dioxolan group;

$R^3$ and $R^4$ are independently:
(1) halo, wherein halo is fluoro, chloro, bromo, or iodo,
(2) hydroxy, (3) HO(C₁–C₆)-alkyloxy,
(4) (C=O)O(C₁–C₆)-alkyl,
(5) O(CO)CCl₃,
(6) (C₁–C₆)-alkyl-S(O)ₙ—, wherein n is 0, 1, 2 or 3,
(7) CH₂CO₂—(C₁–C₆)-alkyl,
(8) cyano,
(9) benzyloxy,
(10) CH₂OAc,
(11) OAc,
(12) (C₂–C₆)-alkenyl,
(13) (C₁–C₆)-alkyl, wherein alkyl can be unsubstituted or substituted with bromide
(14) NR⁸R⁹,
(15) O(CO)NR⁸R⁹,
(16) azido,
(17) NR⁸(CO)NR⁸R⁹,
(18) hydrogen,
(19) CH₂OH,
(20) CH₂O(C=O)phenyl, wherein phenyl is unsubstituted or monosubstituted with methoxy,
(21) O(C₂–C₆)-alkenyl,
(22) O(C=O)-phenyl, wherein phenyl is unsubstituted or monosubstituted with bromide,
(23) O(C=O)O-phenyl, wherein phenyl is unsubstituted or monosubstituted with nitro,
(24) CH₂(CO)NR⁸R⁹,
(25) O(C=O)O—(C₂–C₆)-alkenyl,
(26) O(C=O)—(C₁–C₃)-alkyl, wherein the alkyl can be unsubstituted or substituted with bromide or —CO₂CH₃,
(27) O(C₁–C₆)-alkyl, wherein alkyl can be unsubstituted or substituted with phenyl,
(28) O(C=O)O—(C₁–C₆)-alkyl,
(29) CH₂O(CO)NR⁸R⁹, or
(30) CH₂(C=O)O—(C₁–C₆)-alkyl,
R³ can also be any of the following when R⁴ is absent:
(31) oxo,
(32) =CH₂,
(33) =CH—CO₂—(C₁–C₆)-alkyl,
(34) =CH—(CO)—NR⁸R⁹, or
(35) =CH—CO₂H, or
R³ and R⁴ can be taken together to form a spiro-fused heterocyclyl group, wherein heterocyclyl is defined as:
(36) oxirane,
(37) 1,3-dioxolan,
(38) 2,2-dimethyl-1,3-dioxolan, or
(39) glycol sulfite, or
R³ and R⁵ can be taken together to form a fused oxirane;
R⁵ is:
(1) hydrogen,
(2) halogen,
(3) (C₂–C₆)-alkenyl,
(4) hydroxy,
(5) O(C=O)(C₁–C₃)-alkyl,
(6) O(CO) NR⁸R⁹,
(7) oxo, when a is a single bond, or
R⁵ and R³ can be taken together to form a fused oxirane when a is a single bond;
R⁸ and R⁹ are independently selected from the group consisting of:
(1) hydrogen,
(2) (C=O)O(C₁–C₆)-alkyl, wherein alkyl is optionally substituted with phenyl or methoxy,
(3) (C=O)phenyl, wherein phenyl is optionally substituted with bromide or methoxy,
(4) (C₁–C₆)-alkyl, wherein alkyl is optionally substituted with phenyl, methoxy, hydroxy, OCH₂OCH₃, benzylSO₃, phenylSO₃, or carboxymethyl,
(5) (C₂–C₆)-alkenyl,
(6) (C=O)O-phenyl, wherein phenyl is optionally substituted with nitro,
(7) (C=O)O(C₂–C₆)-alkenyl,
(8) (C=O)(C₁–C₃)-alkyl, wherein alkyl is optionally substituted with phenyl,
(9) (C=O)(C₂–C₄)-alkenyl,
(10) phenyl,
(11) SO₂-phenyl,
(12) SO₂-benzyl,
(13) CH₂(CO)CH₃,
(14) CH₂(CO)NH-benzyl,
(15) CH₂(CO)NH-allyl,
(16) CH₂(CO)N(CH₃)₂,
(17) CH₂(CO)NH(CH₃),

(18) 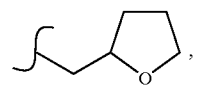

(19) 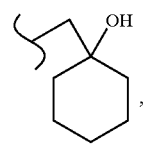

(20) 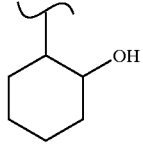

(21) 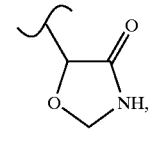

(22)

(23) 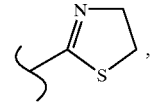

(24) CH₂CH₂NHCO₂(C₁–C₃)alkyl,
(25) CH₂CH₂O(CO)NHCH₃,
(26) CH₂CH₂O(CO)NH-allyl,
(27) CH₂CH₂NH(SO₂)CH₃,
(28) CH₂CH₂NH₂,
(29) CH₂CH₂NH(CO)CH₂CH₃, and
(30) benzyl;
R¹⁰ is:
(1) hydrogen,
(2) (C=O)phenyl, wherein phenyl is unsubstituted or substituted with F, Cl, Br, or I, or
(3) (C₁–C₃)-alkyl.

A most preferred embodiment is a compound selected from the group consisting of: trans 1-(N-ethylcarbamoyloxy)-4-phenyl-4-(3-(2-methoxyphenyl)-3-oxo-2-azaprop1-1yl)cyclohexane, trans 1-(N- allylcarbamoyloxy)-4-phenyl-4-(3-(2-hydroxy-5-fluorophenyl)-3-oxo-2-azaprop-1-yl)cyclohexane, trans 1-(N-n-propylcarbamoyloxy)-4-phenyl-4-(3-(2-methoxyphenyl)-3-oxo-2-azaprop-1-yl)cyclohexane, trans 1-(N-methylcarbamoyloxy)-4-phenyl-4-(3-(2-methoxyphenyl)-3-oxo-2-azaprop-1-yl)cyclohexane, and trans 1-(N-allylcarbamoyloxy)-4-phenyl-4-(3-(2-methoxyphenyl)-3-oxo-2-azapropyl)cyclohexane, or a pharmaceutically acceptable salt thereof.

Another most preferred embodiment is an enantiomerically pure compound or an enantiomerically enriched compound with the following structural formula:

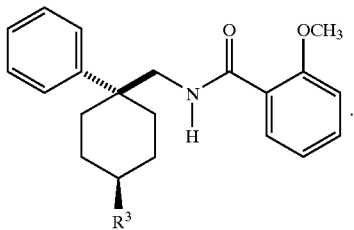

Another most preferred embodiment is an enantiomerically pure compound or an enantiomerically enriched compound with the following structural formula:

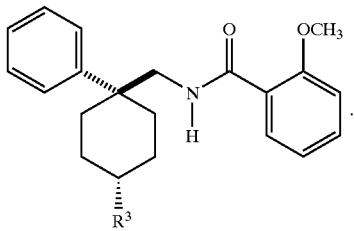

Yet another most preferred embodiment is a compound with the following structural formula:

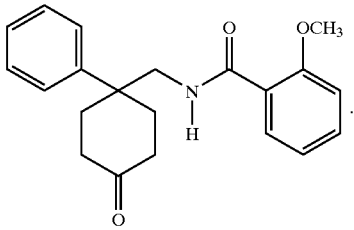

Also within the scope of the present invention is a method of treating a condition in a mammal, the treatment of which is effected or facilitated by $K_v1.3$ inhibition, which comprises administering a $K_v1.3$ inhibiting amount of the compound of Formula 1.

Preferred conditions include: resistance by transplantation of organs or tissue, graft-versus-host diseases brought about by medulla ossium transplantation, rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy, disease caused by histamine or leukotriene-$C_4$ release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augention of chemotherapeutic effect, cytomegalovirus infection, HCMV infection, AIDS, cancer, senile dementia, trauma, and chronic bacterial infection. A most preferred condition is an autoimmune disease.

Also embodied within the present invention is a method of preventing or treating resistance to transplantation or transplantation rejection of organs or tissues in a patient in need thereof, which comprises administering a therapeutically effective amount of the compound of Formula I. A method of suppressing the immune system in a subject in need thereof, which comprises administering an immune suppressing amount of the compound of Formula I is yet another embodiment.

The present invention also includes a pharmaceutical formulation comprising a pharmaceutically acceptable carrier and the compound of Formula I or a pharmaceutically acceptable crystal form or hydrate thereof. A preferred embodiment of the formulation is one where a second immunosuppressive agent is also included. Examples of such second immunosuppressive agents are, but are not limited to azathioprine, brequinar sodium, deoxyspergualin, mizaribine, mycophenolic acid morpholino ester, cyclosporin, FK-506 and rapamycin.

A further embodiment is a method of treating a condition in a mammal, the treatment of which is effected or facilitated by $K_v1.5$ inhibition, which comprises administering a compound of Formula I in an amount that is effective at inhibiting $K_v1.5$. A preferred embodiment is a method of preventing or treating cardiac arrhythmias in a mammal, which comprises administering a therapeutically effective amount of a compound of Formula 1.

The compounds of the present invention have asymmetric centers and this invention includes all of the optical isomers and mixtures thereof. Reference to one isomer is intended to apply to both isomers unless specifically indicated otherwise.

In addition compounds with carbon-carbon double bonds may occur in Z- and E-forms with all isomeric forms of the compounds being included in the present invention.

As used herein, the term "alkyl", unless otherwise indicated, includes those alkyl groups of a designated number of carbon atoms of either a straight, branched, or cyclic configuration (carbocycles). Examples of "alkyl" include methyl, ethyl, propyl, isopropyl, butyl, sec-and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy. The following illustrate the foregoing definitions: "$(C_1-C_3)$-alkyl" may be methyl, ethyl, propyl, isopropyl, or cyclopropyl. Similarly, "$O-(C_1-C_3)$-alkyl" may be methoxy, ethoxy, n-propoxy, i-propoxy, or cyclopropoxy. In some cases, a $C_0$ designation is used, as in "$-(C_0-C_2)$-alkyl-phenyl." In such a case, the substituent is intended to be any of the following: phenyl, benzyl, 1-phenylethyl, or 2-phenylethyl. In certain definitions, the alkyl may be substituted with one or more substituents. For example a definition which reads "$(C_1-C_2)$-alkyl, substituted with one or two substitutents selected from oxo, hydroxy, and halo" is intended to include $C(O)CH_3$, $CH_2BrCH_3$, $CO_2H$, $C(OH)CH_3$, $CH_2CH_2(OH)$, $CH_2CO_2H$, $CHBrCH_2Cl$, CHO, and so on.

"Alkenyl" is intended to include hydrocarbon chains of a specified number of carbon atoms of either a straight- or branched- configuration and at least one unsaturation, which may occur at any point along the chain, such as ethenyl, propenyl, butenyl, pentenyl, dimethyl pentenyl, and the like, and includes E and Z forms, where applicable. "Halogen" and "halo", as used herein, mean fluoro, chloro, bromo and iodo.

The term "aryl," unless specifically defined otherwise, is defined as phenyl or naphthyl, unsubstituted or substituted with one, two or three of the substituents selected from the group consisting of halo, hydroxy, alkyl, perfluoroalkyl, alkenyl, alkynyl, alkyloxy, alkyl-S(O)$_n$—, phenyl, phenoxy, cyano, nitro, $CO_2H$, CO-alkyl, $CO_2$-alkyl, $CONR^8R^9$, and $NR^8R^9$.

The term "heteroaryl" as utilized herein, unless specifically defined otherwise, is intended to include the following: an unsubstituted, monosubstituted, or disubstituted five or six membered aromatic heterocycle containing from 1 to 3 heteroatoms selected from the group consisting of O, N and S and wherein the substituent is halo, hydroxy, alkyl, perfluoroalkyl, alkenyl, alkynyl, alkyloxy, -alkyl-S(O)$_n$—, phenyl, phenoxy, cyano, nitro, $CO_2H$, CO-alkyl, $CO_2$-alkyl, $CONR^8R^9$, $NR^8R^9$, or a fused benzo or pyridyl group. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, pyrazinyl, pyridazinyl, pyridinyl, pyrimidinyl, and pyrrolyl which are substituted or unsubstituted as defined above.

In the compounds of Formula I, the heteroaryl or aryl groups may be optionally substituted with the substituents listed above at any available carbon atom or nitrogen atom (if present), but compounds bearing certain substitutents, directly substituted to a nitrogen may be relatively unstable and are not preferred. The heteroaryl may also be fused to a second 5-, 6-, or 7-membered ring containing one or two oxygens such as: dioxolanyl, dihydrofuranyl, dihydropyranyl, and dioxanyl. Disubstituted aryl groups may be ortho, para or meta and all three are intended unless specifically defined otherwise.

"Heterocyclyl" is defined as a 3 to 7 atom cyclic, non-aromatic substituent containing from 1 to 3 heteroatoms selected from the group consisting of O, N, and S, which is unsubstituted or substituted with one, two or three substituents selected from the group consisting of halo, hydroxy, alkyl, perfluoroalkyl, alkenyl, alkynyl, alkyloxy, alkyl-S(O)$_n$—, phenyl, phenoxy, cyano, nitro, $CO_2H$, COalkyl, $CO_2$-alkyl, $CONR^8R^9$, $NR^8R^9$, $NR^8CO$-alkyl, oxo, fused benzo, and fused pyridyl group.

Pharmaceutically acceptable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydro-scopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

Methods for preparing the compounds of this invention are illustrated in the following schemes and examples. Alternative routes will be easily discernible to practitioners in the field. The following abbreviations are used in the schemes: THF (tetrahydrofuran), PPTS (pyridinium p-toluenesulfonate), DEAD (diethylazidodicarboxylate), CDI (carbonyldiimidazole), HMPA (hexamethylphosphoramide), Tf (triflic), Boc (butoxycarbonyl), DMF (dimethylformamide), PCC (pyridinium chlorochromate), and mCPBA (meta-chloroperbenzoic acid).

REACTION SCHEME A

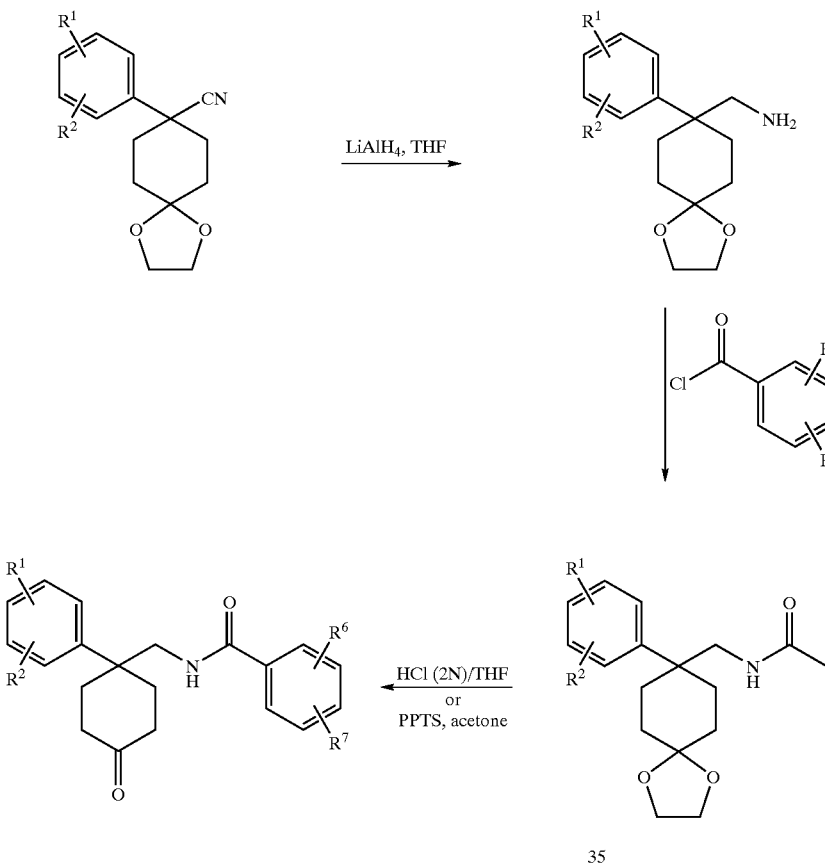

The protected 4-cyano-4-aryl cyclohexanone precursors which are starting materials to prepare the compounds of this invention are prepared according to procedures described and cited by Swenton, J. S.; Blankenship, R. M.; and Sanitra, R; J. Am. Chemical Soc., 97, 4941, 1975. Some 4-cyano-4-aryl cyclohexanone precursors are commercially available. Reduction of the nitrile group of the cyclohexyl ketal with $LiAlH_4$ in an aprotic solvent such as tetrahydrofuran (THF) preferably at elevated temperatures gives the corresponding amine derivative. The amine intermediate is acylated with acid chlorides in aprotic solvents including THF and $CH_2Cl_2$ with a base such as triethylamine to give the corresponding benzamides. The acid chlorides, when not purchased, are prepared by stirring the carboxylic acids in reagents such as oxalyl chloride or thionyl chloride. Alternatively, amides can be prepared by reaction of benzoic acids with the amine using the standard coupling conditions as described in March, J.; Advanced Organic Chemistry, 4th ed., John Wiley & Sons, New York, pp. 417–424 (1992).

The ketal group is then removed under dilute acidic conditions. A 2N solution of HCl in THF is frequently used for this transformation. These and other conditions are described in March, J.; Advanced Organic Chemistry, 4th ed., John Wiley & Sons, New York, pp. 372–375 (1992). Alternatively, the ketal group is removed by stirring in acetone with pyridinium p-toluenesulfonate (PPTS).

REACTION SCHEME B

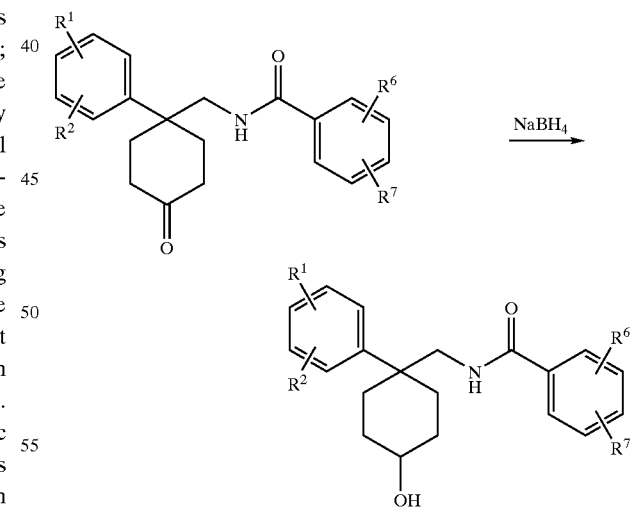

The ketone group is reduced with sodium borohydride ($NaBH_4$) in solvents such as THF or methanol to give a diastereomeric mixture of alcohols that can be separated by standard chromatography methods. $NaBH_4$ is utilized to achieve selective reduction of the ketone as described in March, J.; Advanced Organic Chemistry, 4th ed., John Wiley & Sons, New York, pp. 1206–1208 (1992).

REACTION SCHEME C

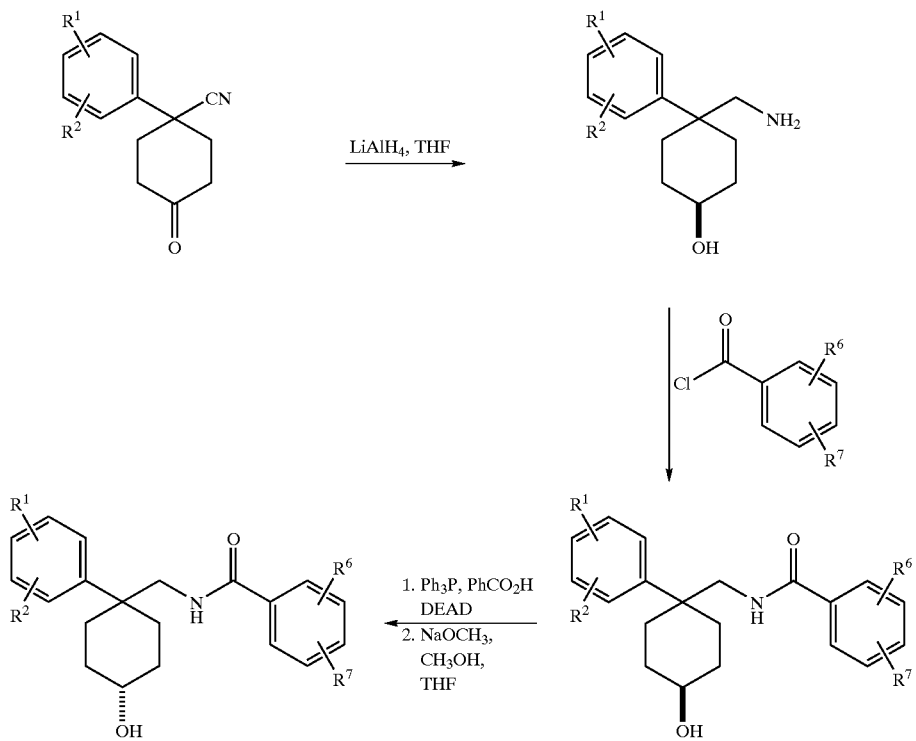

An alternate preparation is described in Reaction Scheme C. The cyano ketone is prepared according to procedures described and cited by Swenton, J. S.; Blankenship, R. M.; and Sanitra, R; J. Am. Chemical Soc., 97, 4941, 1975. Reduction to the corresponding amino alcohol occurs with $LiAlH_4$ in THF, conditions described in March, J.; Advanced Organic Chemistry, 4th ed., John Wiley & Sons, New York, pp. 910–918 and 1206–1208 (1992). With this substrate, the beta (up) alcohol is the predominant isomer. Acylation of the amino group with acids or acid chlorides using procedures described and cited in Reaction Scheme A is quite selective as long as one uses a slight excess of the substrate. Inversion of the beta hydroxy group to the alpha hydroxy group is achieved via a Mitsunobu reaction sequence as reviewed by Mitsunobu in Synthesis, 1–28 (1981).

REACTION SCHEME D

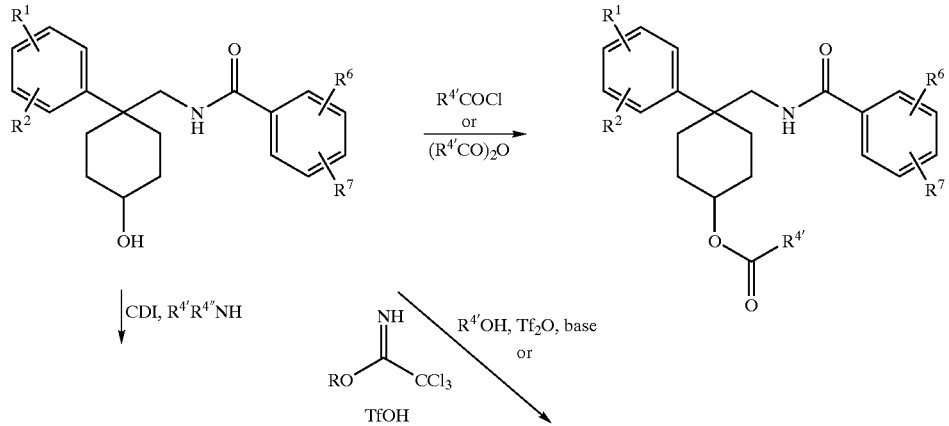

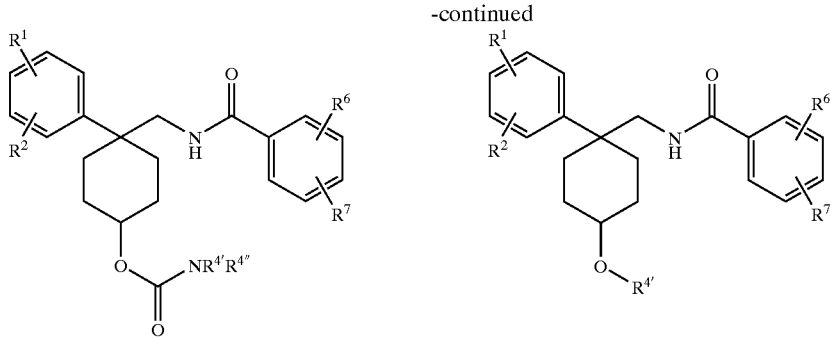

As depicted in Reaction Scheme D, esters at C1 can be prepared by reaction of an acid chloride with the C1 hydroxy group in a basic solvent such as pyridine. The acid chlorides, when not purchased, are prepared by stirring the carboxylic acids in reagents such as oxalyl chloride or thionyl chloride. Esters may also be prepared by reaction of the acid chloride and the hydroxy group with silver cyanide (AgCN) in an aprotic solvent such as HMPA. C1 sulfonate derivatives are prepared in a similar manner by reaction with sulfonyl chlorides.

C1 carbonate and carbamate derivatives are prepared by first reacting the C4 alcohol derivative with carbonyldiimidazole (CDI) to obtain the imidazolecarbonyl intermediate which is then reacted with an alcohol ($R^{4'}OH$) or amine ($R^{4'}R^{4''}NH$) to give the corresponding carbonate or carbamate derivatives. In an alternate approach, reaction of the hydroxy group with 4-nitrochloroformate provides the 4-nitrophenylcarbonate which then can be reacted with amines to give carbamates or with alcohols to give carbonate derivatives. Carbamate derivatives are also prepared with commercially available carbamoyl chlorides or isocyanates.

C1 ether derivatives can also be prepared. A particulary useful procedure involves reacting an alcohol with trifluoromethane sulfonic anhydride ($Tf_2O$, triflic anhydride) in dichloromethane at reduced temperature, preferably −78° C. to obtain the preformed triflate. To this solution is added the alcohol, the reaction mixture is warmed to room temperature and stirring is continued until reaction is complete. Ethers may also be prepared by heating a mixture of alcohol, the appropriate alkylhalide and an excess of silver oxide ($Ag_2O$) in an aprotic invert solvent such as THF. A particularly mild method of etherification is the acid-catalyzed reaction of 2,2,2-trichloroacetimidates with alcohols. (see Goulet et al., Bioorg. & Med. Chem. Letts, 4, 921–926, 1994 and references cited therein.)

REACTION SCHEME E

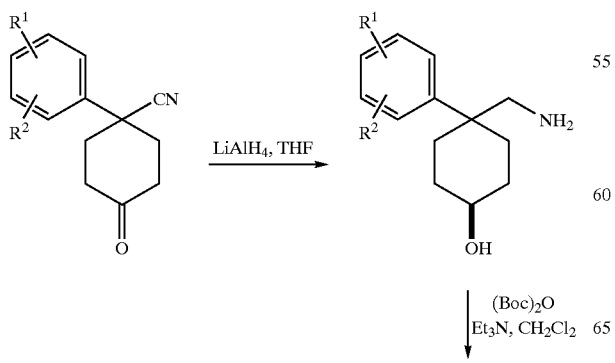

Reaction Scheme E depicts a third method of preparing compounds claimed in this invention. The amino group of the aminoalcohol derivative (Reaction Scheme C) is selectively protected with di-tert-butyl dicarbonate, a standard protecting group for amines. The beta hydroxy group can be inverted (Reaction Scheme C), and then either alcohol is derivatized according to procedures described in Reaction Scheme D. Finally, the Boc group is removed under mildly acidic conditions such as trifluoroacetic acid, and the amine is acylated by procedures described in Reaction Scheme A.

REACTION SCHEME F

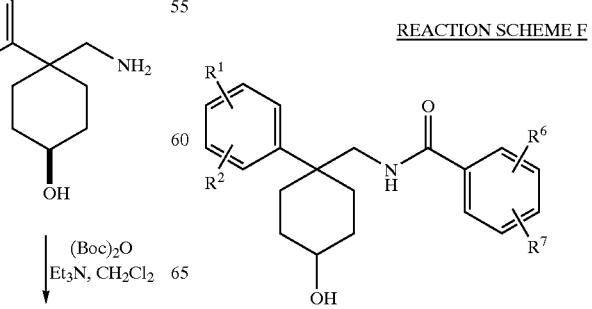

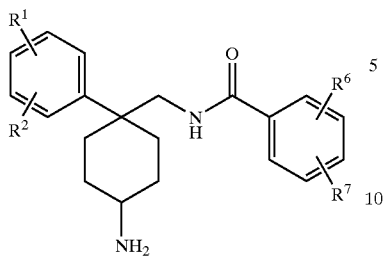

In Reaction Scheme F, the hydroxy group is converted to the corresponding amino group by well-known procedures. The hydroxy group is first derivatized as the methanesulfonate with methanesulfonyl chloride in pyridine or in THF or dichloromethane with triethylamine or pyridine. This intermediate is then reacted with sodium azide in a polar aprotic solvent such as dimethylformamide at 100° C. Alternatively, lithium azide in THF can be used. The azide displacement occurs with inversion, so that the beta hydroxy group gives the alpha azide derivative and vice versa. Finally, the azide is reduced to the corresponding amino group by hydrogenation using a palladium catalyst. This and other procedures are described in March, J.; Advanced Organic Chemistry, 4th ed., John Wiley & Sons, New York, pp. 428 and 1219 (1992).

acids in reagents such as oxalyl chloride or thionyl chloride. Amides may also be prepared from carboxylic acids by using coupling reagents such as dicyclohexyl carbodiimide as reviewed by Bodanski, The Practive of Peptide Synthesis, Springer, New York, (1984). C1 sulfonamide derivatives are prepared in a similar manner by reaction with sulfonyl chlorides.

C1 urea derivatives are prepared by first reacting the C4 amino derivative with carbonyldiimidazole (CDI) to obtain the imidazolecarbonyl intermediate which is then reacted with an amine ($R^{4'}R^{4''}NH$) to give the corresponding urea derivatives. In an alternate approach, reaction of the amino group with 4-nitrochloroformate provides the 4-nitrophenylcarbamate which then can be reacted with amines to give urea derivatives. Urea derivatives are also prepared with commercially available carbamoyl chlorides or isocyanates.

C1 carbamate derivatives are prepared in a similar manner. Reacting the C4 amino derivative with carbonyldiimidazole (CDI) gives the imidazolecarbonyl intermediate which is then reacted with an alcohol to give the corresponding carbamate derivatives. In an alternate approach, reaction of the amino group with 4-nitrochloroformate provides the 4-nitrophenylcarbamate which then can be reacted with alcohols. Carbamate derivatives are also prepared with chloroformates. For instance, reaction with ethylchloroformate will give the ethylcarbamate derivative.

The C1 amino group can be alkylated by reductive amination procedures. For instance, the C1 amino group is

REACTION SCHEME G

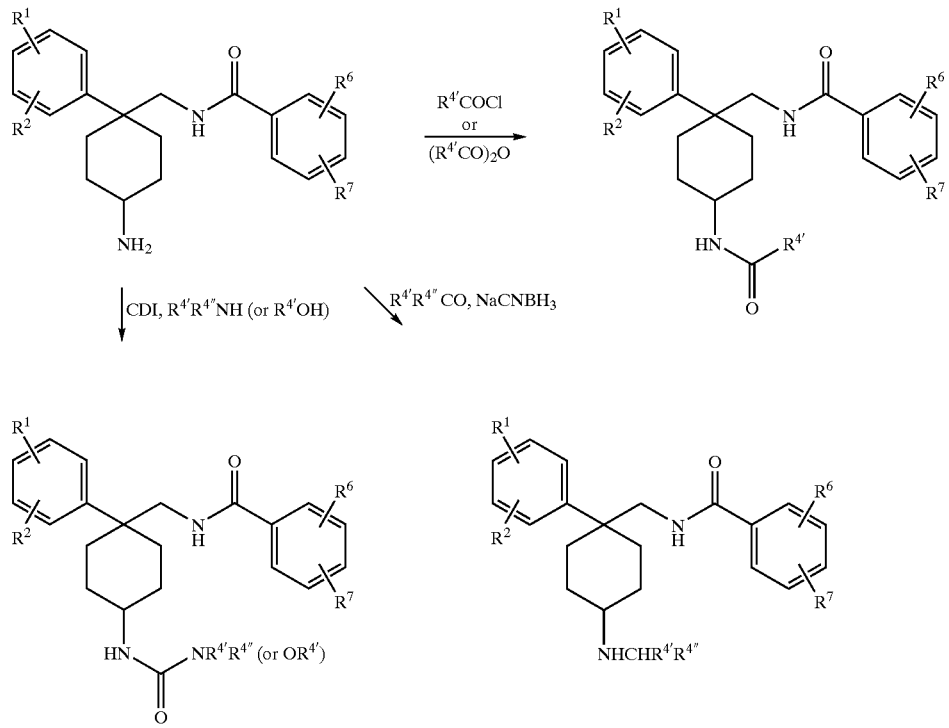

As depicted in Reaction Scheme G, amides at C1 can be prepared by reaction of an acid chloride with the C1 amino group in a basic solvent such as pyridine. The acid chlorides, when not purchased, are prepared by stirring the carboxylic reacted with an aldehyde or ketone in the presence of sodium cyanoborohydride or sodium triacetoxyborohydride. This transformation may also be accomplished with hydrogen and a catalyst.

REACTION SCHEME H

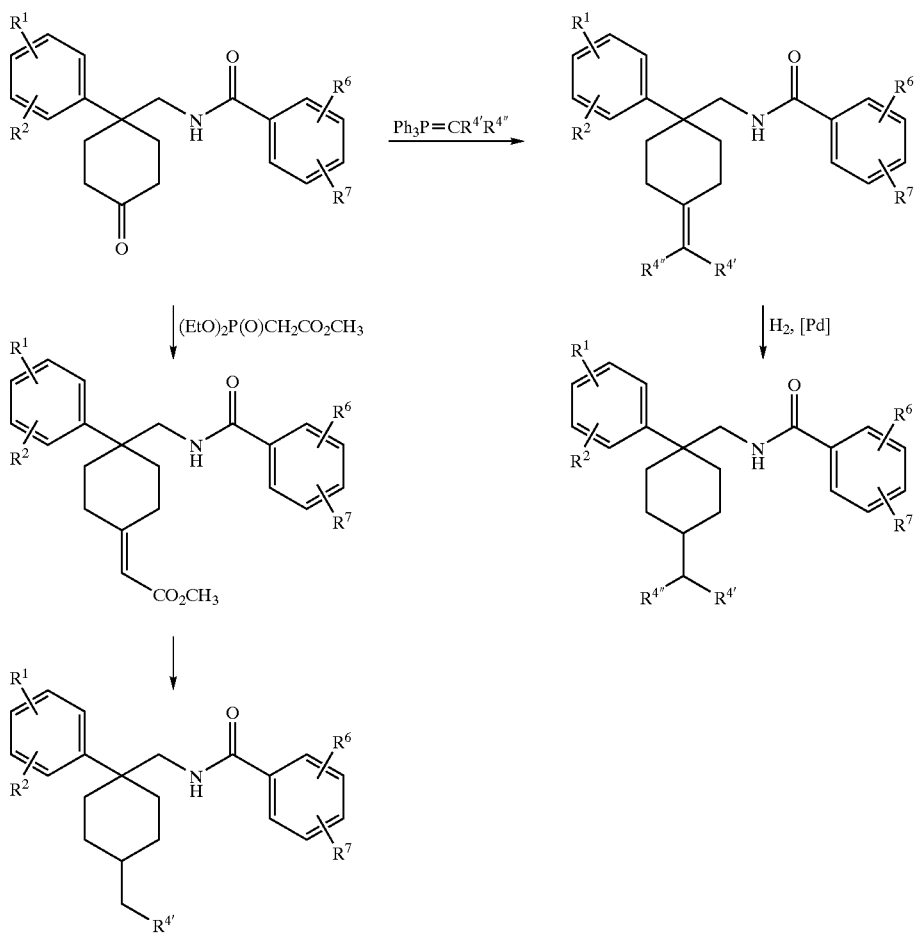

The C1 ketone can also be transformed to olefins by a variety of olefination procedures. Alkyl or arylalkyl olefins can be prepared by the Wittig-type olefination using phosphorus ylides as described by Wittig, Chem. Ber., 87, 1318 (1954). Olefins containing electron-withdrawing groups such as esters are prepared by a modification of the Wittig reagent using phosphonate reagents as depicted above. These transformations, commonly known as the Horner-Emmons, Wadsworth-Emmons or Wittig-Horner reactions, are reviewed in March, J.; Advanced Organic Chemistry, 4th ed., John Wiley & Sons, New York, pp. 956–965 (1992).

Olefin products containing esters as depicted above can be further modified by procedures known to the practitioner. The double bond can be reduced by hydrogenation utilizing a catalyst such as palladium on carbon to afford a mixture of isomers at C1. Derivaitves containing an ester group can be hydrolyzed to the corresponding carboxylic acid and further modified by well-known chemical methods. Alternatively, an ester group can be reduced to an hydroxy group by various procedures. The hydroxy group can be derivatized by procedures described in Reaction Scheme D.

REACTION SCHEME I

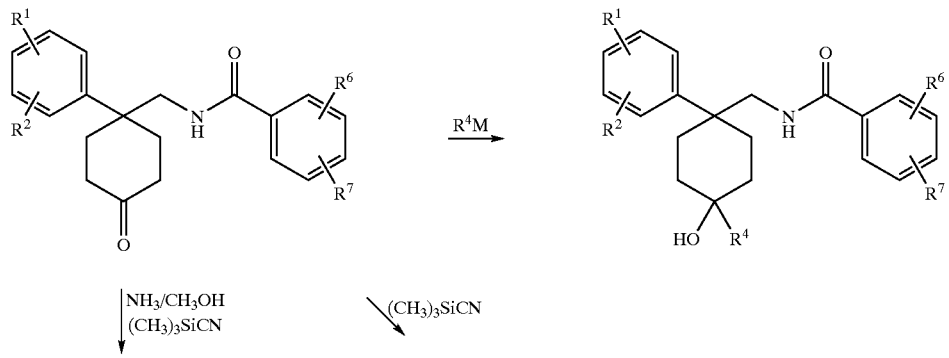

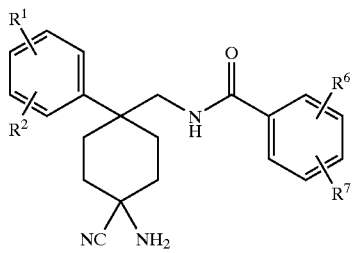
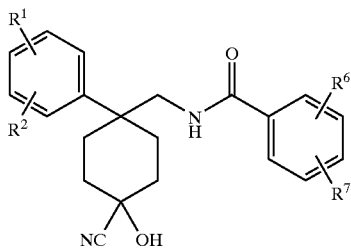

In Reaction Scheme I, alkyl metal, substituted alkylmetal or Grignard reagents will react with the C1 ketone to give the C1-substituted hydroxy derivatives. Cyanohydrins can be prepared using HCN gas, or indirectly utilizing trimethylsilylcyanide and a Lewis acid followed by hydrolysis. The hydroxy group can be further derivatized according to procedures described in Reaction Scheme D. In a modification of this procedure, reaction with trimethylsilylcyanide in methanol and ammonia gives the cyanoamine derivative. The amino group can be derivatized according to procedures described in Reaction Scheme G.

REACTION SCHEME J

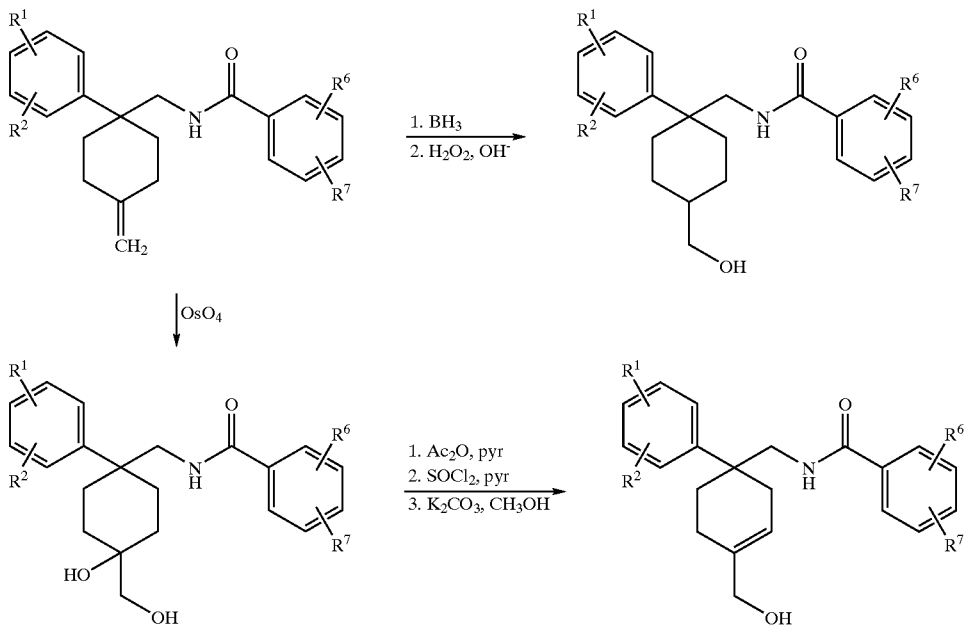

In Reaction Scheme J, the C1 exocyclic olefin derivative (Reaction Scheme H) can be hydroborated to give the C1 hydroxymethyl derivative. For optimal regioselectivity, a substituted borane reagent such as 9-borabicyclo(3.3.1)nonane (9-BBN) is preferred. Cleavage of the borane intermediate with hydrogen peroxide provides the hydroxymethyl product which can be derivatized by procedures described in Reaction Scheme D. Alternatively, it can be oxidized to a carboxylic acid and further modified by well-known chemical methods.

The C1 olefin can be bis-hydroxylated using osmium tetroxide either in stoichiometric amounts or catalytically with N-methyl morpholine-N-oxide. The primary hydroxy group can be selectively derivatized according to procedures described in Reaction Scheme D. The C1 hydroxy group of this bis-hydroxy compound can be dehydrated in a 2-step sequence. The primary hydroxy group is protected by acylation with acetic anhydride in pyridine. Treatment with thionyl chloride in pyridine leads to the depicted dehydro derivative. Finally, the acetate group can be removed under a variety of mild hydrolysis conditions. Reaction with potassium carbonate in methanol is effective.

REACTION SCHEME K

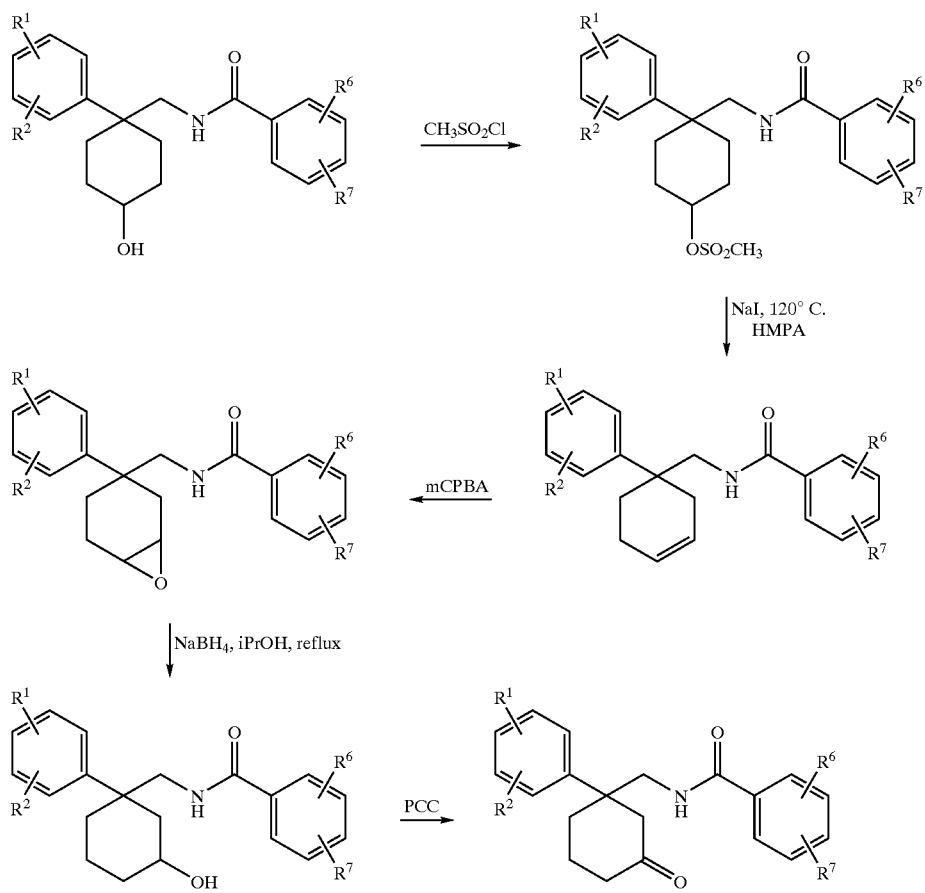

As depicted in Reaction Scheme K, the C1 hydroxy group is reacted with methanesulfonyl chloride to give the reactive methane sulfonate ester (Reaction Scheme F), which is dehydrated with sodium iodide at elevated temperatures. Epoxidation with metachloroperoxy benzoic acid gives a mixture of epoxides (alpha and beta). Reduction of the epoxide with sodium borohydride gives the transposed hydroxy derivatives. The hydroxy derivatives (alpha and beta) are then oxidized to the corresponding ketone. Pyridinium chlorochromate (PCC) is particularly effective in this transformation. The transposed hydroxy derivatives and corresponding ketone can be derivatized by procedures described in the preceeding reaction schemes.

UTILITY

The present invention is related to compounds of Formula I, including but not limited to those specified in the examples, which are useful in a mammalian subject for the treatment and prevention of immunemediated diseases such as the resistance by transplantation of organs or tissue such as heart, kidney, liver, medulla ossium, skin, cornea, lung, pancreas, intestinum tenue, limb, muscle, nervous, duodenum, small-bowel, pancreatic-islet-cell, including xeno transplants, etc.; graft-versus-host diseases brought about by medulla ossium transplantation; autoimmune diseases such as rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, and the like; and further infectious diseases caused by pathogenic microorganisms. Further uses may include the treatment and prophylaxis of inflammatory and hyperproliferative skin diseases and cutaneous manifestations of immunologically mediated illnesses, such as psoriasis, atopical dermatitis, contact dermatitis and further eczematous dermatitises and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scieritis, Graves' opthalmopathy, Vogt-Koyanagi-Harada syndrome, sarcoidosis, etc.; pollen allergies, reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucous and blood vessels such as gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases; intestinal inflammations/ allergies such as Coeliac diseases, proctitis, eosinophilic gastroenteritis, mastocytosis, Crohn's disease and ulcerative colitis; food-related allergic diseases which have symptomatic manifestation remote from the gastrointestinal tract (e.g. migraine, rhinitis and eczema); renal diseases such as interstitial nephritis, Good-pasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fascitis; periodontal disease such as lesions of gingiva, periodontium, alveolar bone and substantia ossea dentis; nephrotic syndrome such as glomerulonephritis; male pattern alopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis (e.g. necrosis caused by toxin, viral hepatitis, shock, or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases such as augmention of chemotherapeutic effect, preventing or treating activity of cytomegalovirus infection, particularly HCMV infection, and antiinflammatory activity.

The compounds of the present invention may also be used in the treatment of immunodepression or a disorder involving immunodepression, such as AIDS, cancer, senile dementia, trauma (including wound healing, surgery and shock) chronic bacterial infection, and certain central nervous system disorders.

Using the methodologies described below, representative compounds of the invention were evaluated and found to exhibit activity in both the Kv1.3 and Kv1.5 assays, thereby demonstrating and confirming the utility of the compounds of the invention as $K_v1.3$ inhibitors and immunosuppressants, and as $K_v1.5$ inhibitors and antiarrythmics.

ASSAYS

T CELL IL-2 ASSAY

Peripheral blood mononuclear (MNC) cells from healthy donors were separated by density centrifugation with ficoll-hypaque (LSM, Organon Teknika, Durham, N.C.), followed by rosetted with neuraminidase treated sheep red blood cells (SRBC). After another centrifugation with leucocyte separation medium (LSM), the SRBC of the rosetted T cells were then lysed with ammonium chloride lysing buffer (GIBCO, Grand Island, N.Y.). Such purified T cells were resuspended at $3 \times 10^6$/mL in RPMI 1640 culture medium (GIBCO) supplemented with 10% fetal calf serum (Sigma, St. Louis, Mo.), 100 mM glutamine, 1 mM sodium pyruvate, 0.1 mM non-essential amino acids, and 1% penn-strep (GIBCO). The cell suspension was immediately distributed into 96 well round-bottom microculture plates (Costar) at 200 $\mu$L/well. The various dilutions of test compound were then added in triplicate wells at 25 $\mu$L/well, incubated for 30 min at 37° C. Ionomycin (125 ng/mL), and PMA (1 or 5 ng/mL), were added to the appropriate wells. The culture plates were then incubated at 37° C. in a humidified atmosphere of 5% $CO_2$-95% air for 18–24 hours. The supernatants were removed, and assayed for IL-2 with an IL-2 capture ELISA, using monoclonal anti-IL-2, and biotinylated goat anti-IL-2 antibodies (unconjugated antibodies purchased from R&D System, Minneapolis, Minn.). The ELISA was developed with streptavidin conjugated peroxidase (Zymed, San Francisco, Calif.) and substrate for peroxidase (Sigma). Mean OD and units of IL-2 of the replicate wells were calculated from standard curve, created with recombinant IL-2 (Collaborative Biomedical Products, Bedford, Mass.) and the results were expressed as concentration of compound required to inhibit IL-2 production of T cells by 50%.

T CELL PROLIFERATION ASSAY

Peripheral blood mononuclear cells (MNC) from healthy donors were separated by density centrifugation with ficoll-hypaque (LSM, Organon Teknika, Durham, N.C.). After washing the MNC with complete media (RPMI 1640 medium with 5% fetal calf serum, 100 mM glutamine, 1 mM sodium pyruvate, 0.1 mM non-essential amino acid, and 1% penn-strep, obtained from GIBCO, Grand Island, N.Y.), they were then irradiated at 7500 RADS, and resuspended at $4–4.5 \times 10^6$ cells/mL in complete media. Another aliquot of MNC were rosetted with neuraminidase treated SRBC. After another centrifugation with LSM, the sheep red blood cells (SRBC) of these rosetted T cells were then lysed with ammonium chloride lysing buffer (GIBCO, Grand Island, N.Y.). After washing 2x with complete media, these purified T cells were also resuspended at $2–2.5 \times 10^6$ cells/mL in complete media. The various dilutions of the compound were added in triplicates at 50 ul/well of a 96 well flat-bottom microculture plate (Costar, Cambridge, Mass.). T cell suspension was then immediately distributed into the wells at 100 ul/well. After incubating the cells with compound for 30 min. at 37° C. in a humidified atmosphere of 5% $CO_2$-95% air, 20 μA/well of anti-CD3 (Ortho Diagnostic, NJ) at final conc. of 0.3 ng/mL was added, followed by 50 μA of the irradiated MNC. The culture plates were then incubated at 37° C. in a humidified atmosphere of 5% $CO_2$-95% air for 72 hours. The proliferation of T lymphocytes was assessed by measurement of tritiated thymidine incorporation. During the last 18–24 hrs. of culturing, the cells were pulse-labeled with 2 μCi/well of tritiated thymidine (NEN, Cambridge, Mass.). The cultures were harvested on glass fiber filters using a multiple sample harvester (MACH-II, Wallac, Gaithersburg, Md.). Radioactivity of filter discs corresponding to individual wells was measured by standard liquid scintillation counting methods (Betaplate Scint Counter, Wallac). Mean counts per minute of replicate wells were calculated and the results were expressed as concentration of compound required to inhibit tritiated thymidine uptake of T cells by 50%.

$K_v1.3$-RUBIDIUM EFFLUX ASSAY

CHO cells transfected with $K_v1.3$ channels at site densities of approximately 40,000 sites/cell are plated into 96 well culture plates and maintained in Iscove's Modified Dulbecco's Medium (IMDM, with L-Glutamine and HEPES, JRH Biosciences). Cells are incubated overnight with $^{86}Rb^+$ (3 μCi/mL, Dupont-NEN) in the glutamine supplemented IMDM. After aspiration of the media, 100 μL of Low K Buffer (in mM, 6.5 KCl, 125 NaCl, 1 $CaCl_2$, 2 $MgCl_2$, 10 HEPES, pH adjusted to 7.2 with NaOH) is added to each well followed by 100 μL test samples in Low K Buffer also containing 0.2% BSA and 2 mM ouabain. Samples are tested at either 1 μg/mL for routine screening or at a variety of concentrations encompassing at least ¹⁄₁₀ to 10 times the putative $IC_{50}$ of test compound to determine potency. After a fixed preincubation time, which is usually 10 min, the samples are aspirated. The $K_v1.3$ channels are opened by depolarization of the cells with High K Buffer (final concentrations, in mM, 63.25 KCl, 68.25 NaCl, 1 $CaCl_2$, 2 $MgCl_2$, 10 HEPES, pH adjusted to 7.2 with NaOH) also containing test compounds. To measure $^{86}Rb^+$ efflux through the channels, aliquots of 100 μL are taken from each well after a given time and added to plates containing 100 μL MicroScint-40 (Packard) for counting by liquid scintillation techniques. MicroScint-40 (100 μL) is then added to each well of the cell plate to determine the remaining $^{86}Rb^+$ activity. The efflux counts are normalized for the total amount of $^{86}Rb^+$ that was in the cells by adding the efflux counts to the cell plate counts. Activity is determined by % inhibition of the efflux window that is established using a saturating concentration of margatoxin (MgTX), a 39 amino acid peptide that is a potent blocker of $K_v1.3$ channels ($IC_{50}$=100 pM).

$K_v1.5$-RUBIDIUM EFFLUX ASSAY

The Kv1.5 $^{86}Rb^+$ (a potassium ion surrogate) efflux assay utilizes HEK 293 cells engineered to stably express the human Kv1.5 potassium channel. Cells are seeded at a density of 25000 cells/well in poly-D-lysine coated 96-well Packard CulturPlates one to three days prior to the assay and loaded with $^{86}Rb^+$ (0.05 microcuries/well) the day before assay. On the day of assay, plates are washed three times using a Skatron 96-well plate washer and two hundred microliters of low KCl buffer (125 mM NaCl, 6.5 mM KCl, 1 mM $CaCl_2$, 2 mM $MgCl_2$, 0.02% bovine serum albumin, 10 mM HEPES, pH 7.2) with or without inhibitor is added to each well. After ten minutes at room temperature, the plates are washed one time with low KCl buffer and two hundred microliters of high KCl buffer (same as low KCl buffer except KCl is 60 mM and NaCl is 65 mM) with or without inhibitor is added to the appropriate wells to activate the Kv1.5 channel. The plates are incubated for an additional ten minutes at room temperature at which time one hundred microliters of each supernatant is transferred to a 96-well Packard OptiPlate. The cell plates are immediately washed one time with low KCl buffer followed by the addition of one hundred microliters of low KCl buffer to each well. One hundred microliters of Microscint scintillation cocktail is added to each well of the supernatant and cell plates and radioactivity is determined on a Packard TopCount scintillation counter. The reduction of supernatant $^{86}Rb^+$ is used to quantitate the degree of inhibition of the Kv1.5 potassium channel.

Di-TRITIUM CORREOLIDE (DiTC) BINDING ASSAY

Activity of compounds can be evaluated by determining their effect on DiTC binding to either Kv1.3 or Kv1.5 channels expressed in human embryonic kidney cells (HEK). The Kv1.3 and Kv1.5 channels used are cloned human channels. DiTC is also known as L-765,910 and is a natural product analogue which binds specifically to Kv1.x channels, such as Kv1.3 and Kv1.5. In general, compounds are incubated at given concentrations in the presence of 20 nM DiTC (10 μM cold ligand is used to define non-specific binding) and either HEK/$K_v1.3$ or HEK/Kv1.5 membranes, in a buffer containing 135 mM NaCl, 4.6 mM KCl, 20 mM Tris, pH=7.4 (tris[hydroxymethyl]aminomethane), and 0.02% bovine serum albumin (BSA). Binding is allowed to reach equilibrium by incubation of the samples at room temperature for 24 hrs. Separation of bound from free ligand is achieved by filtration through GF/C filters and washing with ice-cold buffer containing 100 mM NaCl, 20 mM Tris (pH=7.4), and 0.04% BSA. Scintilltion fluid is added to the samples and radioactivity associated with filters determined by liquid scintillation techniques. Specific DiTC binding is the difference between total and non-specific binding. The activity of a given compound is assessed relative to an untreated control.

HEK cells expressing either human Kv1.3 or Kv1.5 channels were grown by Analytical Biological Services in bioreactors containing MEM supplemented with FBS, Penicillin, Streptomycin, and Geneticin. Seven tubes of frozen cell pellets (25 L of cells) were then thawed and 20 mL Homogenization Buffer was added to each tube. The contents of the tubes were pooled into a 50 mL glass/Teflon homogenizer. The cells were homogenized for 10 strokes (500 rpm) and transferred to 50 mL tubes. The tubes were then centrifuged at 1000 rpm for 5 min at 4° C. (253×g, Beckman GPR). The supernatant was collected and set aside on ice. The pellets were resuspended in a total of 40 mL Lysis Buffer, homogenized as described above, and the homogenate was centrifuged as described above. The supernatant was added to the set aside supernatant. The pooled supernatant was then centrifuged at 40,000 rpm for 45 min at 4° C. (186,000×g, Beckman 45TI). The pellet was resuspended in 70 mL Storage Buffer by homogenization as described above. Aliquots were flash frozen using liquid nitrogen and stored at −70° C. (Homogenization Buffer: 250 mM Sucrose, 5 mM $MgCl_2$, 20 mM Tris, pH=7.4; Storage Buffer: 100 mM NaCl, 20 mM HEPES, pH=7.4).

DOSAGE FORMS

As an immunosuppressive, these compounds are useful in the treatment of autoimmune diseases, the prevention of rejection of foreign organ transplants and/or related afflictions, diseases and illnesses.

The compounds of this invention can be administered for the treatment of autoimmune diseases, the prevention of rejection of foreign organ transplants and/or related afflictions, diseases and illnesses according to the invention by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1–500 milligrams per day. Ordinarily, from 10 to 100 milligrams per day in one or more applications is effective to obtain desired results. These dosages are the effective amounts for the treatment of autoimmune diseases, the prevention of rejection of foreign organ transplants and/or related afflictions, diseases and illnesses.

The active ingredient can be administered orally in solid dosage forms, such as capsules, tablets, troches, dragees, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention can be illustrated as follows:

CAPSULES

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

SOFT GELATIN CAPSULES

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules' are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol. The solution is made to volume with water for injection and sterilized.

SUSPENSION

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

The following examples illustrate the preparation of the compounds of Formula I and as such are not to be considered as limiting the invention set forth in the claims appended hereto.

EXAMPLE 1 trans and cis 1-Hydroxy-4-phenyl-4-(3-(2-methoxyphenyl)-3-oxo-2-azaprop-1-yl)cyclohexane

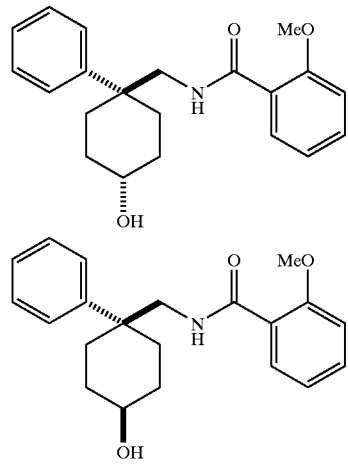

Step 1 4-Cyano-4-phenylcyclohexanone Ethyleneglycol Ketal

A solution of 20 g of 4-cyano-4-phenylcyclohexanone (100.5 mmol), 60 mL of ethylene glycol, and 1.10 g of TsOH in 65 mL of toluene was refluxed for 12 hr. The water formed during the reaction was removed via a Dean-Stark distillation receiver. The reaction mixture was concentrated under reduced pressure to remove the solvent and the residue was poured into 200 mL of ether. It was washed with water (20 mL×3), dried over $MgSO_4$ and concentrated. The residue was purified by recrystallization with hexanes: ether to afford the title compound as a white solid.

Step 2 4-Aminomethyl-4-phenylcyclohexanone Ethyleneglycol Ketal

To a suspension of 10.00 g (41.1 mmol) of 4-cyano-4-phenylcyclohexanone ethylene glycol ketal in 50 mL of dry THF was slowly added 61.65 mL of lithium aluminum hydride (1.0 M in THF, 61.65 mmol) and the reaction mixture was refluxed for 3 hr. When TLC showed no starting material the reaction mixture was cooled to 0° C. and quenched with 4 mL of 4N NaOH at 0° C. The reaction mixture was filtered through a plug of $Na_2SO_4$ and concentrated to give the title compound as a colorless oil.

Step 3 4-Phenyl-4-(3-(2-methoxyphenyl)-3-oxo-2-azaprop-1-yl)cyclohexanone

To a solution of 6.06 g (24.5 mmol) of 4-aminomethyl-4-phenylcyclohexanone ethyleneglycol ketal and 6.50 mL of triethylamine (49.0 mmol) in 60 mL of methylene chloride was added 5.44 g (31.9 mmol) of o-anisoyl chloride at 0° C. The reaction mixture was stirred for 3 hr and was poured into 200 mL of ether. It was washed with aq $NaHCO_3$, dried over $MgSO_4$ and concentrated. Then 150 mL of THF and 50 mL of 2N HCl was added into the residue. The reaction mixture were stirred for 3 hr at 40° C. Then it was poured into 200 mL of ether. The organic layer was washed with aq $NaHCO_3$, dried over $MgSO_4$ and concentrated. The residue was purified by chromatography (silica, hexanes:ethyl acetate, 1:1) to afford the compound as a solid.

Step 4 trans and cis 1-Hydroxy-4-phenyl-4-(3-(2-methoxyphenyl)-3-oxo-2-azaprop-1-yl)cyclohexane To a solution of 1.00 g (2.97 mmol) of 4-Phenyl-4-(3-(2-methoxyphenyl)-3-oxo-2-azaprop-1-yl)cyclohexanone in 30 mL of THF was added slowly 224 mg (5.93 mmol) of $NaBH_4$ at rt. The reaction mixture was stirred at rt. for 5 h and was poured into 30 mL of methylene chloride. It was washed with 10 mL of 1N HCl, dried over $MgSO_4$, and concentrated. The residue was purified by chromatography (silica, methylene chloride:tert-butyl methyl ether, 2:1) to the alpha and beta isomers of the title compound as a white solids (beta:alpha=1.6:1). When the reduction was performed in MeOH instead of THF, the alpha isomer was the major product (alpha:beta=2.5:1).

trans isomer: $^1$H NMR (CDCl$_3$) δ 1.337 (m, 2H), 1.63 (m, 2H), 1.89 (m, 2H), 2.39 (m, 2H), 3.62 (d, 2H, J=6 Hz), 3.64 (s, 3H), 3.77 (m, 1H), 6.88 (d, 1H, J=8 Hz), 7.05 (t, 1H, J=8 Hz), 7.28–7.45 (m, 5H), 7.59 (brs, 1H), 8.20 (m, 1H); Mass Spectrum (PB-NH3/CI): m/e 340 (M+1); cis isomer: $^1$H NMR (CDCl$_3$) δ 1.75–2.16 (m, 8H), 3.58 (s, 3H), 3.76 (m, 1H), 3.80 (d, 2H, J=6 Hz), 6.85 (d, 1H, J=8 Hz), 7.05 (t, 1H, J=8 Hz), 7.28–7.46 (m, 5H), 7.56 (s, 1H), 8.21 (m, 1H); Mass Spectrum (PB-NH3/CI): m/e 340 (M+1).

EXAMPLE 2 cis 1-((4-Nitrophenoxy)carbonyloxy)-4-phenyl-4-(3-(2-methoxyphenyl)-3-oxo-2-azaprop-1-yl)cyclohexane

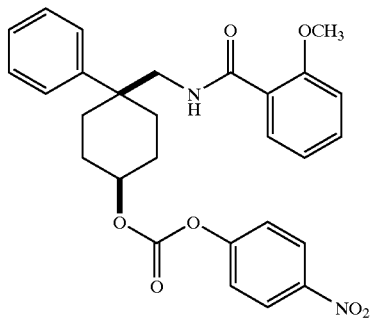

A solution of 105 mg (0.31 mmol) of cis 1-Hydroxy-4-phenyl-4-(3-(2-methoxyphenyl)-3-oxo-2-azaprop-1-yl) cyclohexane, 112 mg (0.56 mmol) of 4-nitrophenyl chlorofomate and 94 mg (0.93 mmol) of triethylamine in 10 mL of dichloromethane was stirred at rt for 3 h. The reaction mixture was concentrated and the residue was purified by chromatography (silica, hexanes:ethyl acetate, 4:1) to afford the title compound as a white solid.

$^1$H NMR (CDCl$_3$) diagnostic peaks δ 3.6 (s, 3H), 7.45 (d, 2H, J=8 Hz), 8.31 (d, 2H, J=8 Hz); Mass Spectrum (PB-NH3/CI): m/e 505.2 (M+1).

EXAMPLE 3 cis 1-((N-Allylcarbamoyl)oxy)-4-phenyl-4-(3-(2-methoxyphenyl)-3-oxo-2-azaprop-1-yl)cyclohexane

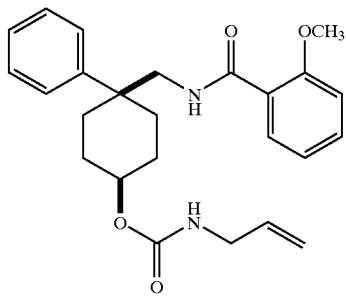

To a solution of 30 mg (0.061 mmol) of cis 1-((4-Nitrophenoxy)carbonyloxy)-4-phenyl-4-(3-(2-methoxyphenyl)-3-oxo-2-azaprop-1-yl)cyclohexane (Example 2) in 5 mL of dichloromethane was added 100 mg (1.75 mmol) of allylamine at rt. The reaction mixture were stirred for 2 hr, when it was concentrated and purified by chromatography (silica, hexanes:ethyl acetate, 2:1) to afford the title compound as a white solid.

$^1$H NMR (CDCl$_3$) δ 1.25–2.03 (m, 8H), 3.58 (s, 3H), 3.74 (d, 2H, J=6 Hz), 3.82 (t, 2H, J=6 Hz), 4.75 (brs, 1H), 4.82 (brs, 1H), 5.16 (d, 1H, J=11 Hz), 5.24 (d, 1H, 19 Hz), 5.89 (m, 1H); Mass Spectrum (PB-N H3/CI): m/e 423 (M+1).

EXAMPLE 4 cis 1-(Allyloxycarbonyloxy)-4-phenyl-4-(3-(2-methoxyphenyl)-3-oxo-2-azaprop-1-yl)cyclohexane

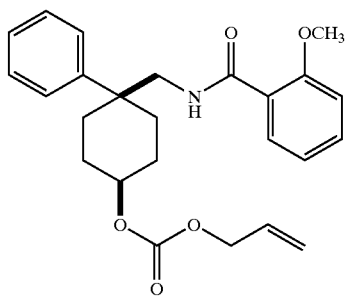

The title compound was prepared according to procedures described in Example 3 with exception that allyl alcohol was used in place of allyl amine.

$^1$H NMR (CDCl$_3$) δ 1.60–2.11 (m, 8H), 3.62 (s, 3H), 3.73 (d, 2H, J=6 Hz), 4.64 (d, 2H, J=6 Hz), 4.71 (m, 1H), 5.28 (d, 1H, J=11 Hz), 5.37 (d, 1H, J=17 Hz), 5.97 (m, 1H); Mass Spectrum (PB-NH3/CI): m/e 423.2 (M+1).

The following Examples 5 to 20 were prepared from cis 1-((4-nitrophenoxy)carbonyloxy)-4-phenyl-4-(3-(2-methoxyphenyl)-3-oxo-2-azaprop-1-yl)cyclohexane (Example 2) according to procedures described in Example 3.

EXAMPLE 5 cis 1-Carbamoyloxy-4-phenyl-4-(3-(2-methoxyphenyl)-3-oxo-2-azaprop-1-yl)cyclohexane

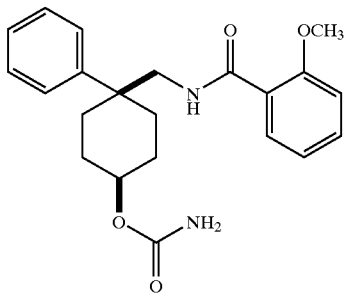

$^1$H NMR (CDCl$_3$) δ 3.59 (s, 3H), 3.74 (d, 2H, J=6 Hz), 4.74 (m, 4H); Mass Spectrum (PB-NH3/CI): m/e 425 (M+1).

EXAMPLE 6 cis 1-(N-Methylcarbamoyloxy)-4-phenyl-4-(3-(2-methoxyphenyl)-3-oxo-2-azaprop-1-yl)cyclohexane

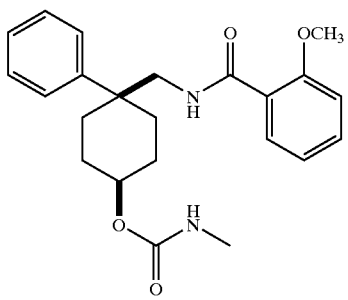

$^1$H NMR (CDCl$_3$) δ 1.70–2.06 (m, 8H), 3.81 (d, 2H, J=5.5 Hz), 3.58 (s, 3H), 3.75 (d, 2H, J=6 Hz), 4.67 (brs, 1H), 4.75 (brs, 1H); Mass Spectrum (PB-NH3/CI): m/e 397.2 (M+1).

EXAMPLE 7 cis 1-(N-Ethylcarbamoyloxy)-4-phenyl-4-(3-(2-methoxyphenyl)-3-oxo-2-azapropyl)cyclohexane

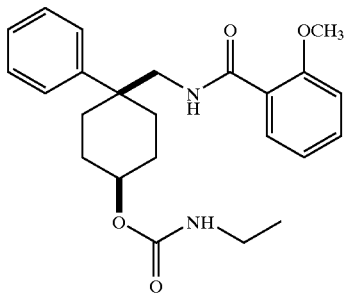

$^1$H NMR (CDCl$_3$) δ 1.16 (t, 3H, J=7 Hz), 3.22 (m, 2H), 3.58 (s, 3H), 3.73 (d, 2H, J=6 Hz), 4.74 (brs, 1H); Mass Spectrum (PB-NH3/CI): m/e 411 (M+1).

EXAMPLE 8 cis 1-(N-i-Propylcarbamoyloxy)-4-phenyl-4-(3-(2-methoxyphenyl)-3-oxo-2-azaprop-1-yl)cyclohexane

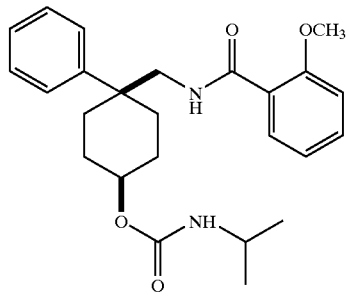

$^1$H NMR (CDCl$_3$) δ 1.17 (d, 6H, J=7 Hz), 3.59 (s, 3H), 3.75 (d, 2H, J=6 Hz); Mass Spectrum (PB-NH3/CI): m/e 425 (M+1).

EXAMPLE 9 cis 1-(N-n-Propylcarbamoyloxy)-4-phenyl-4-(3-(2-methoxyphenyl)-3-oxo-2-azaprop-1-yl)cyclohexane

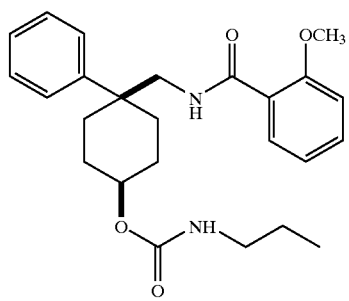

$^1$H NMR (CDCl$_3$) δ 0.94 (t, 3H, J=7.5 Hz), 1.55 (q, 2H, J$_1$=15 Hz, J$_2$=7 Hz) 3.16 (q, 2H, J$_1$=13 Hz, J$_2$=7 Hz), 3.58 (s, 3H), 3.75 (d, 2H, J=6 Hz); Spectrum (PB-NH3/CI): m/e 425 (M+1).

EXAMPLE 10 cis 1-(N,N-Diallylcarbamoyloxy)-4-phenyl-4-(3-(2-methoxyphenyl)-3-oxo-2-azaprop-1-yl)cyclohexane

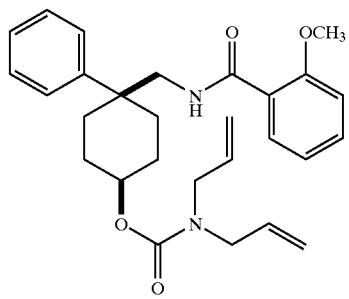

$^1$H NMR (CDCl$_3$) δ 1.63–2.06 (m, 8H), 3.58 (s, 3H), 3.72 (d, 2H, J=6 Hz) 3.89 (m, 4H), 5.14–5.18 (m, 4H), 5.82 (m, 2H); Mass Spectrum (PB-NH3/CI): m/e 463 (M+1).

EXAMPLE 11 cis 1-((N-1-Methylallyl)carbamoyloxy)-4-phenyl-4-(3-(2-methoxyphenyl)-3-oxo-2-azaprop-1-yl)cyclohexane

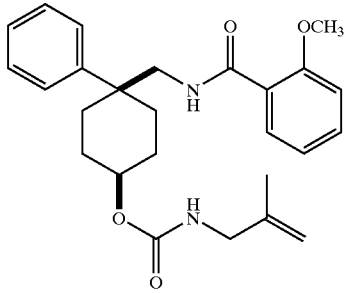

$^1$H NMR (CDCl$_3$) δ 1.79 (s, 3H), 3.59 (s, 3H), 6.87 (d, 2H, J=9 Hz), 8.22 (d, 2H, J=9 Hz); Mass Spectrum (PB-NH3/CI): m/e 437 (M+1).

EXAMPLE 12 cis 1-(N-n-Butylcarbamoyloxy)-4-phenyl-4-(3-(2-methoxyphenyl)-3-oxo-2-azaprop-1-yl)cyclohexane

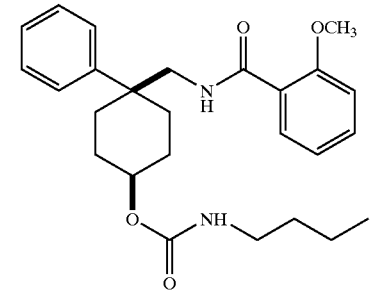

$^1$H NMR (CDCl$_3$) δ 0.94 (t, 3H, J=7 Hz), 1.38 (m, 2H), 1.49 (m, 2H), 3.19 (q, 2H, J$_1$=13 Hz, J$_2$=7 Hz), 3.59 (s, 3H), 3.75 (d, 2H, J=6 Hz); Mass Spectrum (PB-NH3/CI): m/e 439 (M+1).

EXAMPLE 13 cis 1-((N-2-Hydroxyethyl)carbamoyloxy)-4-phenyl-4-(3-(2-methoxyphenyl)-3-oxo-2-azaprop-1-yl)cyclohexane

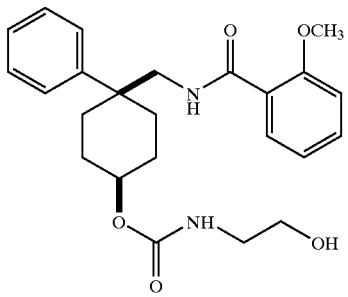

$^1$H NMR (CDCl$_3$) δ 3.37 (m, 2H), 3.59 (s, 3H), 3.76 (m, 4H); Mass Spectrum (PB-NH3/CI): m/e 427 (M+1).

EXAMPLE 14 cis 1-((N-2-Methoxyethyl)carbamoyloxy)-4-phenyl-4-(3-(2-methoxyphenyl)-3-oxo-2-azaprop-1-yl)cyclohexane

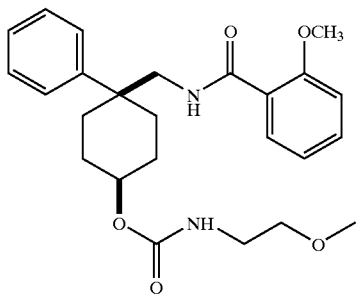

$^1$H NMR (CDCl$_3$) δ 3.76 (m, 2H), 3.40 (s, 3H), 3.48 (t, 2H, J=7 Hz), 3.59 (s, 3H), 3.75 (d, 2H, J=6 Hz); Mass Spectrum (PB-NH3/CI): m/e 441 (M+1).

EXAMPLE 15 cis 1-((N-3-Methoxy-n-propyl)carbamoyloxy)-4-phenyl-4-(3-(2-methoxyphenyl)-3-oxo-2-azaprop-1-yl)cyclohexane

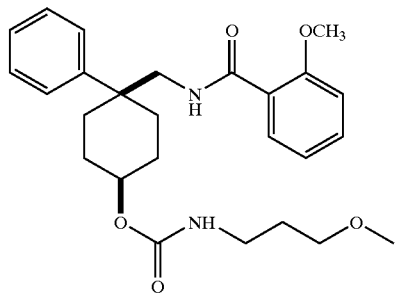

$^1$H NMR (CDCl$_3$) δ 1.78 (m, 2H), 3.29 (q, 2H, J$_1$=13 Hz, J$_2$=7 Hz), 3.39 (s, 3H), 3.47 (t, 2H, J=7 Hz), 3.59 (s, 3H), 3.75 (d, 2H, J=6 Hz); Mass Spectrum (PB-NH3/CI): m/e 455 (M+1).

EXAMPLE 16 cis 1-(N-Methyl-N-allylcarbamoyloxy)-4-phenyl-4-(3-(2-methoxyphenyl)-3-oxo-2-azapropyl)cyclohexane

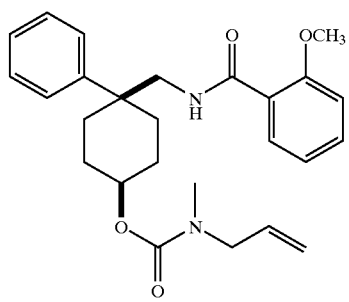

$^1$H NMR (CDCl$_3$) δ 2.90 (s, 3H), 3.51 (s, 3H), 3.75 (brs, 2H), 3.90 (d, 2H, J=7 Hz); Mass Spectrum (PB-NH3/CI): m/e 437 (M+1).

EXAMPLE 17 cis 1-(N-Phenylcarbamoyloxy)-4-phenyl-4-(3-(2-methoxyphenyl)-3-oxo-2-azaprop-1-yl)cyclohexane

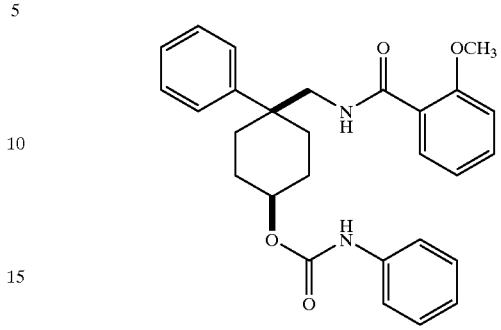

$^1$H NMR (CDCl$_3$) δ 3.60 (s, 3H), 3.75 (d, 2H, J=6 Hz), 4.88 (m, 1H); Mass Spectrum (PB-NH3/CI): m/e 459 (M+1).

EXAMPLE 18 cis 1-(N-Benzylcarbamoyloxy)-4-phenyl-4-(3-(2-methoxyphenyl)-3-oxo-2-azapropyl)cyclohexane

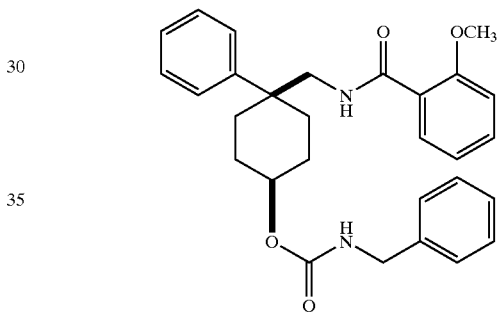

$^1$H NMR (CDCl$_3$) d 1.61–2.06 (m, 8H), 3.58 (s, 3H), 3.75 (d, 2H, J=6 Hz), 4.39 (d, 2H, J=6 Hz), 4.79 (brs, 1H), 5.04 (brs, 1H); Mass Spectrum (PB-NH3/CI): m/e 473.2 (M+1).

EXAMPLE 19 cis 1-((N-2-Phenethyl)carbamoyloxy)-4-phenyl-4-(3-(2-methoxyphenyl)-3-oxo-2-azaprop-1-yl)cyclohexane

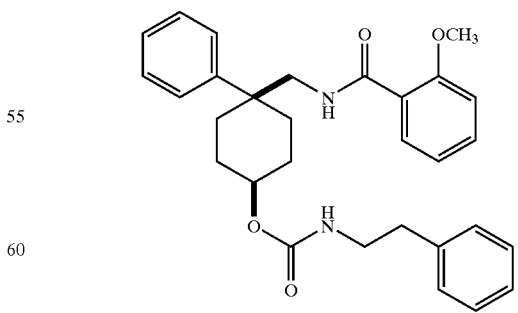

$^1$H NMR (CDCl$_3$) δ 2.85 (t, 2H, J=7 Hz), 3.45 (q, 2H, J$_1$=13 Hz, J$_2$=6 Hz), 3.58 (s, 3H), 3.73 (d, 2H, J=7 Hz); Mass Spectrum (PB-NH3/CI): m/e 487 (M+1).

EXAMPLE 20 cis 1-((N-3-Phenyl-n-propyl)carbamoyloxy)-4-phenyl-4-(3-(2-methoxyphenyl)-3-oxo-2-azaprop-1-yl)cyclohexane

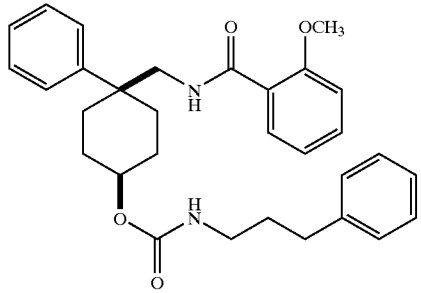

$^1$H NMR (CDCl$_3$) δ 2.68 (t, 2H, J=7.5 Hz), 3.23 (m, 2H), 3.51 (s, 3H), 3.75 (brs, 2H), 3.90 (d, 2H, J=7 Hz), 6.86–8.22 (m, 15H); Mass Spectrum (PB-NH3/CI): m/e 501 (M+1).

EXAMPLE 21 trans 1-Acetoxy-4-phenyl-4-(3-(2-methoxyphenyl)-3-oxo-2-azaprop-1-yl)cyclohexane

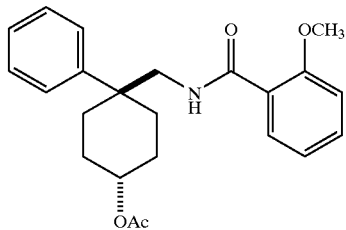

A solution of 200 mg (0.60 mmol) of trans 1-hydroxy-4-phenyl-4-(3-(2-methoxyphenyl)-3-oxo-2-azaprop-1-yl)cyclohexane, 92 mg (0.90 mmol) of acetic anhydride, 190 mg (2.40 mmol) of pyridine and 73 mg (0.6 mmol) of DMAP in 10 mL of dichloromethane was stirred at rt overnight. It was then poured into 50 mL of dichloromethane, washed with aq NaHCO$_3$, dried over MgSO$_4$ and concentrated. The residue was purified by chromatography (silica, hexanes:ethyl acetate, 4:1) to afford the title compound as a white solid.

$^1$H NMR (CDCl$_3$) δ 1.97 (s, 3H), 3.64 (s, 3H), 3.76 (d, 2H, J=7 Hz), 7.29–7.46 (m, 5H); Mass Spectrum (PB-NH3/CI): m/e 39 1.2 (M+1)

EXAMPLE 22 trans 1-((4-Nitrophenoxy)carbonyloxy)-4-phenyl-4-(3-(2-methoxyphenyl)-3-oxo-2-azaprop-1-yl)cyclohexane

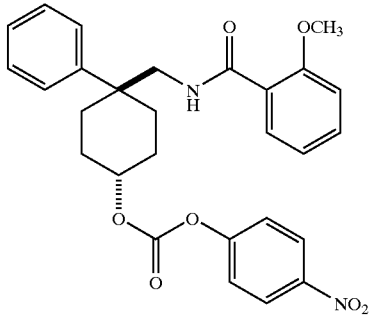

The title compound was prepared from trans 1-hydroxy-4-phenyl-4-(3-(2-methoxyphenyl)-3-oxo-2-azaprop-1-yl)cyclohexanane as described in Example 2.

$^1$H NMR (CDCl$_3$) δ 3.63 (s, 3H), 3.70 (d, 2H, J=6 Hz), 7.36 (d, 2H, J=8 Hz), 8.25 (d, 2H, J=8 Hz); Mass Spectrum (PB-NH3/CI): m/e 505.19 (M+1).

EXAMPLE 23 trans 1-Carbamoyloxy-4-phenyl-4-(3-(2-methoxyphenyl)-3-oxo-2-azaprop-1-yl)cyclohexane

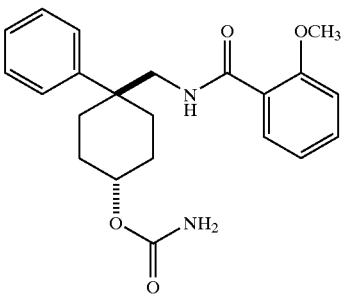

The title compound was prepared from trans 1-Hydroxy-4-phenyl-4-(3-(2-methoxyphenyl)-3-oxo-2-azaprop-1-yl)cyclohexanane according to procedures described in Example 3.

$^1$H NMR (CDCl$_3$) δ 3.63 (s, 3H), 3.64 (d, 2H, J=7 Hz), 4.63 (brs, 2H), 4.75 (m, 1H); Mass Spectrum (PB-NH3/CI): m/e 383 (M+1).

The following Examples 24 to 48 were prepared from trans 1-((4-nitrophenoxy)carbonyloxy)-4-phenyl-4-(3-(2-methoxyphenyl)-3-oxo-2-azapropyl)cyclohexane (Example 2) according to procedures described in Example 3.

EXAMPLE 24 trans 1-(N-Methylcarbamoyloxy)-4-phenyl-4-(3-(2-methoxyphenyl)-3-oxo-2-azaprop-1-yl)cyclohexane

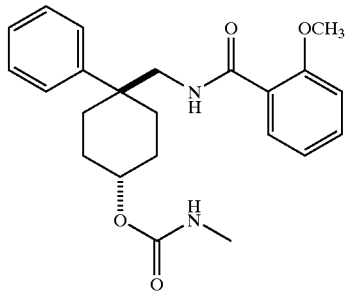

$^1$H NMR (CDCl$_3$) δ 2.75 (d, 3H, J=5 Hz), 3.63 (s, 3H), 3.57 (s, 3H,), Mass Spectrum (PB-NH3/CI): m/e 397 (M+1).

EXAMPLE 25 trans 1-(N-Ethylcarbamoyloxy)-4-phenyl-4-(3-(2-methoxyphenyl)-3-oxo-2-azapropl-1yl)cyclohexane

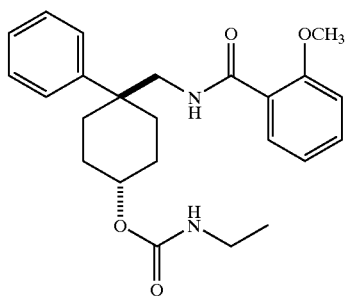

$^1$H NMR (CDCl$_3$) δ 1.07 (t, 3H, J=7 Hz), 3.15 (m, 2H), 3.62 (s, 3H), 3.64 (d, 2H, J=7 Hz), 4.58 (brs, 1H), 4.75 (brs, 1H); Mass Spectrum (PB-NH3/CI): m/e 411 (M+1).

EXAMPLE 26 trans 1-(N-n-Propylcarbamoyloxy)-4-phenyl-4-(3-(2-methoxyphenyl)-3-oxo-2-azaprop-1-yl)cyclohexane

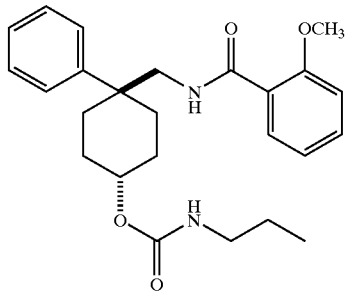

$^1$H NMR (CDCl$_3$) δ 0.88 (t, 3H, J=7 Hz), 3.10 (m, 2H), 3.63 (s, 3H), 3.65 (d, 2H, J=6 Hz), 4.54 (brs, 1H), 4.76 (brs, 1H); Mass Spectrum (PB-NH3/CI): m/e 425 (M+1).

EXAMPLE 27 trans 1-(N-i-Propylcarbamoyloxy)-4-phenyl-4-(3-(2-methoxyphenyl)-3-oxo-2-azaprop-1-yl)cyclohexane

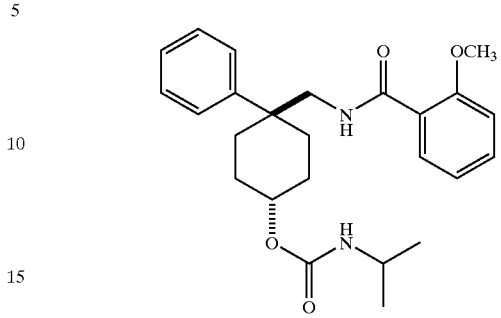

$^1$H NMR (CDCl$_3$) δ 1.09 (d, 6H, J=6 Hz), 3.63 (s, 3H), 3.65 (d, 2H, J=6 Hz), 4.36 (brs, 1H), 4.75 (brs, 1H); Mass Spectrum (PB-NH3/CI): m/e 425 (M+1).

EXAMPLE 28 trans 1-(N-Allylcarbamoyloxy)-4-phenyl-4-(3-(2-methoxyphenyl)-3-oxo-2-azapropyl)cyclohexane

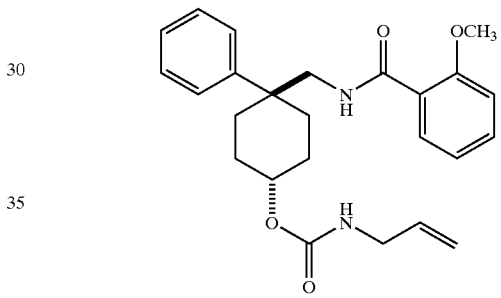

$^1$H NMR (CDCl$_3$) δ 1.49–2.34 (m, 8H), 3.63 (s, 3H), 3.64 (d, 2H, J=6 Hz), 3.77 (m, 2H), 4.61 (brs, 1H), 4.79 (brs, 1H), 5.09 (d, 1H, J=11 Hz), 5.16 (d, 1H, J=17 Hz), 5.80 (m, 1H); Mass Spectrum (PB-NH3/CI): m/e 423.2 (M+1).

EXAMPLE 29 trans 1-(N-Methyl-N-allylcarbamoyloxy)-4-phenyl-4-(3-(2-methoxy-phenyl)-3-oxo-2-azaprop-1-yl)cyclohexane

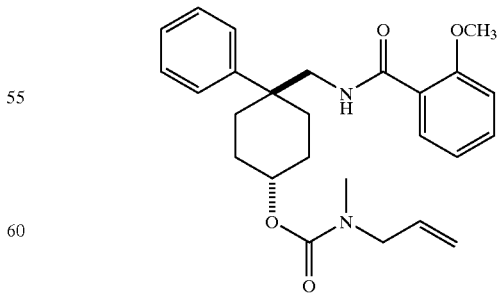

$^1$H NMR (CDCl$_3$) δ 2.79 (m, 3H), 3.62 (s, 3H), 3.65 (d, 2H, J=6 Hz), 3.74 (brs, 1H), 3.85 (brs, 1H); Mass Spectrum (PB-NH3/CI): m/e 437 (M+1).

EXAMPLE 30 trans 1-N-(1-Methylallyl)carbamoyloxy-4-phenyl-4-(3-(2-methoxyphenyl)-3-oxo-2-azaprop-1-yl)cyclohexane

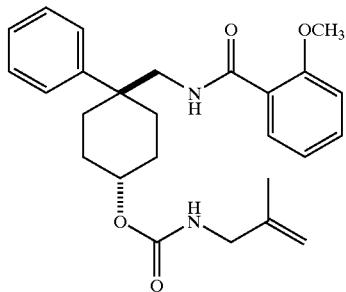

$^1$H NMR (CDCl$_3$) δ 1.72 (s, 3H), 3.64 (s, 3H), 6.87 (d, 2H, J=8 Hz), 8.21 (d, 2H, J=8 Hz); Mass Spectrum (PB-NH3/CI): m/e 437 (M+1).

EXAMPLE 31 trans 1-(N,N-Diallylcarbamoyloxy)-4-phenyl-4-(3-(2-methoxyphenyl)-3-oxo-2-azaprop-1-yl)cyclohexane

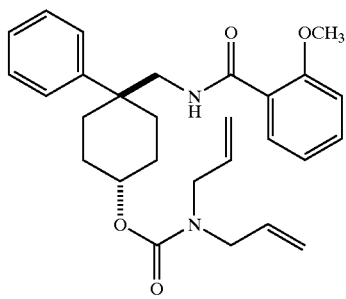

$^1$H NMR (CDCl$_3$) δ 1.56 (m, 2H), 1.79 (m, 2H), 1.96 (m, 2H), 2.03 (m, 2H), 3.63 (s, 3H), 3.66 (d, 2H, J=6 Hz), 6.87 (d, 2H, J=8 Hz), 8.21 (d, 2H, J=8 Hz); Mass Spectrum (PB-NH3/CI): m/e 463 (M+1).

EXAMPLE 32 trans 1-((N-2-Hydroxyethyl)carbamoyloxy)-4-phenyl-4-(3-(2-methoxyphenyl)-3-oxo-2-azaprop-1-yl)cyclohexane

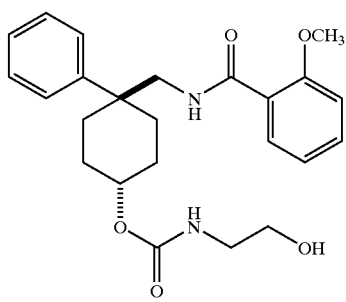

$^1$H NMR (CDCl$_3$) δ 3.28 (m, 2H), 3.62 (s, 3H), 3.65 (m, 2H), 4.74 (brs, 1H), 5.09 (brs, 1H); Mass Spectrum (PB-NH3/CI): m/e 427 (M+1).

EXAMPLE 33 trans 1-N-(2-Methoxyethyl)carbamoyloxy-4-phenyl-4-(3-(2-methoxyphenyl)-3-oxo-2-azapropyl)cyclohexane

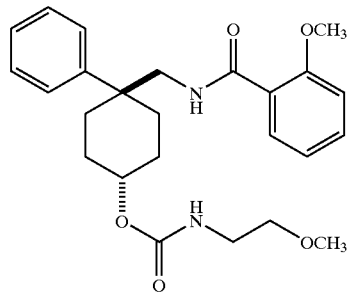

$^1$H NMR (CDCl$_3$) δ 3.32 (s, 3H), 3.41 (m, 2H), 3.63 (s, 3H), 3.65 (d, 2H, J=6 Hz), 4.77 (brs, 1H), 4.89 (brs, 1H); Mass Spectrum (PB-NH3/CI): m/e 441 (M+1).

EXAMPLE 34 trans 1-(N-n-Butylcarbamoyloxy)-4-phenyl-4-(3-(2-methoxyphenyl)-3-oxo-2-azaprop-1-yl)cyclohexane

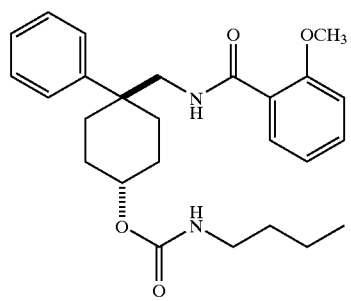

$^1$H NMR (CDCl$_3$) δ 0.90 (t, 3H, J=7 Hz), 1.28 (m, 2H), 1.42 (m, 2H), 3.13 (m, 2H), 3.63 (s, 3H), 3.65 (d, 2H, J=7 Hz); Mass Spectrum (PB-NH3/CI): m/e 439 (M+1).

EXAMPLE 35 trans 1-(N-n-Butylcarbamoyloxy)-4-phenyl-4-(3-(2-methoxyphenyl)-3-oxo-2-azaprop-1-yl)cyclohexane

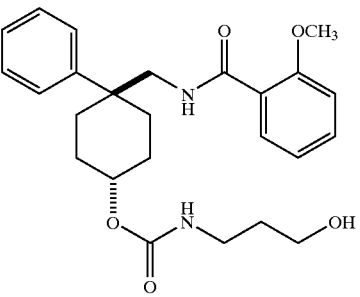

$^1$H NMR (CDCl$_3$) δ 0.93 (m, 2H), 1.47 (m, 2H), 3.30 (m, 2H), 3.64 (s, 3H), 3.66 (d, 2H, J=6 Hz); Mass Spectrum (PB-NH3/CI): m/e 441 (M+1).

EXAMPLE 36 trans 1-(N-3-Methoxy-n-propylcarbamoyloxy)-4-phenyl-4-(3-(2-methoxyphenyl)-3-oxo-2-azaprop-1-yl)cyclohexane

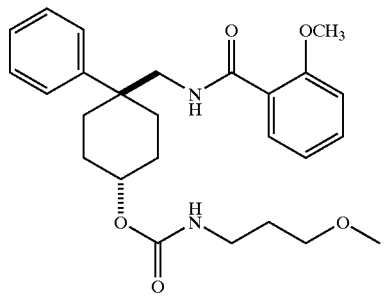

$^1$H NMR (CDCl$_3$) δ 3.23 (m, 2H), 3.29 (s, 3H), 3.40 (m, 2H), 3.62 (d, 2H, J=7 Hz), 3.64 (s, 3H); Mass Spectrum (PB-NH3/CI): m/e 455 (M+1).

EXAMPLE 37 trans 1-(N-4-Hydroxy-n-butylcarbamoyloxy)-4-phenyl-4-(3-(2-methoxyphenyl)-3-oxo-2-azaprop-1-yl)cyclohexane

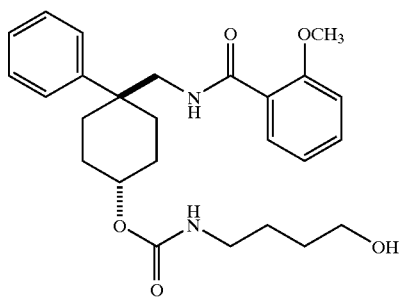

$^1$H NMR (CDCl$_3$) δ 0.89 (m, 2H), 1.46–1.52 (m, 4H), 3.14 (m, 2H), 3.62 (s, 3H); Mass Spectrum (PB-NH3/CI): m/e 455 (M+1).

EXAMPLE 38 trans 1-(N-4-Methoxy-n-butylcarbamoyloxy)-4-phenyl-4-(3-(2-methoxyphenyl)-3-oxo-2-azaprop-1-yl)cyclohexane

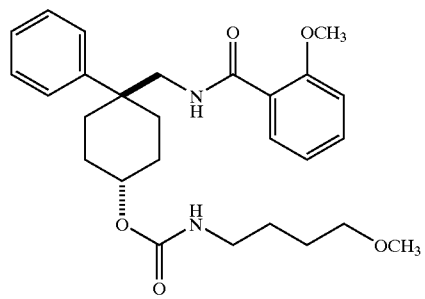

$^1$H NMR (CDCl$_3$) δ 3.15 (m, 2H), 3.30 (s, 3H), 3.63 (m, 2H), 3.63 (s, 3H), 3.65 (d, 2H, J=6 Hz); Mass Spectrum (PB-NH3/CI): m/e 469 (M+1).

EXAMPLE 39 trans 1-(N-n-Hexylcarbamoyloxy)-4-phenyl-4-(3-(2-methoxyphenyl)-3-oxo-2-azaprop-1-yl)cyclohexane

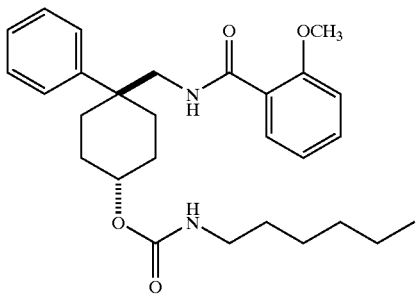

$^1$H NMR (CDCl$_3$) δ 0.86 (t, 3H, J=6 Hz), 1.25 (m, 4H), 1.42–1.46 (m, 4H), 3.10 (m, 2H), 3.61 (s, 3H), 3.63 (d, 2H, J=6 Hz); Mass Spectrum (PB-NH3/CI): m/e 467 (M+1).

EXAMPLE 40 trans 1-(N-Thiazolin-2-ylcarbamoyloxy)-4-phenyl-4-(3-(2-methoxyphenyl)-3-oxo-2-azaprop-1-yl)cyclohexane

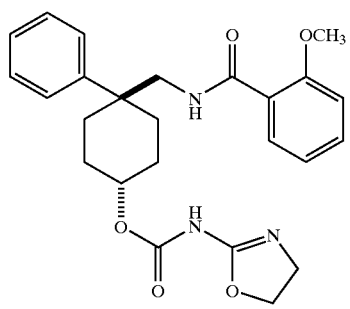

$^1$H NMR (CDCl$_3$) δ 3.03 (t, 2H, J=7 Hz), 3.62 (s, 3H), 3.65 (d, 2H, J=6 Hz), 3.97 (t, 2H, J=& Hz), 4.94 (m, 1H); Mass Spectrum (PB-NH3/CI): m/e 468 (M+1).

EXAMPLE 41 trans 1-(N-(Tetrahydrofuran-2-yl)methylcarbamoyloxy)-4-phenyl-4-(3-(2-methoxyphenyl)-3-oxo-2-azaprop-1-yl)cyclohexane

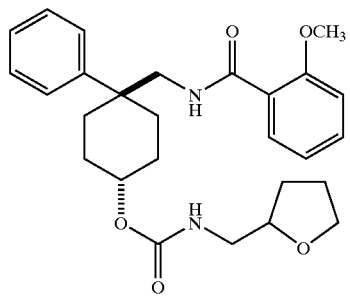

$^1$H NMR (CDCl$_3$) δ 3.09 (m, 2H), 3.40 (m, 2H), 3.62 (s, 3H), 3.65 (d, 2H, J=6 Hz); Mass Spectrum (PB-NH3/CI): m/e 467 (M+1).

EXAMPLE 42 trans 1-(N-2-(S)-Hydroxy-n-propylcarbamoyloxy)-
4-phenyl-4-(3-(2-methoxyphenyl)-3-oxo-2-azaprop-
1-yl)cyclohexane

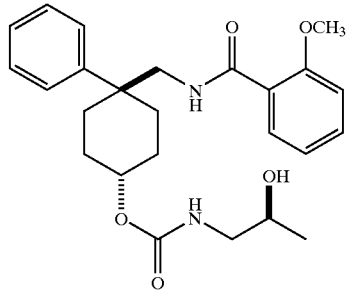

$^1$H NMR (CDCl$_3$) δ 1.08 (d, 3H, J=6 Hz), 3.57–3 63 (m, 5H); Mass Spectrum (PB-NH3/CI): m/e 441 (M+1).

EXAMPLE 43 trans 1-N-(2-(R)-Hydroxypropyl)carbamoyloxy-4-
phenyl-4-(3-(2-methoxyphenyl)-3-oxo-2-azapropyl)
cyclohexane

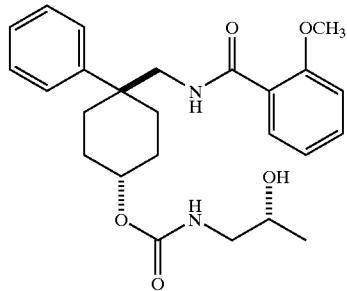

$^1$H NMR (CDCl$_3$) δ 1.10 (d, 3H, J=6 Hz), 3.22 (m, 1H), 3.59 (m, 5H), 3.82 (m, 1H), 4.72 (brs, 1H), 5.21 (d, 1H, J=7 Hz); Mass Spectrum (PB-NH3/CI): m/e441 (M+1).

EXAMPLE 44 trans 1-(N-(2-Hydroxy-1-(S)-methyl)
ethylcarbamoyloxy)-4-phenyl-4-(3-(2-
methoxyphenyl)-3-oxo-2-azapropyl)cyclohexane

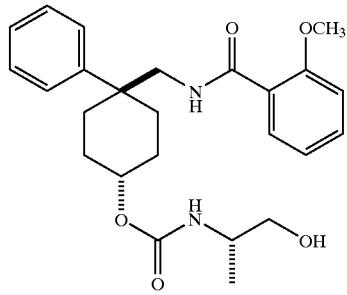

$^1$H NMR (CDCl$_3$) δ 1.08 (d, 3H, J=6 Hz), 3.46 (m, 1H), 3.59 (m, 5H), 3.74 (m, 1H), 4.72 (brs, 1H), 4.94 (d, 1H, J=7 Hz); Mass Spectrum (PB-NH3/CI): m/e 441 (M+1).

EXAMPLE 45 trans 1-(N-(2-Hydroxy-1-(R)-methyl)
ethylcarbamoyloxy-4-phenyl-4-(3-(2-
methoxyphenyl)-3-oxo-2-azaprop-1-yl)cyclohexane

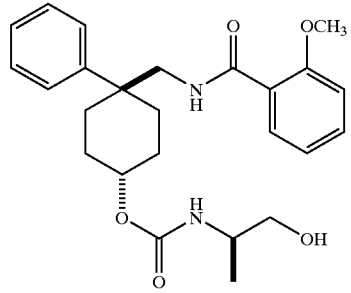

$^1$H NMR (CDCl$_3$) δ 1.08 (d, 3H, J=6 Hz), 3.46 (m, 1H), 3.59 (m, 5H), 3.74 (m, 1H), 4.72 (brs, 1H), 4.94 (d, 1H, J=7 Hz); Mass Spectrum (PB-NH3/CI): m/e 441 (M+1).

EXAMPLE 46 trans 1-(N-(1-Hydroxycyclohexyl)
methylcarbamoyloxy)-4-phenyl-4-(3-(2-
methoxyphenyl)-3-oxo-2-azaprop-1-yl)cyclohexane

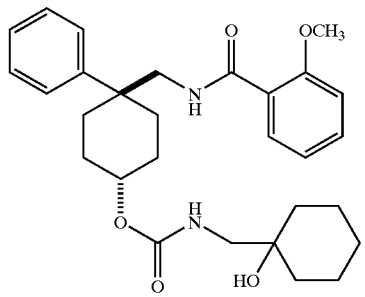

$^1$H NMR (CDCl$_3$) δ 1.26–1.54 (m, 12H), 3.12 (d, 2H, J=6 Hz), 3.59 (m, 5H), 4.72 (brs, 1H), 5.28 (m, 1H); Mass Spectrum (PB-NH3/CI): m/e 495 (M+1).

EXAMPLE 47 trans 1-N-(1-Hydroxymethylcyclopentyl)
carbamoyloxy-4-phenyl-4-(3-(2-methoxyphenyl)-3-
oxo-2-azaprop-1-yl)cyclohexane

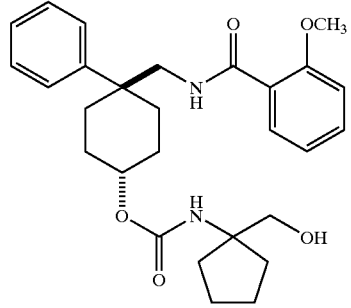

$^1$H NMR (CDCl$_3$) δ 1.58–1.73 (m, 10H), 3.59 (m, 7H), 4.72 (brs, 1H), 5.28 (s, 1H); Mass Spectrum (PB-NH3/CI): m/e 481 (M+1).

EXAMPLE 48 trans 1-(N-2-(R)-Hydroxy-1-(S)-cyclohexylcarbamoyloxy)-4-phenyl-4-(3-(2-methoxyphenyl)-3-oxo-2-azaprop-1-yl)cyclohexane

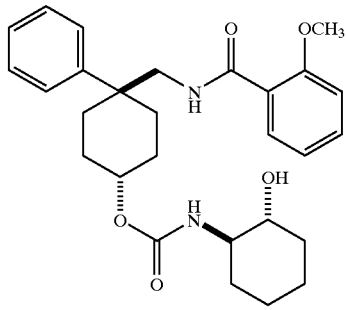

$^1$H NMR (CDCl$_3$) δ 3.24 (m, 2H), 3.59 (m, 5H), 4.80 (brs, 1H), 5.08 (m, 1H); Mass Spectrum (PB-NH3/CI): m/e 481 (M+1).

EXAMPLE 49 trans 1-(N-Phenylcarbamoyloxy)-4-phenyl-4-(3-(2-methoxyphenyl)-3-oxo-2-azaprop-1-yl)cyclohexane

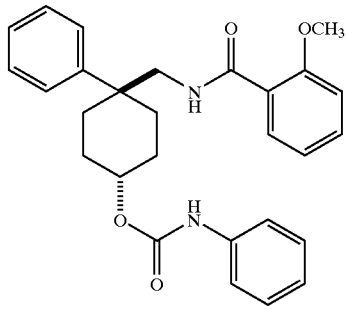

$^1$H NMR (CDCl$_3$) δ 3.60 (s, 3H), 3.67 (d, 2H, J=6 Hz), 4.89 (m, 1H); Mass Spectrum (PB-NH3/CI): m/e 437 (M+1).

EXAMPLE 50 trans 1-(N-Benzylcarbamoyloxy)-4-phenyl-4-(3-(2-methoxyphenyl)-3-oxo-2-azaprop-1-yl)cyclohexane

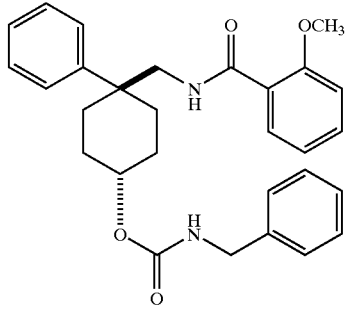

$^1$H NMR (CDCl$_3$) δ 3.64 (s, 3H), 3.66 (d, 2H, J=7 Hz), 4.37 (d, 2H, J=5 Hz), 4.80 (brs, 3H); Mass Spectrum (PB-NH3/CI): m/e 473 (M+1).

EXAMPLE 51 trans 1-(N-2-Oxopropylcarbamoyloxy)-4-phenyl-4-(3-(2-methoxyphenyl)-3-oxo-2-azaprop-1-yl)cyclohexane

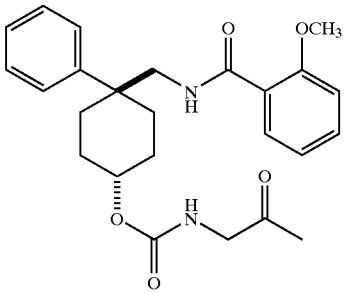

A solution of 46 mg (0.10 mmol) of trans 1-(N-2-(S)-hydroxy-n-propylcarbamoyloxy)-4-phenyl-4-(3-(2-methoxyphenyl)-3-oxo-2-azaprop-1-yl)cyclohexane (Example 41) and 90 mg (0.42 mmol) of pyridinium chlorochromate (PCC) in 5 mL of dichloromethane was stirred at rt for 2 hr. Then the reaction mixture was purified by chromatography (silica, dichloromethane:ethyl acetate, 2:1 to 1:1) to afford the title compound as a white solid.

$^1$H NMR (CDCl$_3$) δ 2.15 (s, 3H), 3.62 (m, 5H), 4.12 (d, 2H, J=7 Hz), 4.76 (m, 1H), 5.26 (m 1H); Mass Spectrum (PB-NH3/CI): m/e 439 (M+1).

EXAMPLE 52 trans 1-(N-(2-Propionyloxy)ethylcarbamoyloxy)-4-phenyl-4-(3-(2-methoxyphenyl)-3-oxo-2-azaprop-1-yl)cyclohexane

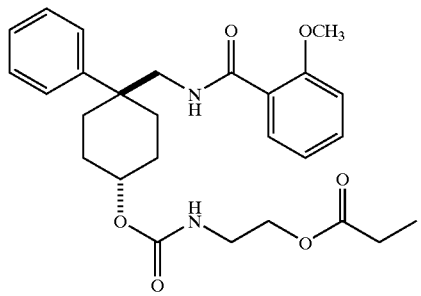

The title compound was prepared from trans 1-((N-2-hydroxyethyl)carbamoyloxy)-4-phenyl-4-(3-(2-methoxyphenyl)-3-oxo-2-azaprop-1-yl)cyclohexane (Example 32) and propionyl chloride according to procedures described in Example 21.

$^1$H NMR (CDCl$_3$) δ 1.12 (t, 3H, J=7 Hz), 2.32 (m, 2H), 3.40 (m, 2H), 3.63 (s, 3H), 3.65 (d, 2H, J=6 Hz), 4.10 (m, 2H); Mass Spectrum (PB-NH3/CI): m/e 483 (M+1).

EXAMPLE 53 trans 1-(N-(3-Propionyloxy)-n-propylcarbamoyloxy)-4-phenyl-4-(3-(2-methoxyphenyl)-3-oxo-2-azaprop-1-yl)cyclohexane

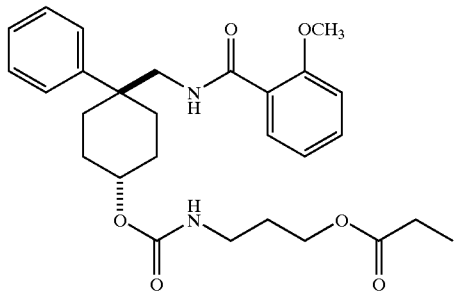

The title compound was prepared from trans 1-(N-n-butylcarbamoyloxy)-4-phenyl-4-(3-(2-methoxyphenyl)-3-oxo-2-azaprop-1-yl)cyclohexane (Example 35) and propionyl chloride as described in Example 21.

$^1$H NMR (CDCl$_3$) δ 1.10 (t, 3H, J=7 Hz), 2.32 (m, 4H), 3.20 (m, 2H), 3.62 (s, 3H), 3.64 (d, 2H, J=6 Hz), 4.10 (m, 2H); Mass Spectrum (PB-NH3/CI): m/e 497 (M+1).

EXAMPLE 54 trans 1-(N-(4-Propionyloxy)-n-butylcarbamoyloxy)-4-phenyl-4-(3-(2-methoxyphenyl)-3-oxo-2-azaprop-1-yl)cyclohexane

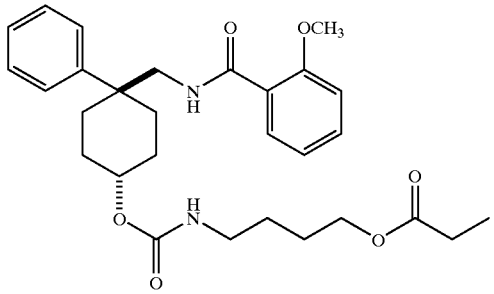

The title compound was prepared from trans 1-(N-4-hydroxy-n-butylcarbamoyloxy)-4-phenyl-4-(3-(2-methoxyphenyl)-3-oxo-2-azaprop-1-yl)cyclohexane (Example 37) and propionyl chloride as described in Example 21.

$^1$H NMR (CDCl$_3$) δ 1.12 (t, 3H, J=7 Hz), 2.31 (m, 4H), 3.17 (m, 2H), 3.62 (s, 3H), 3.64 (d, 2H, J=6 Hz), 4.06 (m, 2H); Mass Spectrum (PB-NH3/CI): m/e 511 (M+1).

EXAMPLE 55 trans 1-(N-(2-Benzylsulfonyloxy)ethylcarbamoyloxy)-4-phenyl-4-(3-(2-methoxyphenyl)-3-oxo-2-azapropyl)cyclohexane

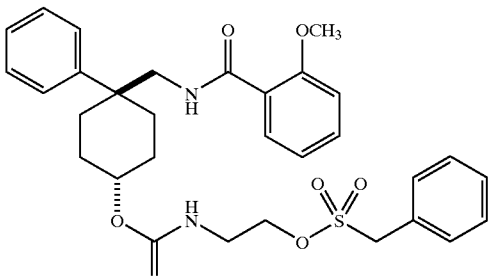

The title compound was prepared from trans 1-((N-2-hydroxyethyl)carbamoyloxy)-4-phenyl-4-(3-(2-methoxyphenyl)-3-oxo-2-azaprop-1-yl)cyclohexane (Example 32) and benzylsulfonyl chloride according to procedures described in Example 21.

$^1$H NMR (CDCl$_3$) δ 3.50 (m, 2H), 3.63 (s, 3H), 3.65 (d, 2H, J=6 Hz), 4.14 (m, 2H), 4.35 (s, 2H); Mass Spectrum (PB-NH3/CI): m/e 581 (M+1).

EXAMPLE 56 trans 1-(N-(2-Methoxymethyloxy)ethylcarbamoyloxy)-4-phenyl-4-(3-(2-methoxyphenyl)-3-oxo-2-azaprop-1-yl)cyclohexane

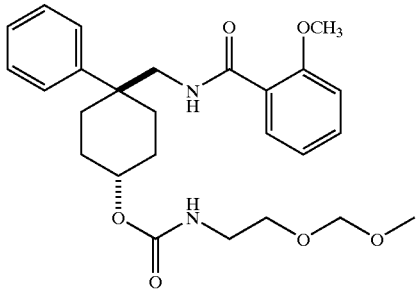

A solution of 42 mg (0.1 mmol) of trans 1-((N-2-hydroxyethyl)carbamoyloxy)-4-phenyl-4-(3-(2-methoxyphenyl)-3-oxo-2-azaprop-1-yl)cyclohexane (Example 32), 24 mg (0.3 mmol) of chloromethyl methyl ether and 64 mg (0.5 mmol) of N,N-diisopropylethylamine in 10 mL of dichloromethane was stirred at rt for 8 hr. The reaction mixture was concentrated and purified by chromatography (silica, dichloromethane:ethyl acetate. 2:1 to 1:1) to afford the title compound as a white solid.

$^1$H NMR (CDCl$_3$) δ 3.33 (s, 3H), 3.35 (m, 2H), 3.58–3.65 (m, 7H), 4.59 (s, 2H); Mass Spectrum (PB-NH3/CI): m/e 471 (M+1).

EXAMPLE 57 trans 1-(N-2-Aminoethylcarbamoyloxy)-4-phenyl-4-(3-(2-methoxyphenyl)-3-oxo-2-azaprop-1-yl)cyclohexane

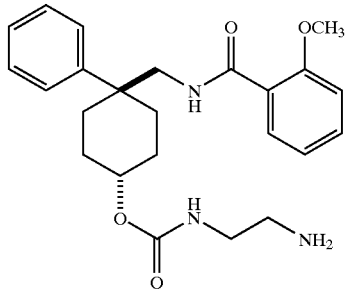

The title compound was prepared from trans 1-((4-nitrophenoxy)carbonyloxy)-4-phenyl-4-(3-(2-methoxyphenyl)-3-oxo-2-azaprop-1-yl)cyclohexane (Example 22) according to procedures described in Example 3.

$^1$H NMR (CDCl$_3$) δ 2.11 (m, 2H), 2.77 (s, 2H), 3.17 (m, 2H), 3.61–3.63 (m, 5H), 2.73 (brs, 1H), 5.13 (brs, 1H); Mass Spectrum (PB-NH3/CI): m/e 426 (M+1).

EXAMPLE 58 trans 1-(N-(2-Methylsulfonylamino)ethylcarbamoyloxy)-4-phenyl-4-(3-(2-methoxyphenyl)-3-oxo-2-azaprop-1-yl)cyclohexane

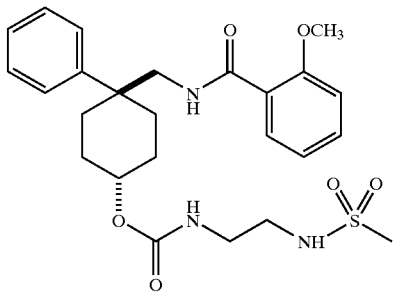

The title compound was prepared from trans 1-(N-2-aminoethylcarbamoyloxy)-4-phenyl-4-(3-(2-methoxyphenyl)-3-oxo-2-azaprop-1-yl)cyclohexane (Example 57) and methanesulfonyl chloride according to procedures described in Example 21.

$^1$H NMR (CDCl$_3$) δ 292 (s, 3H), 3.21–3.29 (m, 4H), 3.61–3.63 (m, 5H), 4.73 (brs, 1H), 5.13 (brs, 1H), 5.20 (brs, 1H); Mass Spectrum (PB-NH3/CI): m/e 504 (M+1).

EXAMPLE 59 trans 1-(N-(2-Propionylamino)ethyl)carbamoyloxy)-4-phenyl-4-(3-(2-methoxyphenyl)-3-oxo-2-azaprop-1-yl)cyclohexane

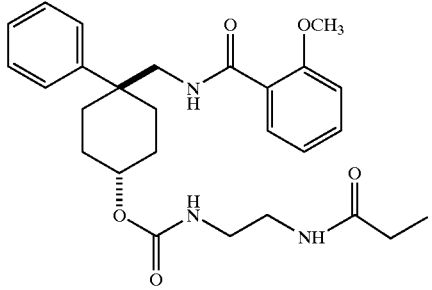

The title compound was prepared from trans 1-(N-2-aminoethylcarbamoyloxy)-4-phenyl-4-(3-(2-methoxyphenyl)-3-oxo-2-azaprop-1-yl)cyclohexane (Example 57) and propionyl chloride according to procedures described in Example 21.

$^1$H NMR (CDCl$_3$) δ 1.08 (t, 3H, J=7 Hz), 2.13 (m, 2H), 3.22–3.29 (m, 4H), 3.59–3.61 (m, 5H), 4.70 (brs, 1H), 5.13 (brs, 1H), 5.32 (brs, 1H); Mass Spectrum (PB-NH3/CI): m/e 482 (M+1).

EXAMPLE 60 trans 1-(N-(2-Methylcarbamoyl)ethyl)carbamoyloxy)-4-phenyl-4-(3-(2-methoxyphenyl)-3-oxo-2-azaprop-1-yl)cyclohexane

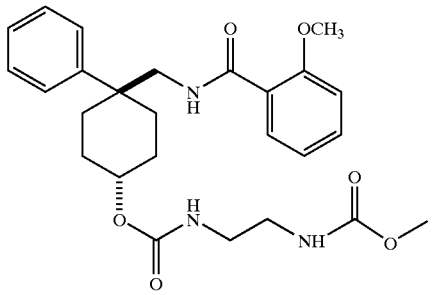

The title compound was prepared from trans 1-(N-2-aminoethylcarbamoyloxy)-4-phenyl-4-(3-(2-methoxyphenyl)-3-oxo-2-azaprop-1-yl)cyclohexane (Example 57) and methylchloroformate according to procedures described in Example 21.

$^1$H NMR (CDCl$_3$) δ 3.23 (m, 4H), 3.613 (m, 8H), 4.72 (brs, 1H), 5.15 (brs, 1H), 5.34 (brs, 1H); Mass Spectrum (PB-NH3/CI): m/e 484 (M+1).

EXAMPLE 61 trans 1-(N-(2-Isopropyloxycarbonylamino)ethylcarbamoyloxy)-4-phenyl-4-(3-(2-methoxyphenyl)-3-oxo-2-azaprop-1-yl)cyclohexane

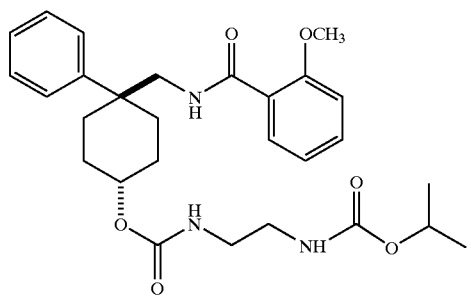

The title compound was prepared as described in Example 60.

$^1$H NMR (CDCl$_3$) δ 1.19 (d, 6H, J=6 Hz), 3.25 (m, 4H), 3.61 (m, 5H), 4.75 (brs, 1H), 4.86 (m, 1H), 4.98 (brs, 1H); Mass Spectrum (PB-NH3/CI): m/e 512 (M+1).

EXAMPLE 62 trans 1-(N-(2-N-Methylcarbamoyloxy)ethylcarbamoyloxy)-4-phenyl-4-(3-(2-methoxyphenyl)-3-oxo-2-azaprop-1-yl)cyclohexane

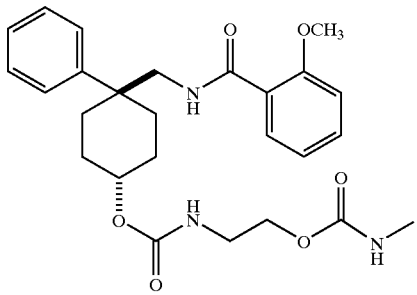

trans 1-((N-2-hydroxyethyl)carbamoyloxy)-4-phenyl-4-(3-(2-methoxyphenyl)-3-oxo-2-azaprop-1-yl)cyclohexane (Example 32) was converted to its 4-nitrophenylcarbonate intermediate as described in Example 2. This was then reacted with methylamine as described in Example 3.

$^1$H NMR (CDCl$_3$) δ 2.73 (s, 3H), 3.35 (m, 2H), 3.61 (m, 5H), 4.08 (m, 2H), 4.73 (brs, 1H), 4.82 (m, 1H), 4.98 (brs, 1H); Mass Spectrum (PB-NH3/CI): m/e 494 (M+1).

EXAMPLE 63 trans 1-N-(2-N-Allylcarbamoylethyl)carbamoyloxy-4-phenyl-4-(3-(2-methoxyphenyl)-3-oxo-2-azapropyl)cyclohexane

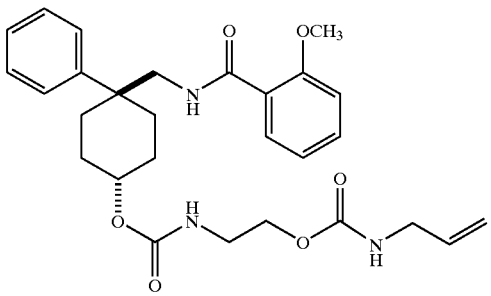

The title compound was prepared as described in Example 62.

$^1$H NMR (CDCl$_3$) δ 3.36 (m, 2H), 3.61 (s, 3H), 3.64 (d, 2H, J=6 Hz), 3.75 (m, 2H), 4.09 (m, 2H), 4.74 (brs, 1H), 4.97 (brs, 1H), 5.08 (d, 1H, J=10 Hz), 5.14 (d, 1H, J=17 Hz), 5.77 (m, 1H); Mass Spectrum (PB-NH3/CI): m/e 510 (M+1).

EXAMPLE 64 trans-1-(Methoxycarbonylmethoxycarbonyloxy)-4-phenyl-4-(3-(2-methoxyphenyl)-3-oxo-2-azapropy-1-l)cyclohexane

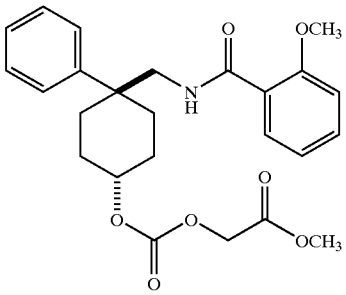

To a solution of 48 mg (0.095 mmol) of trans 1-((4-nitrophenoxy)carbonyloxy)-4-phenyl-4-(3-(2-methoxyphenyl)-3-oxo-2-azaprop-1-yl)cyclohexane in 5 mL of methyl glycolate was added 30mg of potassium carbonate at rt. The reaction mixture were stirred for 36 hr at 100° C. Then it was poured into 100 mL of ether. It was washed with water, dried over MgSO$_4$ and concentrated. The residue was purified by chromatography (silica, hexanes:ethyl acetate, 4:1 to 2:1) to afford the title compound as a white solid.

$^1$H NMR (CDCl$_3$) δ 3.61 (s, 3H), 3.66 (d, 2H, J=6 Hz), 3.76 (s, 3H), 4.59 (s, 2H), 4.79 (m, 1H); Mass Spectrum (PB-NH3/CI): m/e 456 (M+1).

EXAMPLE 65 trans-1-(Methoxycarbonyloxy)-4-phenyl-4-(3-(2-methoxyphenyl)-3-oxo-2-azaprop-1-yl)cyclohexane

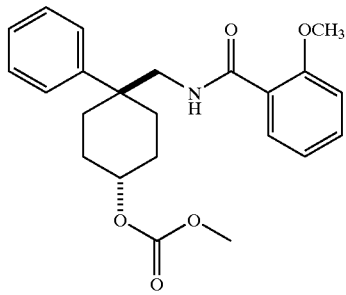

The title compound was prepared as described in Example 2 using methylchloroformate.

$^1$H NMR (CDCl$_3$) δ 3.60 (s, 3H), 3.65 (d, 2H, J=6 Hz), 3.72 (s, 3H), 4.74 (m, 1H); Mass Spectrum (PB-NH3/CI): m/e 398 (M+1).

EXAMPLE 66 cis 1-Amino-4-phenyl-4-(3-(2-methoxyphenyl)-3-oxo-2-azaprop-1-yl)cyclohexane

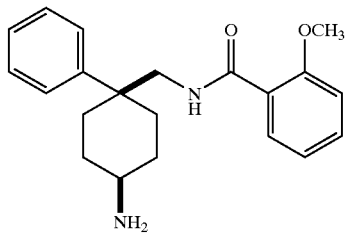

Step 1 trans-1-(Methylsulfonyloxy)-4-phenyl-4-(3-(2-methoxyphenyl)-3-oxo-2-azapropyl)cyclohexane To a solution of 1.07 g (3.16 mmol) of trans-1-hydroxy-4-phenyl-4-(3-(2-methoxyphenyl)-3-oxo-2-azaprop-1-yl)cyclohexane and 1.19 mL of triethylamine (7.9 mmol) in 50 mL of methylene chloride was added 0.49 mL (6.32 mmol) of methanesulfonyl chloride at 0° C. The reaction mixture was stirred at rt overnight and was poured into 100 mL of methylene chloride. It was washed with aq NaHCO$_3$, dried over MgSO$_4$ and concentrated. The residue was purified by chromatography (silica, hexanes:ethyl acetate, 4:1) to afford the title compound as a white solid.

Step 2 cis-1-Azido-4-phenyl-4-(3-(2-methoxyphenyl)-3-oxo-2-azaprop-1-yl)cyclohexane A mixture of 1.04 g (2.49 mmol) of trans-1-(methylsulfonyloxy)-4-phenyl-4-(3-(2-methoxyphenyl)-3-oxo-2-azaprop-1-yl)cyclohexane and 648 mg (9.96 mmol) of sodium azide in 50 mL of DMF was stirred at 100° C. for 5 hr. The reaction mixture was concentrated and the crude product was purified by chromatography (silica, hexanes:ethyl acetate, 6:1 to 5:1) to afford the title compound as a white solid.

Step 3 cis 1-Amino-4-phenyl-4-(3-(2-methoxyphenyl)-3-oxo-2-azaprop-1-yl)cyclohexane A mixture of 760 mg (2.09 mmol) of cis-1-azido-4-phenyl-4-(3-(2-methoxyphenyl)-3-oxo-2-azaprop-1-yl)cyclohexane, 700 mg of 5% Pd/C in 60 mL of ethyl acetate was hydrogenated in a pressurized bomb (45 psi) at rt overnight. The reaction mixture was filtered through a plug of celite, and the solids were washed with methylene chloride. The combined organic extracts were concentrated and the crude product was purified by chromatography (silica, CHCl$_3$/MeOH/NH$_3$, 100:8:4 to 100:10:5 (2M in MeOH)) to give the title compound as a whide solid.

$^1$H NMR (CDCl$_3$) δ 1.63–2.16 (m, 8H), 2.59 (brs, 2H), 3.82 (s, 3H), 3.52 (s, 3H), 3.89 (d, 2H, J=6 Hz); Mass Spectrum (PB-NH3/CI): m/e 339.2 (M+1).

EXAMPLE 67 cis 1-(4-Nitrophenyloxycarbonylamino)-4-phenyl-4-(3-(2-methoxyphenyl)-3-oxo-2-azaprop-1-yl)cyclohexane

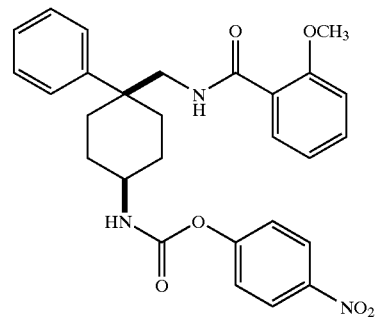

The title compound was prepared from cis 1-amino-4-phenyl-4-(3-(2-methoxyphenyl)-3-oxo-2-azaprop-1-yl)cyclohexane (Example 66) and 4-nitrophenyl chlorofomate as described in Example 2.

$^1$H NMR (CDCl$_3$) δ 1.79–2.15 (m, 8H), 3.54 (s, 3H), 3.67 (m, 1H), 3.89 (d, 2H, J=6 Hz) 7.33 (d, 2H, J=9 Hz), 8.26 (d, 2H, J=9 Hz); Mass Spectrum (PB-NH3/CI): m/e 504 (M+1).

EXAMPLE 68 cis 1-(N-Allyl-N-methylaminocarbonylamino)-4-phenyl-4-(3-(2-methoxyphen-1-yl)-3-oxo-2-azapropyl)cyclohexane

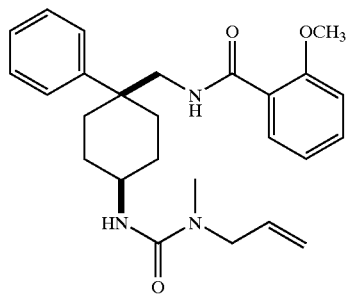

The title compound was prepared from cis 1-(4-nitrophenyloxycarbonylamino)-4-phenyl-4-(3-(2-methoxyphenyl)-3-oxo-2-azapropyl)cyclohexane (Example 67) and N-methylallylamine as described in Example 3.

$^1$H NMR (CDCl$_3$) δ 2.09 (s, 3H), 3.51 (s, 3H), 3.73 (m, 1H), 3.89 (d, 2H, J=7 Hz), 4.21 (d, 1H, J=7 Hz), 5.19 (m, 2H), 5.82 (m, 1H); Mass Spectrum (PB-NH3/CI): m/e 436 (M+1).

EXAMPLE 69 cis 1-(N-Allylaminocarbonylamino)-4-phenyl-4-(3-(2-methoxyphenyl)-3-oxo-2-azaprop-1-yl)cyclohexane

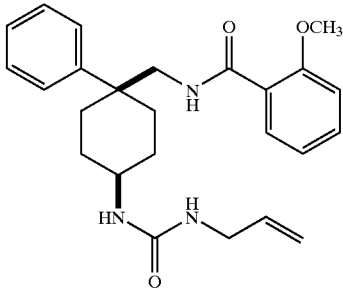

The title compound was prepared as described in Example 68 using allylamine.

$^1$H NMR (CDCl$_3$) δ 1.62–2.06 (m, 8H), 3.53 (s, 3H), 3.70 (brs, 1H), 6.86 (d, 2H, J=8 Hz), 8.20 (d, 2H, J=8 Hz); Mass Spectrum (PB-NH3/CI): m/e 422 (M+1).

EXAMPLE 70 cis 1-(Allyloxycarbonylamino)-4-phenyl-4-(3-(2-methoxyphenyl)-3-oxo-2-azaprop-1-yl)cyclohexane

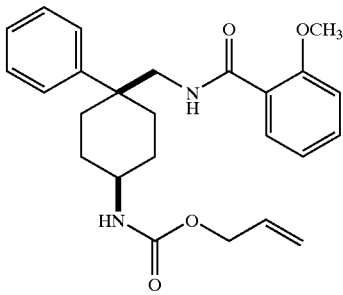

The title compound was prepared as described in Example 68 using allylalcohol.

$^1$H NMR (CDCl$_3$) δ 1.64–2.09 (m, 8H), 3.53 (s, 3H), 3.59 (brs, 1H), 3.85 (d, 2H, J=6 Hz), 6.86 (d, 2H, J=8 Hz), 8.20 (d, 2H, J=8 Hz); Mass Spectrum (PB-NH3/CI): m/e 423 (M+1).

EXAMPLE 71 cis 1-(But-2-en-1-oylamino)-4-phenyl-4-(3-(2-methoxyphenyl)-3-oxo-2-azaprop-1-yl)cyclohexane

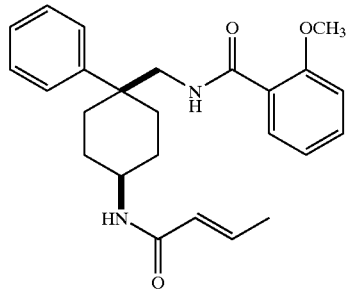

To a solution of cis-1-amino-4-phenyl-4-(3-(2-methoxyphenyl)-3-oxo-2-azaprop-1-yl)cyclohexane (Example 66) (36 mg, 0.11 mmol) in 5 mL of CH$_2$Cl$_2$ and Et$_3$N (32 mg, 0.32 mmol) was added trans-crotonyl chloride (22.2 mg, 0.21 mmol) and the mixture was stirred at rt overnight. It was poured into CH$_2$Cl$_2$ and washed once with NaHCO$_3$. The residue was purified by chromatography (silica, CH$_3$CN:BuOMe:hexanes (1:4:5 to 2:4:5) to give the title compound.

$^1$H NMR (CDCl$_3$) δ 1.87 (d, 2H, J=7 Hz), 3.53 (s, 3H), 5.80 (d, 1H, J=15 Hz), 6.86 (d, 2H, J=8 Hz), 8.21 (d, 2H, J=8 Hz); Mass Spectrum (PB-NH3/CI): m/e 407 (M+1).

Examples 72–76 were prepared as described in Example 71.

EXAMPLE 72 cis 1-(Benzoylamino)-4-phenyl-4-(3-(2-methoxyphenyl)-3-oxo-2-azaprop-1-yl)cyclohexane

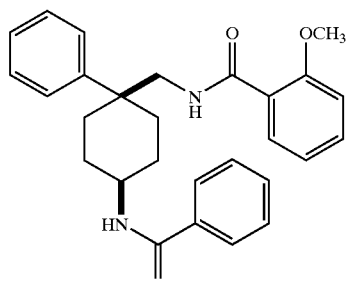

$^1$H NMR (CDCl$_3$) δ 3.53 (s, 3H), 3.93 (d, 2H, J=7 Hz), 4.08 (m, 1H); Mass Spectrum (PB-NH3/CI): m/e 443 (M+1).

EXAMPLE 73 cis 1-(Phenylacetylamino)-4-phenyl-4-(3-(2-methoxyphenyl)-3-oxo-2-azaprop-1-yl)cyclohexane

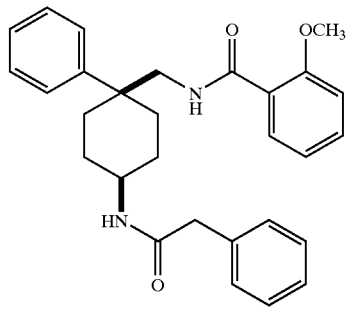

¹H NMR (CDCl₃) δ 3.49 (s, 3H), 3.57 (s, 3H,), 3.81 (d, 2H, J=7 Hz), 5.41 (d, 1H, J=7 Hz); Mass Spectrum (PB-NH3/CI): m/e 457 (M+1).

EXAMPLE 74 cis 1-(3-Phenylpropanoylamino)-4-phenyl-4-(3-(2-methoxyphenyl)-3-oxo-2-azaprop-1-yl)cyclohexane

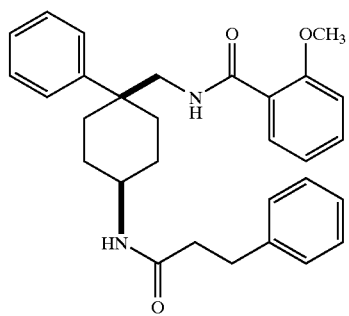

¹H NMR (CDCl₃) δ 2.47 (t, 2H, J=8 Hz), 2.98 (t, 2H, J=8 Hz), 3.52 (s, 3H), 3.84 (d, 2H, J=7 Hz), 5.44 (d, 1H, J=7 Hz); Mass Spectrum (PB-NH3/CI): m/e 471 (M+1).

EXAMPLE 75 cis 1-(Phenylsulfonylamino)-4-phenyl-4-(3-(2-methoxyphenyl)-3-oxo-2-azaprop-1-yl)cyclohexane

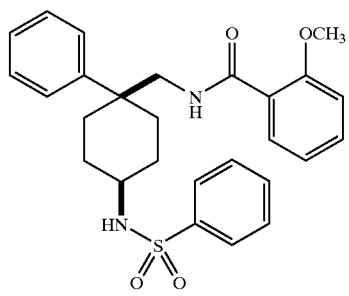

¹H NMR (CDCl₃) δ 1.64–2.04 (m, 8H), 3.28 (m, 1H), 3.52 (s, 3H), 3.78 (d, 2H, J=6 Hz), 4.68 (m, 1H); Mass Spectrum (PB-NH3/CI): m/e 479 (M+1).

EXAMPLE 76 cis 1-(Benzylsulfonylamino)-4-phenyl-4-(3-(2-methoxyphenyl)-3-oxo-2-azaprop-1-yl)cyclohexane

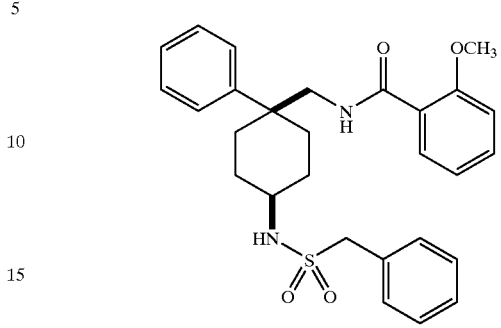

¹H NMR (CDCl₃) δ 3.16 (m, 1H), 3.52 (s, 3H), 3.79 (d, 2H, J=6 Hz), 4.27 (s, 2H); Mass Spectrum (PB-NH3/CI): m/e 492 (M+1).

EXAMPLE 77 trans-1-Amino-4-phenyl-4-(3-(2-methoxyphenyl)-3-oxo-2-azaprop-1-yl)cyclohexane

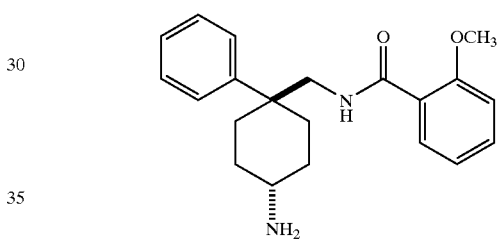

The title compound was prepared from cis 1-hydroxy-4-phenyl-4-(3-(2-methoxyphenyl)-3-oxo-2-azaprop-1-yl) cyclohexane as described in Example 66.

¹H NMR (CDCl₃) δ 1.21 (m, 2H), 1.63 (m, 2H), 1.83 (m, 2H), 2.42 (m, 2H), 3.16 (brs, 2H), 3.56 (d, 2H, J=7 Hz), 3.64 (s, 3H); Mass Spectrum (PB-NH3/CI): m/e 339 (M+1).

EXAMPLE 78 trans-1-(4-Nitrophenoxycarbonylamino)-4-phenyl-4-(3-(2-methoxyphenyl) 3-oxo-2-azaprop-1-yl) cyclohexane

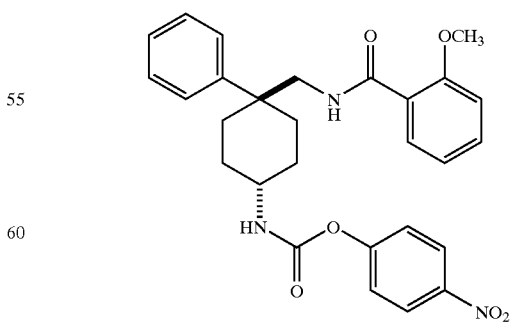

The title compound was prepared from trans-1-amino-4-phenyl-4-(3-(2-methoxyphenyl)-3-oxo-2-azaprop-1-yl)

cyclohexane (Example 77) and 4-nitrophenylchlorofomate as described in Example 2.

$^1$H NMR (CDCl$_3$) δ 1.30 (m, 2H), 1.76 (m, 2H), 2.03 (m, 2H), 2.45 (m, 2H), 3.60 (d, 2H, J=6 Hz), 3.68 (s, 3H), 4.85 (m, 1H), 6.90 (d, 2H, J=9 Hz), Mass Spectrum (PB-NH3/CI): m/e 504 (M+1).

EXAMPLE 79 trans-1-(Methoxycarbonylamino)-4-phenyl-4-(3-(2-methoxyphenyl)-3-oxo-2-azapropyl)cyclohexane

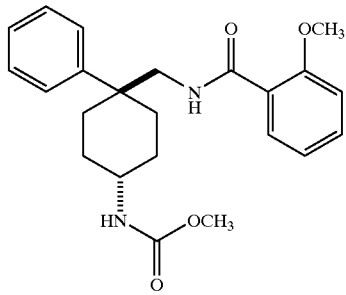

The title compound was prepared from trans-1-(4-nitrophenoxycarbonylamino)-4-phenyl-4-(3-(2-methoxyphenyl)-3-oxo-2-azaprop-1-yl)cyclohexane (Example 78) as described in Example 2 using methylchloroformate.

$^1$H NMR (CDCl$_3$) δ 3.55–3.58 (m, 5H), 3.65 (s, 3H); Mass Spectrum (PB-NH3/CI): m/e 397 (M+1).

EXAMPLE 80 trans-1-(Methylthiocarbonylamino)-4-phenyl-4-(3-(2-methoxyphenyl)-3-oxo-2-azaprop-1-yl)cyclohexane

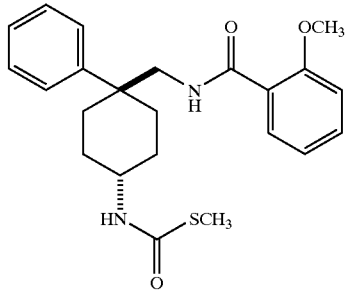

The title compound was prepared as described in Example 2 using methylchlorothioformate.

$^1$H NMR (CDCl$_3$) δ 2.27 (s, 3H), 3.54 (d, 2H, J=7 Hz), 3.65 (s, 3H), 3.86 (brs, 1H); Mass Spectrum (PB-NH3/CI): m/e 413 (M+1).

EXAMPLE 81 trans-1-(N-Allylaminocarbonylamino)-4-phenyl-4-(3-(2-methoxyphenyl)-3-oxo-2-azaprop-1-yl)cyclohexane

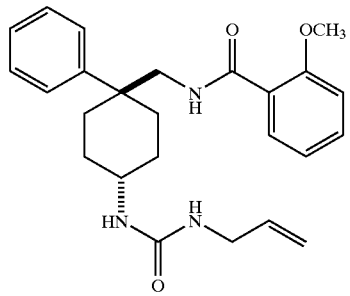

The title compound was prepared from trans-1-(4-nitrophenyloxycarbonylamino)-4-phenyl-4-(3-(2-methoxyphenyl)-3-oxo-2-azaprop-1-yl)cyclohexane (Example 78) as described in Example 68.

$^1$H NMR (CDCl$_3$) δ 1.15 (m, 2H), 1.72 (m, 2H), 1.93 (m, 2H), 2.38 (m, 2H), 3.56 (d, 2H, J=7 Hz), 3.68 (s, 3H), 3.73 (d, 2H, J=7 Hz), 4.09 (brs, 1H), 4.280 (brs, 1H), 5.09 (d, 1H, J=9 Hz), 5.14 (d, 1H, J=17 Hz), 5.81 (m, 1H); Mass Spectrum (PB-NH3/CI): m/e 422 (M+1).

EXAMPLE 82 trans-1-(Allyloxycarbonylamino)-4-phenyl-4-(3-(2-methoxyphenyl)-3-oxo-2-azaprop-1-yl)cyclohexane

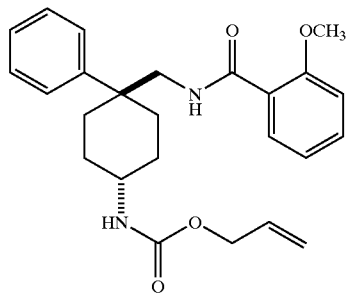

The title compound was prepared as in Example 81 using allyl alcohol.

$^1$H NMR (CDCl$_3$) δ 1.19 (m, 2H), 1.72 (m, 2H), 1.93 (m, 2H), 2.40 (m, 2H), 3.58 (d, 2H, J=7 Hz), 3.67 (s, 3H), 4,52 (brs, 2H), 5.17 (d, 1H, J=10 Hz), 5.24 (d, 1H, J=16 Hz), 5.89 (m, 1H); Mass Spectrum (PB-NH3/CI): m/e 423 (M+1).

The following Examples 83 to 94 were prepared from trans-1-amino-4-phenyl-4-(3-(2-methoxyphenyl)-3-oxo-2-azaprop-1-yl)cyclohexane as described in Example 71.

EXAMPLE 83 trans-1-(Acetylamino)-4-phenyl-4-(3-(2-methoxyphenyl)-3-oxo-2-azaprop-1-yl)cyclohexane

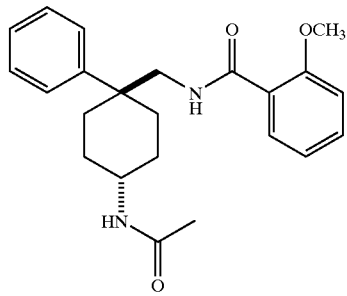

$^1$H NMR (CDCl$_3$) δ 1.83 (s, 3H), 3.52 (d, 2H, J=6 Hz), 3.66 (s, 3H), 3.83 (m, 1H), 5.44 (d, 1H, J=7 Hz); Mass Spectrum (PB-NH3/CI): m/e 381 (M+1).

EXAMPLE 84 trans-1-(n-Propanoylamino)-4-phenyl-4-(3-(2-methoxyphenyl)-3-oxo-2-azaprop-1-yl)cyclohexane

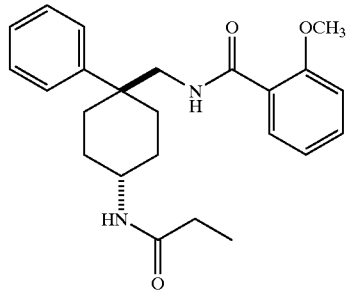

$^1$H NMR (CDCl$_3$) δ 1.05 (t, 3H, J=7 Hz), 2.05 (q, 2H, J$_1$=15 Hz, J$_2$=7 Hz), 3.52 (d, 2H, J=6 Hz), 3.66 (s, 3H), 3.84 (m, 1H), 5.34 (d, 1H, J=7 Hz); Mass Spectrum (PB-NH3/CI): m/e 395 (M+1).

EXAMPLE 85 trans-1-(n-Butanoylamino)-4-phenyl-4-(3-(2-methoxyphenyl)-3-oxo-2-azapropyl)cyclohexane

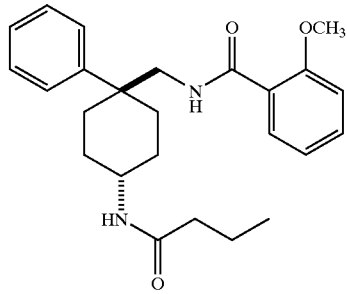

$^1$H NMR (CDCl$_3$) δ 0.85 (t, 3H, J=7 Hz), 1.55 (m, 2H), 2.00 (t, 2H, J=7 Hz), 3.52 (d, 2H, J=6 Hz), 3.66 (s, 3H), 3.85 (m, 1H), 5.36 (d, 1H, J=7 Hz); Mass Spectrum (PB-NH3/CI): m/e 409 (M+1).

EXAMPLES 86 AND 87 trans-1-(3-Methylbut-2-enoylamino)-4-phenyl-4-(3-(2-methoxyphenyl)-3-oxo-2-azaprop-1-yl)cyclohexane and trans-1-(3-Methylbut-3-enoylamino)-4-phenyl-4-(3-(2-methoxyphenyl)-3-oxo-2-azaprop-1-yl)cyclohexane

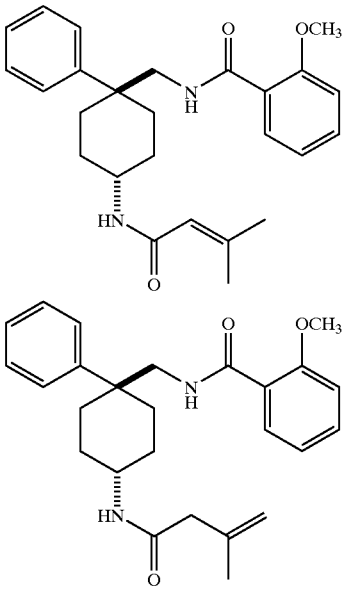

Both Examples were obtained upon acylation with 3-methylbut-2-enoylchloride.

For trans-1-(3-methylbut-2-enoylamino)-4-phenyl-4-(3-(2-methoxyphenyl)-3-oxo-2-azaprop-1-yl)cyclohexane $^1$H NMR (CDCl$_3$) δ 1.76 (s, 3H), 2.09 (s, 3H), 3.54 (d, 2H, J=6 Hz), 3.66 (s, 3H), 3.89 (m, 1H), 5.21 (d, 1H, J=8 Hz); Mass Spectrum (PB-NH3/CI): m/e 421 (M+1).

For trans-1-(3-methylbut-3-enoylamino)-4-phenyl-4-(3-(2-methoxyphenyl)-3-oxo-2-azaprop-1-yl)cyclohexane. $^1$H NMR (CDCl$_3$) δ 1.70 (s, 3H), 2.84 (s, 3H), 3.3.54 (d, 2H, J=6 Hz), 3.67 (s, 3H), 4.78 (s, 1H), 4.87 (s, 1H), 5.49 (d, 1H, J=8 Hz); Mass Spectrum (PB-NH3/CI): m/e 421 (M+1).

EXAMPLE 88 trans-1-(But-2-enoylamino)-4-phenyl-4-(3-(2-methoxyphenyl)-3-oxo-2-azaprop-1-yl)cyclohexane

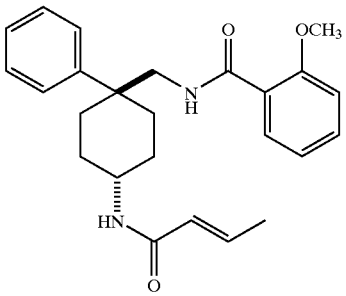

$^1$H NMR (CDCl$_3$) δ 1.76 (d, 3H, J=6 Hz), 3.52 (d, 2H, J6=Hz), 3.67 (s, 3H), 3.91 (m, 1H), 5.64 (d, 1H, J=5 Hz); Mass Spectrum (PB-NH3/CI): m/e 407 (M+1).

EXAMPLE 89 trans-1-(Benzoylamino)-4-phenyl-4-(3-(2-methoxyphenyl)-3-oxo-2-azaprop-1-yl)cyclohexane

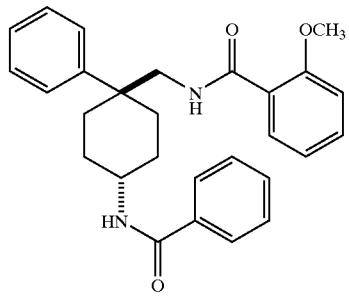

$^1$H NMR (CDCl$_3$) δ 3.59 (d, 2H, J=6 Hz), 3.69 (s, 3H), 4.10 (m, 1H); Mass Spectrum (PB-NH3/CI): m/e 443 (M+1).

EXAMPLE 90 trans-1-(Phenylacetylamino)-4-phenyl-4-(3-(2-methoxyphenyl)-3-oxo-2-azaprop-1-yl)cyclohexane

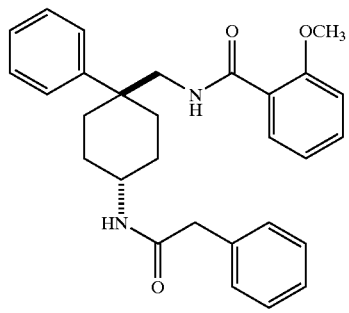

$^1$H NMR (CDCl$_3$) δ 3.49 (s, 2H), 3.54 (d, 2H, J=6 Hz), 3.67 (s, 3H), 3.88 (m, 1H); Mass Spectrum (PB-NH3/CI): m/e 457 (M+1).

EXAMPLE 91 trans-1-(3-Phenyl-n-propanoylamino)-4-phenyl-4-(3-(2-methoxyphenyl)-3-oxo-2-azaprop-1-yl)cyclohexane

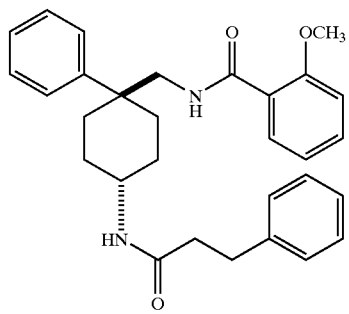

$^1$H NMR (CDCl$_3$) δ 2.34 (t, 2H, J=7 Hz)), 2.90 (t, 2H, J=7 Hz), 3.55 (d, 2H, J=7 Hz), 3.68 (s, 3H), 3.85 (m, 1H); Mass Spectrum (PB-NH3/CI): m/e 471 (M+1).

EXAMPLE 92 trans-1-(2-Bromobenzoylamino)-4-phenyl-4-(3-(2-methoxyphenyl)-3-oxo-2-azaprop-1-yl)cyclohexane

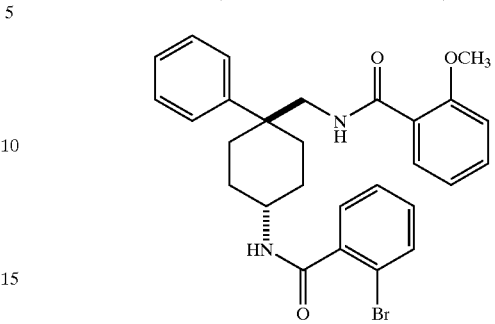

$^1$H NMR (CDCl$_3$) δ 3.59 (d, 2H, J=6 Hz), 3.68 (s, 3H), 4.11 (m, 1H), 5.70 (d, 1H, J=7 Hz); Mass Spectrum (PB-NH3/CI): m/e 521 (M+1).

EXAMPLE 93 trans-1-(3-Bromobenzoylamino)-4-phenyl-4-(3-(2-methoxyphenyl)-3-oxo-2-azaprop-1-yl)cyclohexane

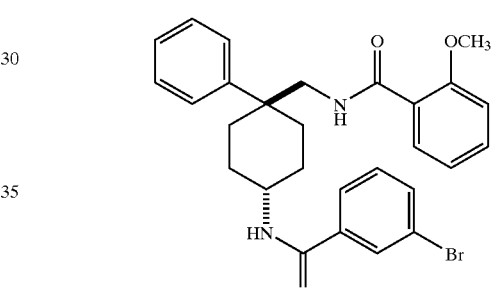

$^1$H NMR (CDCl$_3$) δ 3.55 (d, 2H, J=6 Hz), 3.68 (s, 3H), 4.05 (m, 1H), 5.98 (d, 1H, J=7 Hz); Mass Spectrum (PB-NH3/CI): m/e 521 (M+1).

EXAMPLE 94 trans-1-(4-Bromobenzoylamino)-4-phenyl-4-(3-(2-methoxyphenyl)-3-oxo-2-azaprop-1-yl)cyclohexane

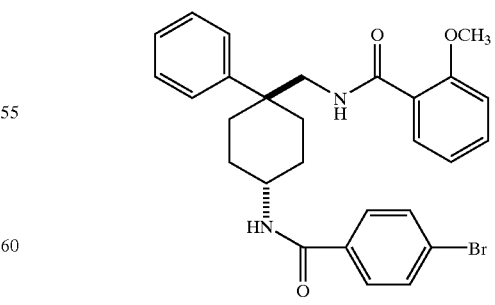

$^1$H NMR (CDCl$_3$) δ 3.54 (d, 2H, J=6 Hz), 3.68 (s, 3H), 4.03 (m, 1H), 6.00 (d, 1H, J=7 Hz); Mass Spectrum (PB-NH3/CI): m/e 521 (M+1).

EXAMPLE 95

4-Phenyl-4-(3-(2,3-dihydrobenzofuran-7-yl)-3-oxo-2-azaprop-1-yl)cyclohexanone

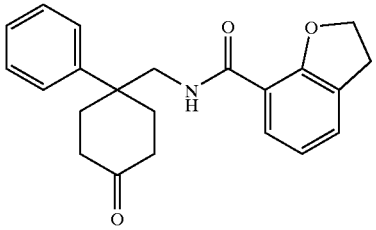

A solution of 1.85 g (11.3 mmol) of 4-aminomethyl-4-phenylcyclohexanone ethyleneglycol ketal (Example 1, Step 2), 4.33 g (22.6 mmol) of 1-(3-dimethylaminopropyl)-3-ethylcarbodiimide hydrochloride and 2.76 g (22.6 mmol) of 4-dimethylaminopyridine in 40 mL of methylene chloride was stirred at rt for 30 min. Then 3.07 g (12.4 mmol) of 2,3-dihydrobenzofuran-7-carboxylic acid was added and the reaction mixture was stirred at rt for 3 hr. It was then poured into 200 mL of ether. It was washed with 1N HCl (30 mL), dried over $MgSO_4$ and concentrated. Then 60 mL of THF and 20 mL of 2N HCl was added to the above residue and the reaction mixture were stirred at 40° C. for 3 hr. The reaction mixture was poured into 200 mL of ether. The organic layer was washed with aq $NaHCO_3$, dried over $MgSO_4$ and concentrated. The residue was purified by chromatography (silica, hexanes:ethyl acetate, 3:1 to 2:1) to afford the title compound as a white solid.

$^1$H NMR (CDCl$_3$) δ 2.10 (m, 2H), 2.33 (m, 2H), 2.45 (m, 2H), 2.56 (m, 2H), 3.22 (t, 2H, J=8 Hz), 3.70 (d, 2H, J=6 Hz), 4.52 (t, 2H, J=8 Hz), 6.95 (t, 1H, J=8 Hz), 7.27–7.52 (m, 6H), 7.88 (d, 1H, J=8 Hz); Mass Spectrum (PB-NH3/CI): m/e 350 (M+1).

EXAMPLE 96 trans and cis 1-Hydroxy-4-phenyl-4-(3-(2,3-dihydrobenzofuran-7-yl)-3-oxo-2-azaprop-1-yl)cyclohexane

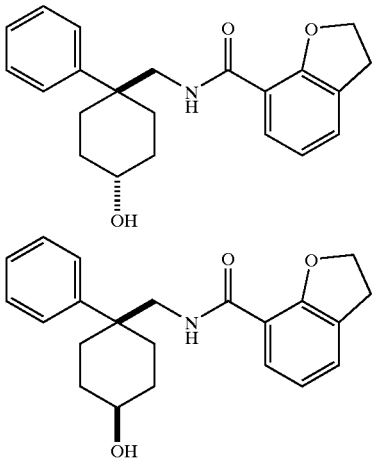

The title compounds were prepared according to procedures described in Example 1, Step 4.

For trans 1-hydroxy-4-phenyl-4-(3-(2,3-dihydrobenzofuran-7-yl)-3-oxo-2-azaprop-1-yl)cyclohexane $^1$H NMR (CDCl$_3$) δ 1.35 (m, 2H), 1.64 (m, 2H), 1.88 (m, 2H), 2.38 (m, 2H), 3.21 (t, 2H, J=8 Hz), 3.54 (d, 2H, J=6 Hz), 3.79 (m, 1H), 4.50 (t, 2H, J=8 Hz), 6.92 (t, 1H, J=8 Hz), 7.25–7.44 (m, 6H), 7.88 (d, 1H, J=8 Hz); Mass Spectrum (PB-NH3/CI): m/e 352 (M+1).

For cis 1-hydroxy-4-phenyl-4-(3-(2,3-dihydrobenzofuran-7-yl)-3-oxo-2-azapropyl)cyclohexane, $^1$H NMR (CDCl$_3$) δ 1.76 (m, 4H), 1.89 (m, 2H), 2.14 (m, 2H), 3.16 (t, 2H, J=8 Hz), 3.71 (d, 2H, J=6 Hz), 3.76 (m, 1H), 4.43 (t, 2H, J=8 Hz), 6.92 (t, 1H, J=8 Hz), 7.23–7.44 (m, 6H), 7.86 (d, 1H, J=8 Hz); Mass Spectrum (PB-NH3/CI): m/e 352 (M+1).

EXAMPLE 97 cis 1-Hydroxy-4-phenyl-4-(3-(benzofuran-7-yl)-3-oxo-2-azaprop-1-yl)cyclohexane

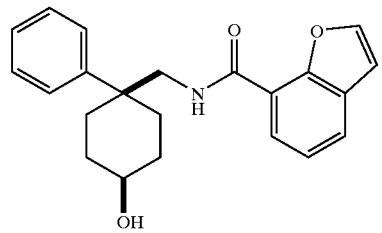

A mixture of 810 mg (2.31 mmol) of cis 1-hydroxy-4-phenyl-4-(3-(2,3-dihydrobenzofuran-7-yl)-3-oxo-2-azaprop-1-yl)cyclohexane, 800 mg of 5% Pd/C in 50 mL of 1-propanol was dehydrogenated in a pressurized bomb (45 psi) at rt overnight. The reaction mixture was filtered through a plug of celite, and the solids was washed with methylene chloride. The combined organic extracts were concentrated and the crude product was purified by chromatography (silica, CH$_2$Cl$_2$:CH$_3$COOCH$_2$CH$_3$) to give the title compound as a white solid.

$^1$H NMR (CDCl$_3$) δ 1.76 (m, 4H), 1.96 (m, 2H), 2.19 (m, 2H), 3.79 (m, 1H), 3.82 (d, 2H, J=6 Hz); Mass Spectrum (PB-NH3/CI): m/e 350 (M+1).

EXAMPLE 98 trans 1-Hydroxy-4-phenyl-4-(3-(benzofuran-7-yl)-3-oxo-2-azaprop-1-yl)cyclohexane

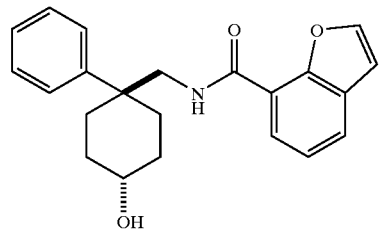

The title compound was prepared from trans 1-hydroxy-4-phenyl-4-(3-(2,3-dihydrobenzofuran-7-yl)-3-oxo-2-azaprop-1-yl)cyclohexane as described in Example 97.

$^1$H NMR (CDCl$_3$) δ 1.36 (m, 2H), 1.70 (m, 2H), 1.91 (m, 2H), 2.44 (m, 2H), 3.66 (d, 2H, J=6 Hz), 3.79 (m, 1H); Mass Spectrum (PB-NH3/CI): m/e 350 (M+1).

The following Examples 99–102 were prepared from cis 1-hydroxy-4-phenyl-4-(3-(benzofuran-7-yl)-3-oxo-2- azaprop-1-yl)cyclohexane (Example 97) via its 4-nitrophenylcarbonate intermediate as described in Examples 2 and 3.

EXAMPLE 99 cis-1-(N-Methylcarbamoyloxy)-4-phenyl-4-(3-(benzofuran-7-yl)-3-oxo-2-azaprop-1-yl)cyclohexane

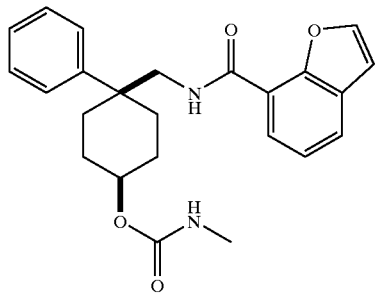

$^1$H NMR (CDCl$_3$) δ 1.70 (m, 2H), 1.83 (m, 2H), 2.07 (m, 4H), 2.80 (d, 2H, J=6 Hz), 3.76 (d, 2H, J=6 Hz), 4.77 (brs, 1H), 4.81 (brs, 1H); Mass Spectrum (PB-NH3/CI): m/e 407 (M+1).

EXAMPLE 100 cis-1-(N-Ethylcarbamoyloxy)-4-phenyl-4-(3-(benzofuran-7-yl)-3-oxo-2-azaprop-1-yl)cyclohexane

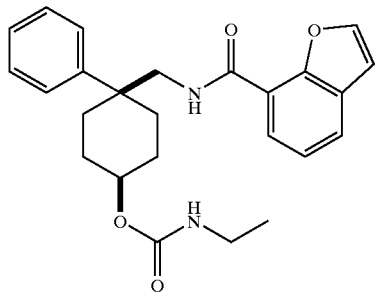

$^1$H NMR (CDCl$_3$) δ 1.16 (t, 3H, J=6 Hz), 1.70 (m, 2H), 1.84 (m, 2H), 2.07 (m, 4H), 3.23 (m, 2H), 3.76 (d, 2H, J=6 Hz), 4.77 (brs, 2H); Mass Spectrum (PB-NH3/CI): m/e 421 (M+1).

EXAMPLE 101 cis-1-(N-n-Propylcarbamoyloxy)-4-phenyl-4-(3-(benzofuran-7-yl)-3-oxo-2-azaprop-1-yl)cyclohexane

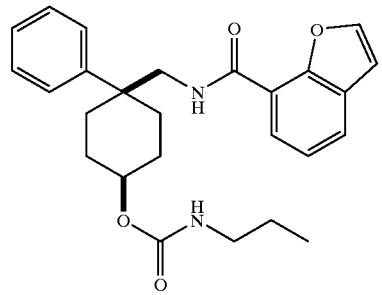

$^1$H NMR (CDCl$_3$) δ 0.941 (t, 3H, J=6 Hz), 1.55 (m, 2H), 1.70 (m, 2H), 1.84 (m, 2H), 2.07 (m, 4H), 3.14 (m, 2H), 3.76 (d, 2H, J=6 Hz), 4.76 (brs, 1H), 4.79 (brs, 1H); Mass Spectrum (PB-NH3/CI): m/e 435 (M+1).

EXAMPLE 102 cis-1-(N-Allylcarbamoyl)oxy-4-phenyl-4-(3-(benzofuran-7-yl)-3-oxo-2-azapropyl)cyclohexane

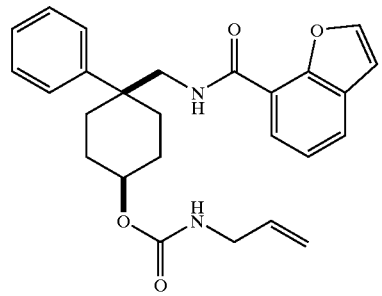

$^1$H NMR (CDCl$_3$) δ 1.72 (m, 2H), 1.86 (m, 2H), 2.08 (m, 4H), 3.76 (d, 2H, J=6 Hz), 3.82 (m, 2H), 4.78 (brs, 1H), 4.89 (brs, 1H), 5.13 (d, 1H, J=10 Hz), 5.21 (d, 1H, J=17 Hz), 5.86 (m, 1H); Mass Spectrum (PB-NH3/CI): m/e 433.2 (M+1).

The following Examples 103–105 were prepared from trans 1-hydroxy-4-phenyl-4-(3-(benzofuran-7-yl)-3-oxo-2-azaprop-1-yl)cyclohexane (Example 98) via its 4-nitrophenylcarbonate intermediate as described in Examples 2 and 3.

EXAMPLE 103 trans-1-(N-Methylcarbamoyloxy)-4-phenyl-4-(3-(benzofuran-7-yl)-3-oxo-2-azaprop-1-yl)cyclohexane

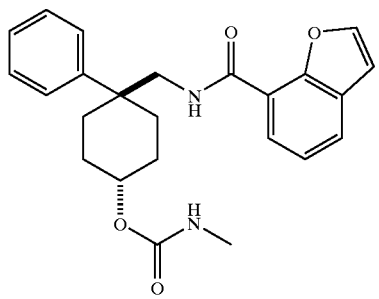

$^1$H NMR (CDCl$_3$) δ 1.47 (m, 2H), 1.79 (m, 2H), 1.94 (m, 2H), 2.37 (m, 2H), 2.73 (d, 3H, J=4 Hz), 3.67 (d, 2H, J=6 Hz), 4.53 (brs, 1H), 4.77 (brs, 1H); Mass Spectrum (PB-NH3/CI): m/e 407.2 (M+1).

EXAMPLE 104 trans-1-(N-Ethylcarbamoyloxy)-4-phenyl-4-(3-(benzofuran-7-yl)-3-oxo-2-azaprop-1-yl)cyclohexane

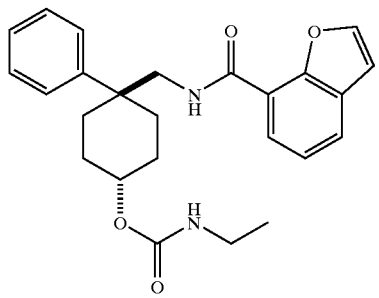

$^1$H NMR (CDCl$_3$) δ 1.08 (t, 3H, J=6 Hz), 1.48 (m, 2H), 1.79 (m, 2H), 1.95 (m, 2H), 2.37 (m, H), 3.16 (m, 2H), 3.67 (d, 2H, J=6 Hz), 4.58 (brs, 1H), 4.76 (brs, 1H); Mass Spectrum (PB-NH3/CI): m/e 421.2 (M+1).

EXAMPLE 105 trans-1-(N-Ethylcarbamoyloxy)-4-phenyl-4-(3-(benzofuran-7-yl)-3-oxo-2-azaprop-1-yl)cyclohexane

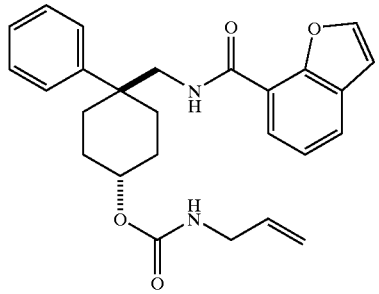

$^1$H NMR (CDCl$_3$) δ 1.48 (m, 2H), 1.79 (m, 2H), 1.95 (m, 2H), 2.37 (m, 2H), 3.67 (d, 2H, J=6 Hz), 3.75 (m, 2H), 4.71 (brs, 1H), 4.78 (brs, 1H), 5.06 (d, 1H, J=10 Hz), 5.11 (d, 1H, J=17 Hz), 5.78 (m, 1H); Mass Spectrum (PB-NH3/CI): m/e 433.2 (M+1).

The following Examples 106–111 were prepared from trans or cis 1-hydroxy-4-phenyl-4-(3-(2,3-dihydrobenzofuran-7-yl)-3-oxo-2-azaprop-1-yl)cyclohexane (Example 96) via its 4-nitrophenylcarbonate intermediate as described in Examples 2 and 3.

EXAMPLE 106 cis 1-(N-Methylcarbamoyloxy)-4-phenyl-4-(3-(2,3-dihydrobenzofuran-7-yl)-3-oxo-2-azaprop-1-yl)cyclohexane

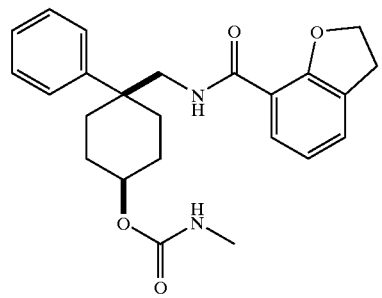

$^1$H NMR (CDCl$_3$) δ 1.67 (m, 2H), 1.80 (m, 2H), 2.00 (m, 4H), 2.78 (d, 3H, J=4 Hz), 3.16 (t, 2H, J=9 Hz), 3.64 (d, 2H, J=6 Hz), 4.43 (t, 2H, J=6 Hz), 4.73 (brs, 1H), 4.87 (brs, 1H); Mass Spectrum (PB-NH3/CI): m/e 408.2 (M+1).

EXAMPLE 107 cis 1-(N-i-Propylcarbamoyloxy)-4-phenyl-4-(3-(2,3-dihydrobenzofuran-7-yl)-3-oxo-2-azaprop-1-yl)cyclohexane

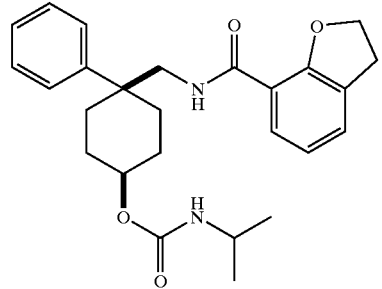

$^1$H NMR (CDCl$_3$) δ 1.15 (d, 6H, J=6 Hz), 1.67 (m, 2H), 1.80 (m, 2H), 2.00 (m, 4H), 3.16 (t, 2H, J=9 Hz), 3.64 (d, 2H, J=6 Hz), 4.41 (t, 2H, J=6 Hz), 4.65 (brs, 1H), 4.72 (brs, 1H); Mass Spectrum (PB-NH3/CI): m/e 437.2 (M+1).

EXAMPLE 108 cis 1-(N-Allylcarbamoyloxy)-4-phenyl-4-(3-(2,3-dihydrobenzofuran-7-yl)-3-oxo-2-azaprop-1-yl)cyclohexane

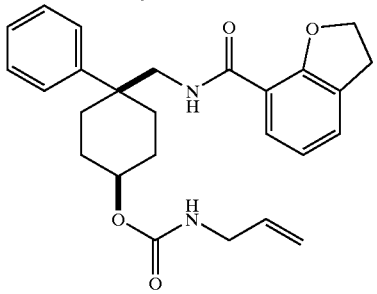

$^1$H NMR (CDCl$_3$) δ 1.15 (d, 6H, J=6 Hz), 1.67 (m, 2H), 1.80 (m, 2H), 2.00 (m, 4H), 3.16 (t, 2H, J=9 Hz), 3.64 (d, 2H, J=6 Hz), 3.40 (m, 2H), 4.43 (t, 2H, J=6 Hz), 4.75 (brs, 1H), 5.02 (brs, 1H), 5.13 (d, 1H, J=10 Hz), 5.18 (d, 1H, J=20 Hz); Mass Spectrum (PB-NH3/CI): m/e 435.2 (M+1).

EXAMPLE 109 trans 1-(N-i-Propylcarbamoyloxy)-4-phenyl-4-(3-(2,3-dihydrobenzofuran-7-yl)-3-oxo-2-azaprop-1-yl)cyclohexane

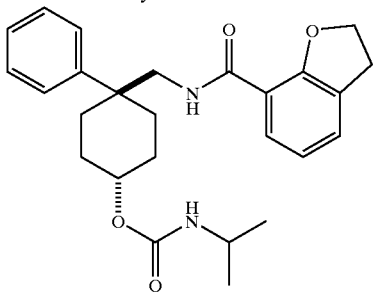

$^1$H NMR (CDCl$_3$) δ 1.08 (d, 6H, J=6 Hz), 1.46 (m, 2H), 1.74 (m, 2H), 1.95 (m, 2H), 2.32 (m, 2H), 3.18 (t, 2H, J=9 Hz), 3.57 (d, 2H, J=6 Hz), 4.48 (t, 2H, J=6 Hz), 4.72 (brs, 1H); Mass Spectrum (PB-NH3/CI): m/e 437.2 (M+1).

EXAMPLE 110 trans 1-(N-n-Butylcarbamoyloxy)-4-phenyl-4-(3-(2,3-dihydrobenzofuran-7-yl)-3-oxo-2-azaprop-1-yl)cyclohexane

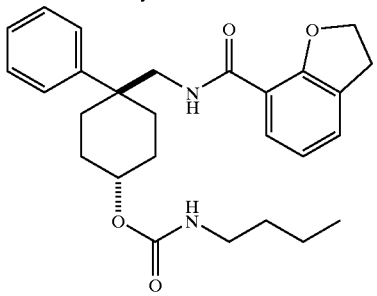

$^1$H NMR (CDCl$_3$) δ 0.84 (t, 3H, J=7 Hz), 1.28 (m, 2H), 1.42 (m, 2H), 1.71 (m, 2H), 1.91 (m, 2H), 2.32 (m, 2H), 3.11 (m, 2H), 3.18 (t, 2H, J=9 Hz), 3.55 (d, 2H, J=6 Hz), 4.41 (t, 2H, J=6 Hz), 4.72 (brs, 1H); Mass Spectrum (PB-NH3/CI): m/e 451.2 (M+1).

EXAMPLE 111 trans 1-(N-Allylcarbamoyloxy)-4-phenyl-4-(3-(2,3-dihydrobenzofuran-7-yl)-3-oxo-2-azaprop-1-yl)cyclohexane

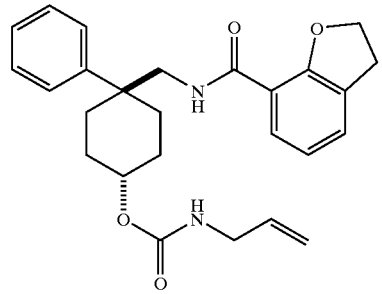

$^1$H NMR (CDCl$_3$) δ 1.45 (m, 2H), 1.71 (m, 2H), 1.92 (m, 2H), 2.32 (m, 2H), 3.18 (t, 2H, J=9 Hz), 3.56 (d, 2H, J=6 Hz), 4.41 (t, 2H, J=6 Hz), 4.72 (brs, 1H), 5.06 (d, 1H, J=10 Hz), 5.11 (d, 1H, J=17 Hz), 5.79 (m, 1H); Mass Spectrum (PB-NH3/CI): m/e 435.2 (M+1).

EXAMPLE 112 trans 1-Azido-4-phenyl-4-(3-(benzofuran-7-yl)-3-oxo-2-azaprop-1-yl)cyclohexane

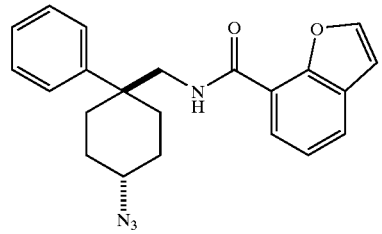

The title compound was prepared from cis 1-hydroxy-4-phenyl-4-(3-(benzofuran-7-yl)-3-oxo-2-azaprop-1-yl)cyclohexane (Example 97) according to procedures described in Examples 66 and 77.

$^1$H NMR (CDCl$_3$) δ 1.79 (m, 2H), 2.07 (m, 2H), 2.15 (m, 2H), 3.76 (d, 2H, J=6 Hz), 4.85 (m, 1H); Mass Spectrum (PB-NH3/CI): m/e 375 (M+1).

EXAMPLE 113 trans-1-Amino-4-phenyl-4-(3-(benzofuran-7-yl)-3-oxo-2-azaprop-1-yl)cyclohexane and trans-1-Amino-4-phenyl-4-(3-(2,3-dihydrobenzofuran-7-yl)-3-oxo-2-azaprop-1-yl)cyclohexane

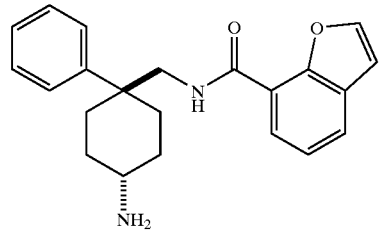

-continued

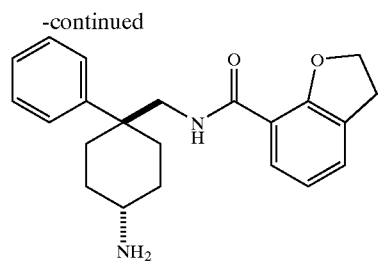

The title compounds were prepared as described in Example 66, Step 3. Over-hydrogenation provided the dehydro-derivative in a ratio of 1:9.

For trans-1-amino-4-phenyl-4-(3-(benzofuran-7-yl)-3-oxo-2-azaprop-1-yl)cyclohexane $^1$H NMR (CDCl$_3$) δ δ 1.16 (m, 2H), 1.62 (m, 2H), 1.78 (m, 2H), 2.43 (m, 2H), 3.62 (d, 2H, J=6 Hz), 7.71 (d, 1H, J=8 Hz), 8.09 (d, 1H, J=8 Hz), Mass Spectrum (PB-NH3/CI): m/e 349 (M+1).

For trans-1-amino-4-phenyl-4-(3-(2,3-dihydrobenzofuran-7-yl)-3-oxo-2-azaprop-1-yl)cyclohexane $^1$H NMR (CDCl$_3$) δ 1.16 (m, 2H), 1.59 (m, 2H), 1.77 (m, 2H), 2.41 (m, 2H), 3.21 (t, 2H, J=7 Hz), 3.52 (d, 2H, J=6 Hz), 4.52 (t, 2H, J=7 Hz); Mass Spectrum (PB-NH3/CI): m/e 351 (M+1).

EXAMPLE 114 trans-1-(i-Propyloxycarbonylamino)-4-phenyl-4-(3-(2,3-dihydrobenzofuran-7-yl)-3-oxo-2-azaprop-1-yl)cyclohexane

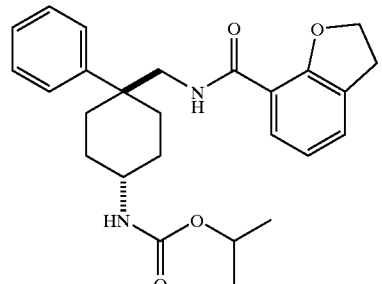

The title compound was prepared from the 4-nitrophenylcarbonate derivative of trans-1-amino-4-phenyl-4-(3-(2,3-dihydrobenzofuran-7-yl)-3-oxo-2-azaprop-1-yl)cyclohexane (Example 113) according to procedures described in Examples 67 and 68.

$^1$H NMR (CDCl$_3$) δ 1.16 (d, 6H, J=6 Hz), 1.59 (m, 2H), 1.68 (m, 2H), 1.90 (m, 2H), 2.40 (m, 2H), 3.21 (t, 2H, J=7 Hz), 3.50 (d, 2H, J=6 Hz), 4.52 (t, 2H, J=7 Hz); Mass Spectrum (PB-NH3/CI): m/e 437.3 (M+1).

The following Examples 115–116 were prepared as described in Example 114.

EXAMPLE 115 trans-1-(n-Butoxycarbonylamino)-4-phenyl-4-(3-(2,3-dihydrobenzofuran-7-yl)-3-oxo-2-azaprop-1-yl)cyclohexane

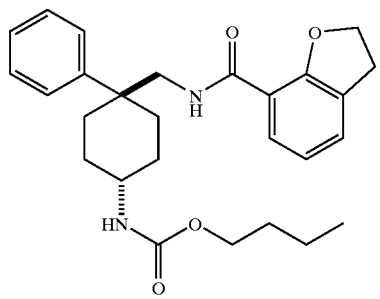

$^1$H NMR (CDCl$_3$) δ 0.89 (t, 3H, J=7 Hz), 1.18 (m, 2H), 1.51 (m, 2H), 1.67 (m, 2H), 1.90 (m, 2H), 2.40 (m, 2H), 3.19 (t, 2H, J=7 Hz), 3.50 (d, 2H, J=6 Hz), 4.51 (t, 2H, J=7 Hz); Mass Spectrum (PB-NH3/CI): m/e 451.3 (M+1).

EXAMPLE 116 trans-1-(Allyloxycarbonylamino)-4-phenyl-4-(3-(2,3-dihydrobenzofuran-7-yl)-3-oxo-2-azaprop-1-yl)cyclohexane

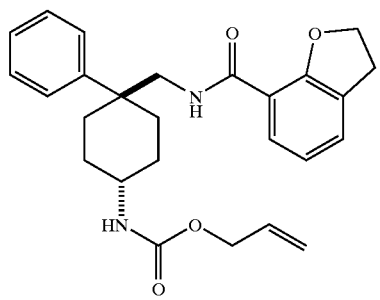

$^1$H NMR (CDCl$_3$) δ 1.18 (m, 2H), 1.67 (m, 2H), 1.90 (m, 2H), 2.40 (m, 2H), 3.21 (t, 2H, J=7 Hz), 3.50 (d, 2H, J=6 Hz), 4.51 (t, 2H, J=7 Hz), 5.16 (d, 1H, J=10 Hz), 5.24 (d, 1H, J=17 Hz); Mass Spectrum (PB-NH3/CI): m/e 435.3 (M+1).

EXAMPLE 117 trans-1-(i-Propyloxycarbonylamino)-4-phenyl-4-(3-(benzofuran-7-yl)-3-oxo-2-azaprop-1-yl)cyclohexane

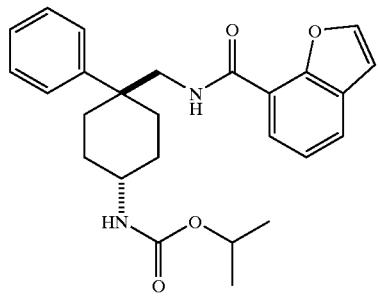

The title compound was prepared from the 4-nitrophenylcarbonate derivative of trans-1-amino-4- phenyl-4-(3-(benzofuran-7-yl)-3-oxo-2-azaprop-1-yl)cyclohexane (Example 113) according to procedures described in Examples 67 and 68.

$^1$H NMR (CDCl$_3$) δ 1.18 (d, 6H, J=5 Hz), 1.75 (m, 2H), 1.94 (m, 2H), 2.45 (m, 2H), 3.63 (d, 2H, J=6 Hz), 4.32 (brs, 1H), 4.86 (brs, 1H); Mass Spectrum (PB-NH3/CI): m/e 435.3 (M+1).

The following Examples 118–119 were prepared as described in Example 117.

EXAMPLE 118 trans-1-(n-Butoxycarbonylamino)-4-phenyl-4-(3-(benzofuran-7-yl)-3-oxo-2-azaprop-1-yl)cyclohexane

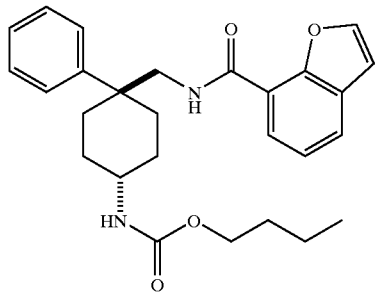

$^1$H NMR (CDCl$_3$) δ 0.95 (t, 3H, J=5 Hz), 1.24 (m, 2H), 1.54 (m, 2H), 1.75 (m, 2H), 1.95 (m, 2H), 2.45 (m, 2H), 3.63 (d, 2H, J=6 Hz), 4.00 (m, 2H), 4.37 (brs, 1H); Mass Spectrum (PB-NH3/CI): m/e 449.3 (M+1).

EXAMPLE 119 trans-1-(Allyloxycarbonylamino)-4-phenyl-4-(3-(benzofuran-7-y)-3-oxo-2-azaprop-1-yl)cyclohexane

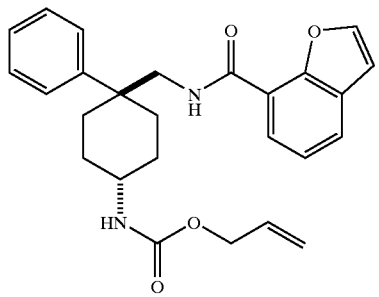

$^1$H NMR (CDCl$_3$) δ 1.24 (m, 2H), 1.73 (m, 2H), 1.95 (m, 2H), 2.46 (m, 2H), 3.64 (d, 2H, J=6 Hz), 4.45 (m, 1H), 4.51 (m, 2H), 5.16 (d, 1H, J=10 Hz), 5.24 (d, 1H, J=17 Hz), 5.89 (m, 1H); Mass Spectrum (PB-NH3/CI): m/e 433.3 (M+1).

EXAMPLE 120 trans and cis-1-Amino-1-cyano-4-phenyl-4-(3-(2-methoxyphenyl)-3-oxo-2-azaprop-1-yl)cyclohexane

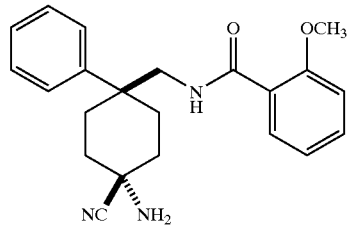

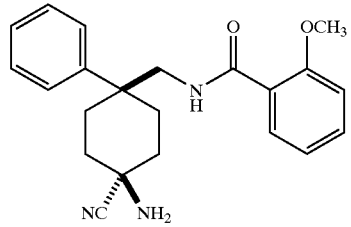

A solution of 3.00 g (8.9 mmol) of 4-phenyl-4-(3-(2-methoxyphenyl)-3-oxo-2-azaprop-1-yl)cyclohexanone in 50 mL of ammonia 7 M solution in methyl alcohol was stirred at r.t. for 1 hr and then 4.75 mL (35.6 mmol) of trimethylsilylcyanide was added slowly to the above reaction mixture. The reaction mixture were stirred at r.t. overnight and concentrated. Then 350 mL of methylene chloride was added, washed with 1N NaOH (30 mL), dried over Na$_2$SO$_4$ and concentrated. The residue was purified by chromatography (silica, CH$_2$Cl$_2$:MeOH:NH$_3$ 100:4:2, 2.0 M in MeOH) to afford the trans and cis isomers as a white solids.

For compound trans-1-amino-1-cyano-4-phenyl-4-(3-(2-methoxyphenyl)-3-oxo-2-azaprop-1-yl)cyclohexane $^1$H NMR (CDCl$_3$) δ 1.53 (m, 2H), 1.78 (s, 2H), 1.97 (m, 4H), 2.45 (m, 2H), 3.64 (d, 2H, J=6 Hz), 3.66 (s, 3H); Mass Spectrum (PB-NH3/CI): m/e 364.2 (M+1).

For compound cis-1-amino-1-cyano-4-phenyl-4-(3-(2-methoxyphenyl)-3-oxo-2-azaprop-1-yl)cyclohexane $^1$H NMR (CDCl$_3$) δ 1.85 (s, 2H), 1.98 (m, 4H), 2.04 (m, 2H), 2.17 (m, 2H), 3.54 (s, 3H), 3.79 (d, 2H, J=6 Hz); Mass Spectrum (PB-NH3/CI): m/e 364.2 (M+1).

Examples 121–123 were prepared from trans-1-amino-1-cyano-4-phenyl-4-(3-(2-methoxyphenyl)-3-oxo-2-azaprop-1-yl)cyclohexane and the corresponding chloroformate as described in Example 2.

EXAMPLE 121 trans-1-Cyano-1-(methoxycarbonylamino)-4-phenyl-4-(3-(2-methoxyphenyl)-3-oxo-2-azaprop-1-yl)cyclohexane

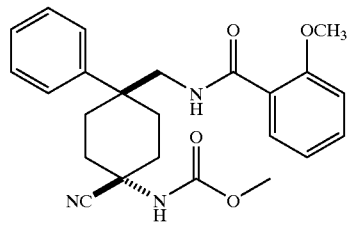

$^1$H NMR (CDCl$_3$) δ 1.64 (m, 2H), 2.07 (m, 2H), 2.45 (m, 4H), 3.67 (m, 8H); Mass Spectrum (PB-NH3/CI): m/e 422.2 (M+1).

EXAMPLE 122 trans-1-Cyano-1-(n-propyloxycarbonylamino)-4-phenyl-4-(3-(2-methoxyphenyl)-3-oxo-2-azaprop-1-yl)cyclohexane

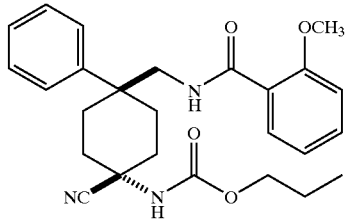

$^1$H NMR (CDCl$_3$) δ 0.92 (t, 3H, J=7 Hz), 1.62 (m, 4H), 2.07 (m, 2H), 2.43 (m, 4H), 3.65 (d, 2H, J=6 Hz), 3.69 (s, 3H), 4.03 (m, 2H ); Mass Spectrum (PB-NH3/CI): m/e 450.3 (M+1).

EXAMPLE 123 trans-1-(Allyloxycarbonylamino)-1-cyano-4-phenyl-4-(3-(2-methoxyphenyl)-3-oxo-2-azaprop-1-yl)cyclohexane

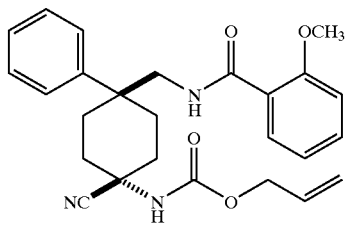

$^1$H NMR (CDCl$_3$) δ 1.57 (m, 2H), 2.07 (m, 2H), 2.45 (m, 4H), 3.66 (d, 2H, J=6 Hz), 3.69 (s, 3H), 4.56 (m, 2H ), 5.21 (d, 1H, J=10 Hz), 5.28 (d, 1H, J=18 Hz), 5.87 (m, 1H); Mass Spectrum (PB-NH3/CI): m/e 448.3 (M+1).

Examples 124–126 were prepared from cis-1-amino-1-cyano-4-phenyl-4-(3-(2-methoxyphenyl)-3-oxo-2-azaprop-1-yl)cyclohexane and the corresponding chloroformate as described in Example 2.

EXAMPLE 124 cis-1-Cyano-1-(methoxycarbonylamino)-4-phenyl-4-(3-(2-methoxyphenyl)-3-oxo-2-azaprop-1-yl)cyclohexane

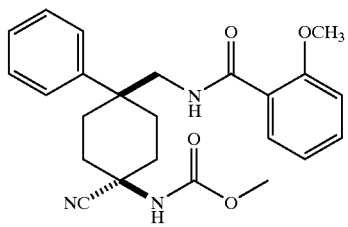

$^1$H NMR (CDCl$_3$) δ 2.07–2.27 (m, 8H), 3.55 (s, 3H), 3.64 (s, 3H), 3.72 (d, 2H, J=6 Hz); Mass Spectrum (PB-NH3/CI): m/e 422.3 (M+1).

EXAMPLE 125 cis-1-Cyano-1-(n-propyloxycarbonylamino)-4-phenyl-4-(3-(2-methoxyphenyl)-3-oxo-2-azaprop-1-yl)cyclohexane

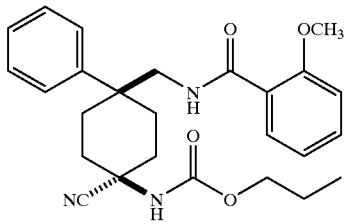

$^1$H NMR (CDCl$_3$) δ 0.94 (t, 3H, J=7 Hz), 1.63 (m, 2H), 2.07–2.27 (m, 8H), 3.54 (s, 3H), 3.77 (d, 2H, J=6 Hz), 4.06 (m, 2H); Mass Spectrum (PB-NH3/CI): m/e 450.3 (M+1).

EXAMPLE 126 cis-1-Cyano-1-(allyloxycarbonylamino)-4-phenyl-4-(3-(2-methoxyphenyl)-3-oxo-2-azapropyl)cyclohexane

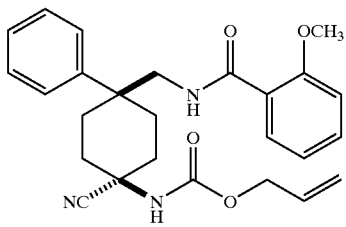

$^1$H NMR (CDCl$_3$) δ 0.94 (t, 3H, J=7 Hz), 1.63 (m, 2H), 2.07–2.27 (m, 8H), 3.54 (s, 3H), 3.77 (d, 2H, J=6 Hz), 4.58 (m, 2H), 5.20 (d, 1H, J=10 Hz), 5.29 (d, 1H, J=17 Hz), 5.86 (m, 1H); Mass Spectrum (PB-NH3/CI): m/e 448.3 (M+1).

EXAMPLE 127 cis and trans-1-(N-Methyl-N-allyloxycarbonylamino)-4-phenyl-4-(3-(2-methoxyphenyl)-3-oxo-2-azaprop-1-yl)cyclohexane

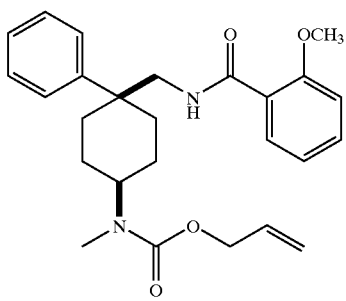

-continued

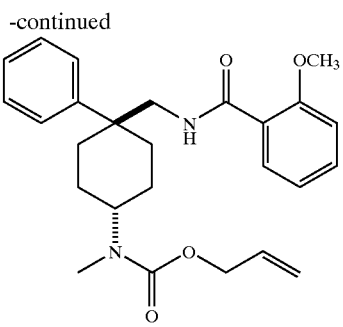

Step 1 cis and trans-1-(N-Methylamino)-4-phenyl-4-(3-(2-methoxyphenyl)-3-oxo-2-azaprop-1-yl)cyclohexane A solution of 220 mg (0.65 mmol) of 4-phenyl-4-(3-(2-methoxyphenyl)-3-oxo-2-azaprop-1-yl)cyclohexanone (Example 1, Step 3) in 40 mL of 1 M methylamine in THF was stirred at rt for 24 hr and then 49 mg (1.3 mmol) of $NaBH_4$ was added. The reaction mixture were stirred overnight and concentrated. Then 100 mL of methylene chloride was added, washed with 1N NaOH (15 mL), dried over $Na_2SO_4$ and concentrated. The residue was purified by chromatography (silica, $CH_2Cl_2$:MeOH:$NH_3$ 100:12:6, 2.0 M in MeOH) to afford the title compounds as a mixture (cis:trans=1:1).

Step 2 cis and trans-1-(N-Methyl-N-allyloxycarbonylamino)-4-phenyl-4-(3-(2-methoxyphenyl)-3-oxo-2-azaprop-1-yl)cyclohexane The title compounds were prepared from allylchloroformate according to procedures described in Example 2.

For cis-1-(N-methyl-N-allyloxycarbonylamino)-4-phenyl-4-(3-(2-methoxyphenyl)-3-oxo-2-azaprop-1-yl)cyclohexane $^1$H NMR (CDCl$_3$) δ 1.72 (m, 4H), 1.98 (m, 2H), 2.02 (m, 2H), 2.93 (s, 3H), 3.47 (s, 3H), 3.94 (d, 2H, J=6 Hz), 4.60 (d, 2H, J=6 Hz), 5.19 (d, 1H, J=10 Hz), 5.30 (d, 1H, J=17 Hz), 5.95 (m, 1H); Mass Spectrum (PB-NH3/CI): m/e 437.3 (M+1).

For trans-1-(N-methyl-N-allyloxycarbonylamino)-4-phenyl-4-(3-(2-methoxyphenyl)-3-oxo-2-azaprop-1-yl)cyclohexane, $^1$H NMR (CDCl$_3$) δ 1.47 (m, 2H), 1.58 (m, 8H), 1.72 (m, 2H), 2.48 (m, 2H), 2.55 (s, 3H), 3.54 (d, 2H, J=6 Hz), 3.68 (s, 3H), 4.58 (d, 2H, J=6 Hz), 5.17 (d, 1H, J=10 Hz), 5.25 (d, 1H, J=17 Hz), 5.91 (m, 1H); Mass Spectrum (PB-NH3/CI): m/e 437.3 (M+1).

EXAMPLE 128 cis and trans-1-(N-Methyl-N-phenoxycarbonylamino)-4-phenyl-4-(3-(2-methoxyphenyl)-3-oxo-2-azaprop-1-yl)cyclohexane

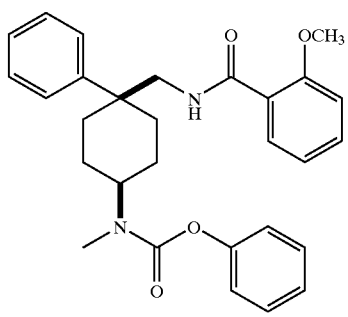

-continued

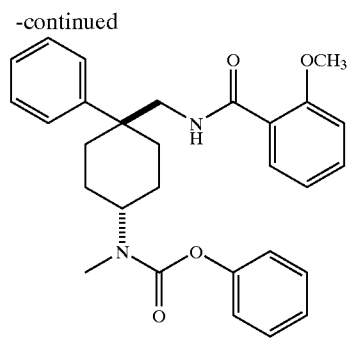

The title compounds were prepared in a 1:1 ratio as described in Example 127.

For trans-1-(N-methyl-N-phenoxycarbonylamino)-4-phenyl-4-(3-(2-methoxyphenyl)-3-oxo-2-azaprop-1-yl)cyclohexane $^1$H NMR (CDCl$_3$) δ 1.72 (m, 4H), 1.88 (m, 2H), 2.48 (m, 2H), 2.75 (s, 3H), 3.65 (s, 3H); Mass Spectrum (PB-NH3/CI): m/e 473.3 (M+1).

For cis-1-(N-methyl-N-phenoxycarbonylamino)-4-phenyl-4-(3-(2-methoxyphenyl)-3-oxo-2-azaprop-1-yl)cyclohexane, $^1$H NMR (CDCl$_3$) δ 2.92 (s, 3H), 3.47 (s, 3H); Mass Spectrum (PB-NH3/CI): m/e 473.3 (M+1).

EXAMPLE 129 trans-1-Amino-1-methoxycarbonyl-4-phenyl-4-(3-(2-methoxyphenyl)-3-oxo-2-azaprop-1-yl)cyclohexane

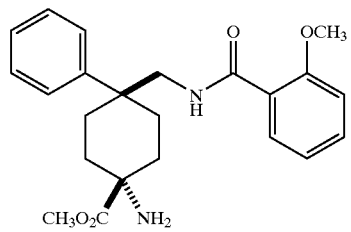

To a solution of 600 mg (1.65 mmol) of trans-1-amino-1-cyano-4-phenyl-4-(3-(2-methoxyphenyl)-3-oxo-2-azaprop-1-yl)cyclohexane (Example 120) in 25 mL of MeOH was bubbled in HCl gas at 0° C. until saturation. Then the reaction mixture were heated at reflux under HCl for 10 hr. Then it was concentrated, 200 mL of methylene chloride was added into the residue, washed with 2N NaOH (30 mL), dried over $Na_2SO_4$ and concentrated. The residue was purified by chromatography (silica, $CH_2Cl_2$:EtOAc:$NH_3$, 10:10:0.3, 2.0 M in MeOH) to afford the title compound as a white solid.

$^1$H NMR (CDCl$_3$) δ 1.48 (m, 2H), 1.68 (brs, 2H), 1.81 (m, 2H), 2.21 (m, 4H), 3.56 (s, 4 3H), 3.74 (m, 5H); Mass Spectrum (PB-NH3/CI): m/e 397.3 (M+1).

EXAMPLE 130 cis-1-Amino-1-methoxycarbonyl-4-phenyl-4-(3-(2-methoxyphenyl)-3-oxo-2-azaprop-1-yl)cyclohexane

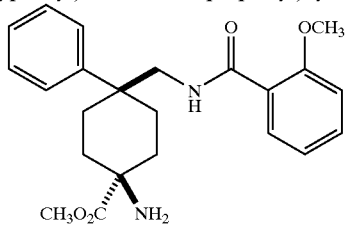

The title compound was prepared from cis-1-amino-1-cyano-4-phenyl-4-(3-(2-methoxyphenyl)-3-oxo-2-azaprop-1-yl)cyclohexane (Example 120) as described in Example 129.

$^1$H NMR (CDCl$_3$) δ 1.62 (m, 2H), 1.69 (brs, 2H), 1.87 (m, 2H), 2.05–2.11 (m, 4H), 3.626 (s, 3H), 3.633 (s, 3H), 3.68 (d, 2H, J=7 Hz); Mass Spectrum (PB-NH3/CI): m/e 397.3 (M+1).

EXAMPLE 131 trans-1-(i-Propyloxycarbonylamino)-1-methoxycarbonyl-4-phenyl-4-(3-(2-methoxyphenyl)-3-oxo-2-azaprop-1-yl)cyclohexane

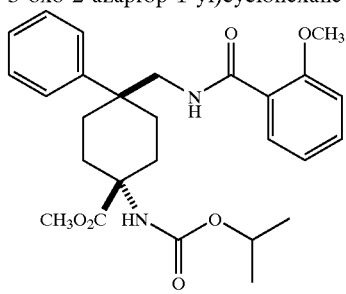

The title compound was prepared from trans-1-amino-1-methoxycarbonyl-4-phenyl-4-(3-(2-methoxyphenyl)-3-oxo-2-azaprop-1-yl)cyclohexane and i-propylchloroformate according to procedures described in Example 2.

$^1$H NMR (CDCl$_3$) δ 1.17 (d, 6H, J=6 Hz), 1.97 (m, 4H), 2.03 (m, 2H), 2.36 (m, 2H), 3.54 (s, 3H), 3.76 (s, 3H), 3.82 (d, 2H, J=7 Hz); Mass Spectrum (PB-NH3/CI): m/e 483.3 (M+1).

EXAMPLE 132 trans-1-(Allyloxycarbonylamino)-1-methoxycarbonyl-4-phenyl-4-(3-(2-methoxyphenyl)-3-oxo-2-azaprop-1-yl)cyclohexane

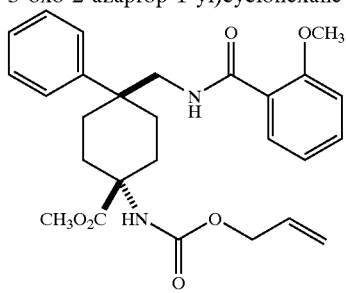

The title compound was prepared as described in Example 131. $^1$H NMR (CDCl$_3$) δ 1.93–2.54 (m, 8H), 3.54 (s, 3H), 3.77 (s, 3H), 3.85 (d, 2H, J=Hz); Mass Spectrum (PB-NH3/CI): m/e 481.3 (M+1).

EXAMPLE 133 cis-1-(i-Propyloxycarbonylamino)-1-methoxycarbonyl-4-phenyl-4-(3-(2-methoxyphenyl)-3-oxo-2-azaprop-1-yl)cyclohexane

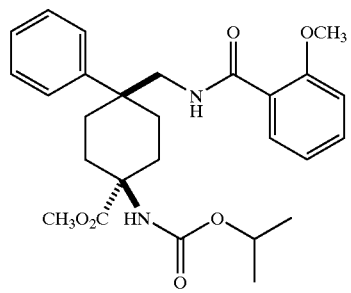

The title compound was prepared from cis- 1-amino-1-yl)cyclohexane and i-propylchloroformate according to procedures described in Example 2.

$^1$H NMR (CDCl$_3$) δ 1.23 (d, 6H, J=6 Hz), 1.81 (m, 4H), 2.02 (m, 2H), 2.29 (m, 2H), 3.62 (m, 5H); Mass Spectrum (PB-NH3/CI): m/e 483.3 (M+1).

EXAMPLE 134 cis-1-(i-Propyloxycarbonylamino)-1-methoxycarbonyl-4-phenyl-4-(3-(2-methoxyphenyl)-3-oxo-2-azapropyl)cyclohexane

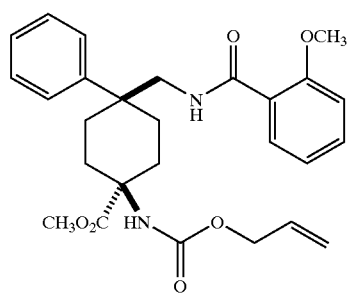

The title compound was prepared as described in Example 133.

$^1$H NMR (CDCl$_3$) δ 1.85 (m, 4H), 2.04 (m, 2H), 2.29 (m, 2H), 3.62 (m, 5H), 4.56 (d, 2H, J=5 Hz), 5.23 (d, 1H, J=10 Hz), 5.31 (d, 1H, J=20 Hz); Mass Spectrum (PB-NH3/CI): m/e 481.3 (M+1).

EXAMPLE 135 trans-1-(Allylcarbamoyloxy)-4-phenyl-4-(aminomethyl)cyclohexane

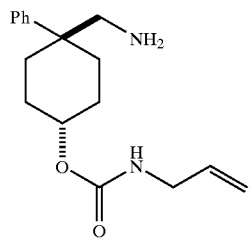

Step 1 cis-1-Hydroxy-4-phenyl-4-(aminomethyl)cyclohexane

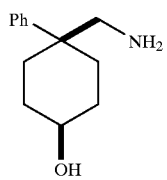

To a suspension of 7.01 g (35.20 mmol) of 4-cyano-4-phenyl cyclohexanone in 150 mL of anhydrous THF in a nitrogen atmosphere was added slowly 70.4 mL of lithium aluminum hydride (1.0 M in THF, 70.4 mmol) and the reaction mixture was refluxed for 3 hr. The TLC showed no starting material and the reaction mixture was cooled to 0° C. It was quenched with 6 mL of 4N NaOH at 0° C., filtered through a plug of $Na_2SO_4$ and concentrated to give the title compound as a colorless oil.

Step 2 cis-1-Hydroxy-4-phenyl-4-(t-butoxycarbonylaminomethyl)cyclohexane

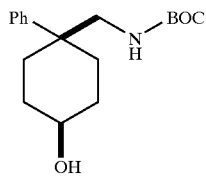

To a solution of 1.60 g (7.79 mmol) of cis-1-hydroxy-4-phenyl-4-(aminomethyl)cyclohexane and 3.25 mL of triethylamine (23.4 mmol) in 30 mL of methylene chloride was added 1.61 g (7.40 mmol) of di-tert-butyl dicarbonate at 0° C. The reaction mixture was stirred overnight and was poured into 300 mL of methylene chloride. It was washed with aq $NaHCO_3$, dried over $MgSO_4$ and concentrated. The residue was purified by chromatography (silica, methylene chloride:ethyl acetate, 3:1) to afford the title compound as a white solid.

Step 3 trans-1-Benzoyloxy-4-phenyl-4-(t-butoxycarbonylaminomethyl)cyclohexane

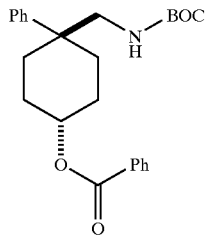

To a solution of 1.01 g (3.3 mmol) of cis-1-hydroxy-4-phenyl-4-(t-butoxycarbonylaminomethyl)cyclohexane, 1.91 g (7.27 mmol) of triphenylphosphine and 0.967 g (7.92 mmol) of benzoic acid in 15 mL of THF was added (10 min.) 1.14 mL (7.27 mmol) of diethyl azodicarboxylate at rt slowly, and the reaction mixture was stirred at rt overnight. It was concentrated and the residue was purified by chromatography (silica, hexanes:ethyl acetate, 9:1) to afford the title compound as a white solid.

$^1$H NMR (CDCl$_3$) δ 1.41 (s, 9H), 1.63 (m, 2H), 1.72 (m, 2H), 2.03 (m, 2H), 2.34 (m, 2H), 3.26 (d, 2H, J=6 Hz), 4.24 (brs, 1H), 5.10 (m, 1H), 7.27–7.52 (m, 8H), 7.96 d, 2H, J=8 Hz); Mass Spectrum (PB-NH3/CI): m/e 410 (M+1).

Step 4 trans-1-Hydroxy-4-phenyl-4-(t-butoxycarbonylainomethyl)cyclohexane

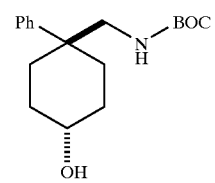

A solution of 700 mg (1.71 mmol) of trans-1-benzoyloxy-4-phenyl-4-(t-butoxycarbonylaminomethyl)cyclohexane, 8 mL of sodium methoxide (0.5 M in MeOH, 4.0 mmol) in 15 mL of methanol and 20 mL of THF was stirred at rt. After 15 hours, the TLC analysis of the reaction mixture showed no starting material and the reaction mixture was concentrated. The residue was redissolved in 50 mL of methylene chloride and 10 mL of water. It was adjusted to PH=7 with 0.5 N HCl and extracted with $CH_2Cl_2$ (20 mL×3). The combined organic extracts were dried over $MgSO_4$ and concentrated. The residue was purified by chromatography (silica, hexanes:ethyl acetate, 1:1) to afford the title compound as a white solid.

$^1$H NMR (CDCl$_3$) δ 1.28 (m, 2H), 1.39 (s, 9H), 1.55 (m, 2H), 1.86 (m, 2H), 2.03 (m, 2H), 3.17 (d, 2H, J=6 Hz), 3.71 (m, 1H), 4.21 (brs, 1H), 7.25–7.39 (m, 5H); Mass Spectrum (PB-NH3/CI): m/e 306 (M+1).

Step 5 trans-1-(4-Nitrophenyloxy)carbonyloxy-4-phenyl-4-(t-butoxycarbonylaminomethyl)cyclohexane

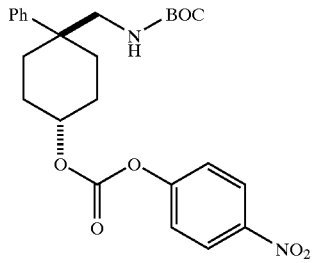

A solution of 569 mg (1.86 mmol) of trans-1-hydroxy-4-phenyl-4-(t-butoxycarbonylaminomethyl)cyclohexane, 562 mg (2.79 mmol) of 4-nitrophenyl chlorofomate and 568 mg (4.65 mmol) of DMAP in 20 mL of dichloromethane was stirred at rt for 3 h. The reaction mixture was concentrated and the residue was purified by chromatography (silica, hexanes:ethyl acetate, 8:1) to afford the title compound as a white solid.

Step 6 trans-1-(N-Allylcarbamoyl)oxy-4-phenyl-4-(t-butoxycarbonylaminomethyl)cyclohexane

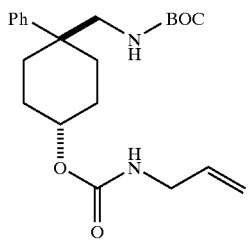

To a solution of 375 mg (0.796 mmol) of trans-1-(4-nitrophenyloxy)carbonyloxy-4-phenyl-4-(t-butoxycarbonyl-aminomethyl)cyclohexane in 10 mL of dichloromethane was added 0.6 mL of allylamine at rt. The reaction mixture were stirred for 2 h. Then it was concentrated and the residue was purified by chromatography (silica, hexanes:ethyl acetate, 6:1 to 4:1) to afford the title compound as a white solid.

$^1$H NMR (CDCl$_3$) δ 1.28 (m, 2H), 1.39 (s, 9H), 1.64 (m, 2H), 1.91 (m, 2H), 2.05 (m, 2H), 3.19 (d, 2H, J=6 Hz), 3.75 (m, 2H), 4.23 (brs, 1H), 4.63 (brs, 1H), 4.72 (brs, 1H), 5.08 (d, 1H, J=10 Hz), 5.12 (d, 1H, J=17 Hz), 5.79 (m, 1H); Mass Spectrum (PB-NH3/CI): m/e 389 (M+1).

Step 7 trans-1-(Allylcarbamoyloxy)-4-phenyl-4-(aminomethyl)cyclohexane

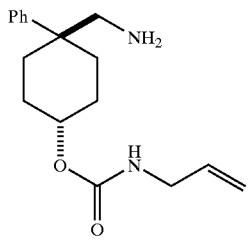

A solution of 280 mg (0.72 mmol) of trans-1-(N-allylcarbamoyl)oxy-4-phenyl-4-(t-butoxycarbonylaminomethyl)cyclohexane and 3 mL of TFA in 6 mL of dichloromethane was stirred at 0° C. for 1 h. Then it was concentrated and the residue was redissolved in 50 mL of methylene chloride and 5 mL of 2 N NaOH. It extracted with CH$_2$Cl$_2$ (20 mL×3). The combined organic extracts were dried over Na$_2$SO$_4$ and concentrated to afford the title compound as a white solid.

$^1$H NMR (CDCl$_3$) δ 1.12 (brs, 2H), 1.41 (m, 2H), 1.52 (s, 9H), 1.90 (m, 2H), 2.34 (m, 2H), 2.67 (s, 2H), 3.75 (m, 2H), 4.71 (m, 2H), 5.08 (d, 1H, J=10 Hz), 5.12 (d, 1H, J=17 Hz), 5.79 (m, 1H); Mass Spectrum (PB-NH3/CI): m/e 289 (M+1).

EXAMPLE 136 trans 1-(N-Allylcarbamoyloxy)-4-phenyl-4-(3-(2-methoxy-5-chlorophenyl)-3-oxo-2-azaprop-1-yl)cyclohexane

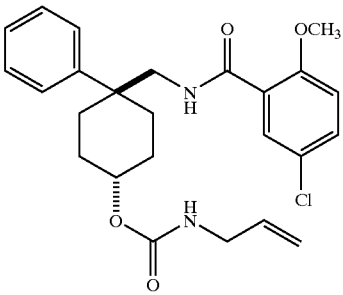

The title compound was prepared from trans-1-(allylcarbamoyloxy)-4-phenyl-4-(aminomethyl)cyclohexane and the corresponding acid as described in Example 136.

$^1$H NMR (CDCl$_3$) δ 1.50 (m, 2H), 1.72 (m, 2H), 1.95 (m, 2H), 2.33 (m, 2H), 3.45 (s, 3H), 3.64 (d, 2H, J=7 Hz), 3.76 (s, 2H), 4.63 (brs, 1H), 4.77 (brs, 1H), 5.10 (d, 1H, J=10 Hz), 5.16 (d, 1H, J=17 Hz), 5.80 (m, 1H); Mass Spectrum (PB-NH3/CI): m/e 457.2 (M+1).

EXAMPLE 137 trans 1-(N-Allylcarbamoyloxy)-4-phenyl-4-(3-(2-hydroxy-3-chlorophenyl)-3-oxo-2-azapropyl)cyclohexane

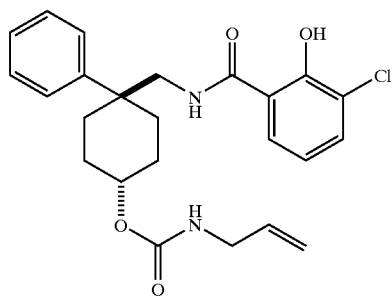

The title compound was prepared from trans-1-(allylcarbamoyloxy)-4-phenyl-4-(aminomethyl)cyclohexane and the corresponding acid as described in Example 136.

$^1$H NMR (CDCl$_3$) δ 1.45 (m, 2H), 1.71 (m, 2H), 1.95 (m, 2H), 2.33 (m, 2H), 3.53 (d, 2H, J=6 Hz), 3.75 (s, 2H), 4.63 (brs, 1H), 4.75 (brs, 1H), 5.09 (d, 1H, J=10 Hz), 5.12 (d, 1H, J=17 Hz), 5.80 (m, 1H); Mass Spectrum (PB-NH3/CI): m/e 443 (M+1).

EXAMPLE 138 trans 1-(N-Allylcarbamoyloxy)-4-phenyl-4-(3-(2-methoxy-3-chlorophenyl)-3-oxo-2-azaprop-1-yl)cyclohexane

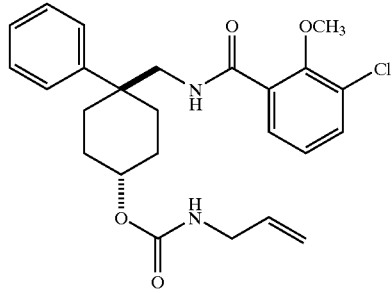

A solution of 40 mg (0.09 mmol) of trans 1-(N-allylcarbamoyloxy)-4-phenyl-4-(3-(2-hydroxy-3-chlorophenyl)-3-oxo-2-azapropyl)cyclohexane (Example 138), 20 mg (0.156 mmol) of potassium carbonate and 22 mg (0.18 mmol) of iodomethane in 10 mL of DMF was stirred at 40° C. for 5 hr, Then it was concentrated and the residue was purified by schromatography (silica, hexanes-:ethyl acetate, 2:1 to 1:1) to afford the title compound as a white solid.

$^1$H NMR (CDCl$_3$) δ 1.51 (m, 2H), 1.74 (m, 2H), 1.95 (m, 2H), 2.33 (m, 2H), 3.45 (s, 3H), 3.64 (d, 2H, J=7 Hz), 3.77 (s, 2H), 4.63 (brs, 1H), 4.77 (brs, 1H), 5.10 (d, 1H, J=10 Hz), 5.16 (d, 1H, J=17 Hz), 5.80 (m, 1H); Mass Spectrum (PB-NH3/CI): m/e 457.2 (M+1).

EXAMPLE 139 trans 1-(N-Allylcarbamoyloxy)-4-phenyl-4-(3-(2-hydroxy-5-fluorophenyl)-3-oxo-2-azaprop-1-yl)cyclohexane

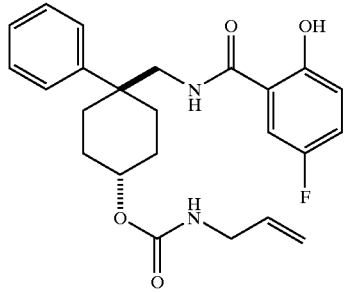

The title compound was prepared from trans-1-(allylcarbamoyloxy)-4-phenyl-4-(aminomethyl)cyclohexane and the corresponding acid as described in Example 136.

$^1$H NMR (CDCl$_3$) δ 1.46 (m, 2H), 1.72 (m, 2H), 1.96 (m, 2H), 2.34 (m, 2H), 3.52 (d, 2H, J=7 Hz), 3.77 (s, 2H), 4.59 (s, 1H), 4.77 (brs, 1H), 5.10 (d, 1H, J=10 Hz), 5.14 (d, 1H, J=17 Hz), 5.80 (m, 1H); Mass Spectrum (PB-NH3/CI): m/e 427 (M+1).

EXAMPLE 140 trans 1-(N-Allylcarbamoyloxy)-4-phenyl-4-(3-(2-hydroxy-5-fluorophenyl)-3-oxo-2-azaprop-1-yl)cyclohexane

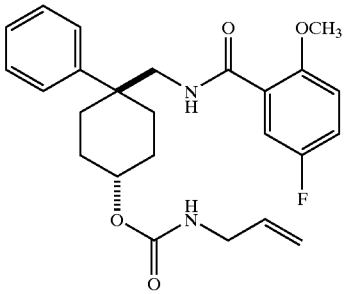

The title compound was prepared from trans 1-(N-allylcarbamoyloxy)-4-phenyl-4-(3-(2-hydroxy-5-fluorophenyl)-3-oxo-2-azaprop-1-yl)cyclohexane (Example 141) as described in Example 139.

$^1$H NMR (CDCl$_3$) δ 1.47 (m, 2H), 1.73 (m, 2H), 1.94 (m, 2H), 2.29 (m, 2H), 3.60 (s, 3H), 3.63 (d, 2H, J=7 Hz), 3.75 (s, 2H), 4.65 (brs, 1H), 4.77 (brs, 1H), 5.08 (d, 1H, J=10 Hz), 5.12 (d, 1H, J=17 Hz), 5.80 (m, 1H); Mass Spectrum (PB-NH3/CI): m/e 441 (M+1).

The following Examples 143 to 148 were prepared from 4-aminomethyl-4-phenylcyclohexanone ethyleneglycol ketal and the corresponding acid as described in Example 1. The NMR and Mass Spectrum data were consistent with the structure.

EXAMPLE 141

4-Phenyl-4-(3-(2-ethoxyphenyl)-3-oxo-2-azaprop-1-yl)cyclohexanone

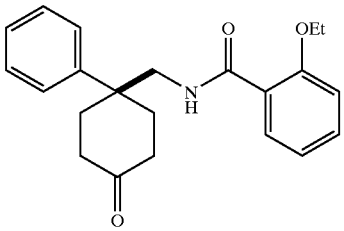

$^1$H NMR (CDCl$_3$) δ 8.2–6.9 (aromatic H's, 9H); 4.0 (q, J=7.3 Hz, 2H); 3.8 (d, J=7.2 Hz, 2H); 2.5 (m, 4H); 2.3 (m, 2H); 2.15 (m, 2H); 1.16 (t, J=7.3 Hz, 3H). Mass Spec: 352.1 (CI, M+1).

EXAMPLE 142

4-Phenyl-4-(3-(2-hydroxyphenyl)-3-oxo-2-azaprop-1-yl)cyclohexanone

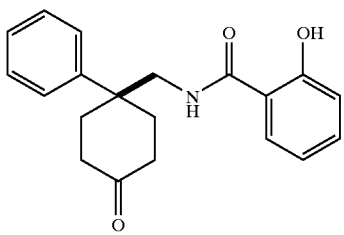

$^1$H NMR (CDCl$_3$) δ 7.6–7.4 (aromatic H's, 6H); 7.0 (dd, J=7.2 Hz, 2H); 6.8 (dd, J=7.6 Hz, 1H); 5.95 (br s, 1H); 3.67 (d, J=6.4 Hz, 2H); 2.6 (m, 2H); 2.46 (m, 2H); 2.33 (m, 2H); 2.1 (m, 2H). Mass Spec: 324.1 (CI, M+1).

EXAMPLE 143

4-Phenyl-4-(3-(2-acetoxyphenyl)-3-oxo-2-azaprop-1-yl)cyclohexanone

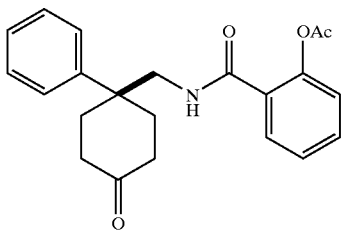

$^1$H NMR (CDCl$_3$) δ 7.66 (dd, J=7.7, 1.6 Hz, 1H); 7.5 (m, 5H); 7.36 (m, 1H); 7.28 (m, 1H); 7.08 (d, J=7.7 Hz, 1H); 6.04 (br s, 1H); 3.7 (d, J=6.4 Hz, 2H); 2.52 (m, 4H); 2.32 (m, 2H); 2.12 (m, 2H); 2.05 (s, 3H).

EXAMPLE 144

4-Phenyl-4-(3-(2-(N,N-dimethylamino)phenyl)-3-oxo-2-azaprop-1-yl)cyclohexanone

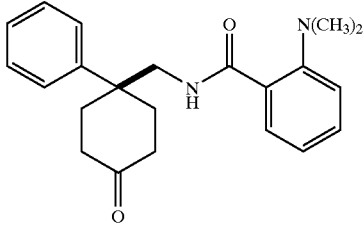

$^1$H NMR (CDCl$_3$) δ 9.74 (brs, 1H), 8.15 (dd, J$_1$=7.9 Hz, J$_2$=1.7 Hz, 1H), 7.51–7.15 (aromatic H's, 8H), 3.85 (d, J=5.9 Hz, 2H), 2.55–2.47 (m, 4H), 2.35 (s, 6H), 2.39–2.30 (m, 2H), 2.18–2.10 (m, 2H). Mass Spec: 351.3 (CI, M+1).

EXAMPLE 145

4-Phenyl-4-(3-(2-benzyloxyphenyl)-3-oxo-2-azaprop-1-yl)cyclohexanone

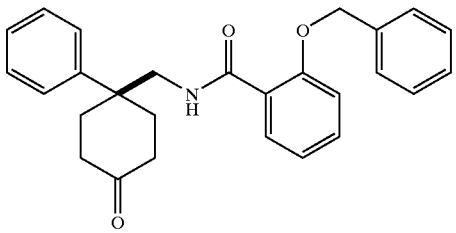

$^1$H NMR (CDCl$_3$) δ 8.19 (dd, J$_1$=7.8 Hz, J$_2$=1.8 Hz, 1H), 7.75 (brs, 1H), 7.43–7.20 (aromatic H's, 11H), 7.08 (t, J=7.8 Hz, 1H), 6.98 (d, J=7.7 Hz, 1H), 5.05 (s, 2H), 3.62 (d, J=7.0, 2H), 2.36–2.30 (m, 4H), 2.25–2.16 (m, 2H), 1.93–1.86 (m, 2H). Mass Spec: 414.2 (CI, M+1).

EXAMPLE 146

4-Phenyl-4-(3-(2,3-methylenedioxyphenyl)-3-oxo-2-azaprop-1-yl)cyclohexanone

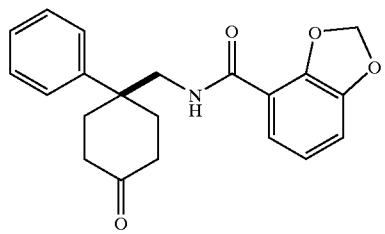

$^1$H NMR (CDCl$_3$) δ 7.56–6.90 (aromatic H's, 8H), 6.73 (brs, 1H), 5.90 (s, 2H), 3.71 (d, J=6.4 Hz, 2H), 2.60–2.53 (m, 2H), 2.50–2.43 (m, 2H), 2.37–2.29 (m, 2H), 2.15–2.08 (m, 2H).

EXAMPLE 147 trans 1-(N-Allylcarbamoyloxy)-4-phenyl-4-(3-(2-cyclopropyloxyphenyl)-3-oxo-2-azaprop-1-yl)cyclohexane

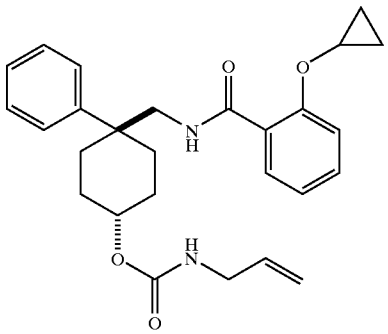

The title compound may be prepared from trans-1-(allylcarbamoyloxy)-4-phenyl-4-(aminomethyl)cyclohexane and the corresponding acid as described in Example 136.

The following examples 150 to 153 were prepared from their corresponding cyano precursors as described in Example 1, Steps 2 and 3.

EXAMPLE 148

1-Phenyl-1-(3-(2-methoxyphenyl)-3-oxo-2-azaprop-1-yl)cyclohexane

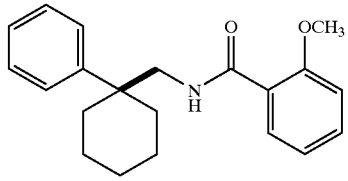

¹H NMR (CDCl₃) δ 1.46 (m, 4H), 1.67 (m, 2H), 1.78 (m, 2H), 2.10 (m, 2H), 3.60 (s, 3H), 3.70 (d, 2H), 6.86 (d, 1H), 7.0 (t, 1H), 7.28 (m, 1H), 7.38–7.46 (m, 5H), 7.55 (brm, 1H), 8.21 (dd, 1H). Mass Spectrum m/e 324 (M⁺1).

EXAMPLE 149

1-Phenyl-1-(3-(2-methoxyphenyl)-3-oxo-2-azaprop-1-yl)cyclopentane

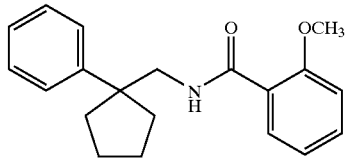

¹H NMR (CDCl₃) δ 1.76 (m, 2H), 1.92 (m, 4H), 2.05 (m, 2H), 3.63 (s, 3H), 3.69 (d, 2H), 6.87 (d, 1H), 7.0 (t, 1H), 7.28 (m, 1H), 7.38–7.42 (m, 5H), 7.68 (brm, 1H), 8.21 (dd, 1H). Mass Spectrum m/e 310 (M⁺1).

EXAMPLE 150

1-Phenyl-1-(3-(2-methoxyphenyl)-3-oxo-2-azaprop-1-yl)cyclopentane

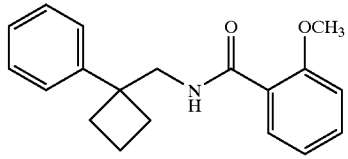

¹H NMR (CDCl₃) δ 1.92 (m, 1H), 2.27 (m, 3H), 2.35 (m, 2H), 3.70 (s, 3H), 3.90 (d, 2H), 6.90 (d, 1H), 7.07 (t, 1H), 7.22–7.28 (m, 3H), 7.41–7.44 (m, 3H), 7.72 (brm, 1H), 8.24 (dd, 1H). Mass Spectrum m/e 296 (M⁺1).

EXAMPLE 151

1-Phenyl-1-(3-(2-methoxyphenyl)-3-oxo-2-azaprop-1-yl)cyclopentane

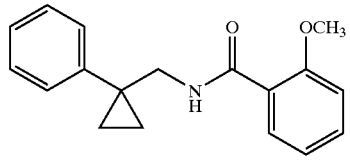

¹H NMR (CDCl₃) δ 0.94 (m, 2H), 0.98 (m, 2H), 3.69 (d, 2H), 3.76 (s, 3H), 6.92 (d, 1H), 7.07 (t, 1H), 7.24–7.28 (m, 1H), 7.34–7.44 (m, 6H), 7.99 (brm, 1H), 8.20 (dd, 1H). Mass Spectrum m/e 282 (M⁺1).

The following Examples 210 to 218 were prepared from trans 1-((4-Nitrophenoxy)carbonyloxy)-4-phenyl-4-(3-(2-methoxyphenyl)-3-oxo-2-azapropyl)cyclohexane (Example 2) according to procedures described in Example 3.

EXAMPLES 152 AND 153 trans and cis 1-Methanesulfonyloxy-4-phenyl-4-(3-(2-methoxyphenyl)-3-oxo-2-azaprop-1-yl)cyclohexane

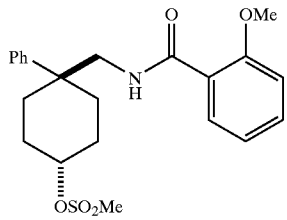

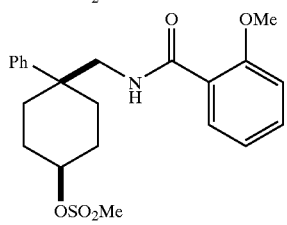

To a mixture of trans and cis 1-hydroxy-4-phenyl-4-(3-(2-methoxyphenyl)-3-oxo-2-azaprop-1-yl)cyclohexane (Example 1, 92.0 mg, 0.27 mmol) in 2.0 mL of CH₂Cl₂ was added Et₃N (0.19 mL, 1.4 mmol) and MsCl (0.084 mL, 0.96 mmol) at 0° C. and the reaction mixture was stirred at rt for 16 h. The volatiles were removed and the residue was filtered through a plug of silica gel, purified by HPLC (Waters RCM, μ Porosil, 25 mm×10 cm) using a mixture of (5:4:1 hexane-methyl tert-butyl ether-acetonitrile:hexane, 4.5/4.0 to 9.0/0.0 mL/min) to give the title compounds.

Spectrum data for trans 1-methanesulfonyloxy-4-phenyl-4-(3-(2-methoxyphenyl)-3-oxo-2-azaprop-1-yl)cyclohexane:¹H NMR (CDCl₃) δ 8.19 (d, 1H, J=7.8 Hz), 7.58 (bs, 1H), 7.30–7.44 (m, 6H), 7.04 (t, 1H, J=7.5 Hz), 6.87 (d, 1H, J=8.3 Hz), 4.82 (bs, 1H), 3.71 (d, 2H, J=6.0 Hz), 3.60 (s, 3H), 3.02 (s, 3H), 3.58–3.67 (m, 2H), 1.76–2.11 (m, 8H); Mass Spectrum (CI) m/e 418 (M+1).

Spectrum data for cis 1-methanesulfonyloxy-4-phenyl-4-(3-(2-methoxyphenyl)-3-oxo-2-azaprop-1-yl)cyclohexane: ¹H NMR (CDCl₃) δ 8.17 (d, 1H, J=7.8 Hz), 7.59 (bs, 1H), 7.29–7.45 (m, 6H), 7.03 (t, 1H, J=7.3 Hz), 6.87 (d, 1H, J=8.2 Hz), 4.80 (bs, 1H), 3.64 (d, 2H, J=6.2 Hz), 3.60 (s, 3H), 2.94 (s, 3H), 3.58–3.67 (m, 2H), 1.71–2.36 (m, 8H); Mass Spectrum (CI) m/e 418 (M+1).

EXAMPLE 154 cis-1-Benzyloxy-4-phenyl-4-(3-(2-methoxyphenyl)-3-oxo-2-azaprop-1-yl)cyclohexane

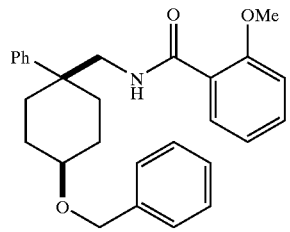

To a solution of cis-1-hydroxy-4-phenyl-4-(3-(2-methoxyphenyl)-3-oxo-2-azaprop-1-yl)cyclohexane (32 mg, 0.094 mmol) in a mixture of Ether/CH$_2$Cl$_2$ (2 mL/2 mL) was added benzyl trichloroacetimdate (0.070 mL, 0.376 mmol) and two drops of CF$_3$SO$_2$OH at 0° C. and the reaction mixture was stirred at 0° C. for 1 h. The mixture was poured into CH$_2$Cl$_2$, washed with NaHCO$_3$, and dried over Na$_2$SO$_4$. The residue was purified by HPLC (Waters RCM, μ Porosil, 25 mm×10 cm) using a mixture of (5:4:1 hexane-methyl tert-butyl ether-acetonitrile:hexane, 2.25/8.0 to 3.6/7.0 mL/min) to give the title compound.

$^1$H NMR (CDCl$_3$), 8.22 (d, 1H, J=7.7 Hz), 7.58 (bs, 1H), 7.26–7.46 (m, 11H), 7.05 (t, 1H, J=8.0 Hz), 6.86 (d, 1H, J=8.2 Hz), 4.55 (s, 2H), 3.75 (d, 2H, J=5.7 Hz), 3.58 (s, 3H), 3.49 (m, 1H), 1.71–2.16 (m, 8H); Mass Spectrum (CI) m/e 430 (M+1).

EXAMPLE 155 trans-1-Benzyloxy-4-phenyl-4-(3-(2-methoxyphenyl)-3-oxo-2-azaprop-1-yl)cyclohexane

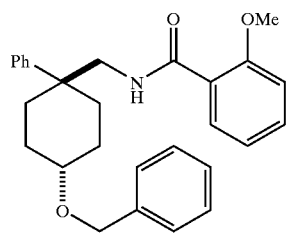

The title compound was prepared from trans-1-hydroxy-4-phenyl-4-(3-(2-methoxyphenyl)-3-oxo-2-azaprop-1-yl)cyclohexane as described in example 156.

$^1$H NMR (CDCl$_3$) δ 8.23 (d, 1H, J=7.5 Hz), 7.60 (bs, 1H), 7.24–7.47 (m, 11H), 7.06 (t, 1H, J=7.5 Hz), 6.88 (d, 1H, J=8.0 Hz), 4.52 (s, 2H), 3.66 (d, 2H, J=6.0 Hz), 3.63 (s, 3H), 3.54 (m, 1H), 1.49–2.41 (m, 8H); Mass Spectrum (CI) m/e 430 (M+1).

EXAMPLE 156 trans-1-t-Butoxy-4-phenyl-4-(3-(2-methoxyphenyl)-3-oxo-2-azaprop-1-yl)cyclohexane

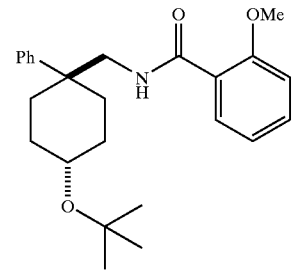

The title compound was prepared from trans-1-hydroxy-4-phenyl-4-(3-(2-methoxyphenyl)-3-oxo-2-azaprop-1-yl)cyclohexane as described in Example 156.

$^1$H NMR (CDCl$_3$) δ 8.22 (d, 1H, J=7.8 Hz), 7.59 (bs, 1H), 7.37–7.45 (m, 5H), 7.24 (t, 1H, J=7.1 Hz), 7.06 (t, 1H, J=7.6 Hz), 6.89 (8.5 Hz), 3.65 (s, 3H), 3.58 (d, 2H, J=5.9 Hz), 3.50 (m, 1H), 2.40 (d, 2H, J=12.6 Hz), 1.32–1.73 (m, 6H), 1.16 (s, 9H); Mass Spectrum (CI) m/e 396 (M+1).

EXAMPLE 157 trans-1-Methoxy-4-phenyl-4-(3-(2-methoxyphenyl)-3-oxo-2-azaprop-1-yl)cyclohexane

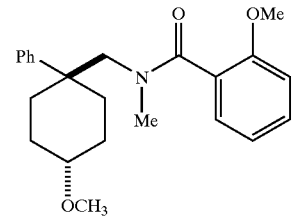

A mixture of trans-1-hydroxy-4-phenyl-4-(3-(2-methoxyphenyl)-3-oxo-2-azaprop-1-yl)cyclohexane (77.2 mg, 0.23 mmol) and NaH (36 mg, 0.9 mmol) in 5 mL of THF was stirred at rt for 40 min. To it was added MeI (0.14 mL, 2.28 mmol). After it was heated at 45° C. for 14 h, the reaction mixture was poured into CH$_2$Cl$_2$, washed with 2N HCl, filtered through a plug of silica gel and concentrated. The residue was purified by HPLC (Waters RCM, μ Porosil, 25 mm×10 cm) using a mixture of (5:4:1 hexane-methyl tert-butyl ether-acetonitrile:hexane, 6.75/6.0 mL/min) to give the title compound.

$^1$H NMR (CDCl$_3$) δ 7.46 (d, 2H, J=8.2 Hz), 7.32 (t, 2H, J=7.6 Hz), 7.28 (t, 1H, J=7.6 Hz), 7.17 (d, 1H, J=8.0 Hz), 7.13 (t, 1H J=7.4 Hz), 6.93 (t, 1H, J=7.3 Hz), 6.85 (d, 1H, J=8.5 Hz), 3.91–3.93 (m, 1H), 3.84 (s, 3H), 3.24–3.33 (m, 2H), 3.27 (s, 3H), 2.39–2.67 (m, 2H), 1.18–2.11 (m, 6H); Mass Spectrum (CI) m/e 368 (M+1).

EXAMPLES 158 AND 159 trans and cis-1-(2-Bromobenzoyl)oxy-4-phenyl-4-(3-(2-methoxyphenyl)-3-oxo-2-azaprop-1-yl)cyclohexane

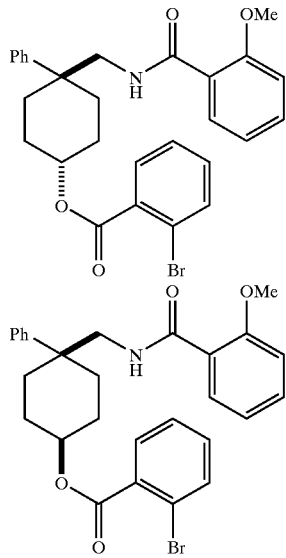

To a mixture of trans and cis-1-hydroxy-4-phenyl-4-(3-(2-methoxyphenyl)-3-oxo-2-azaprop-1-yl)cyclohexane (69.5 mg, 0.205 mmol) in 2.0 mL of pyridine was added DMAP (2 mg) and 2-bromobenzoyl chloride (0.1 1 mL, 0.96 mmol) at rt and the reaction mixture was stirred at rt for 2 h. The volatiles were removed by vacuum and the residue was filtered through a plug of silica gel, and concentrated. The residue was purified by HPLC (Waters RCM, $\mu$ Porosil, 25 mm×10 cm) using a mixture of (5:4:1 hexane-methyl tert-butyl ether-acetonitrile:hexane, 2.25/8.0 mL/min) to give the title compounds.

Spectrum data for the trans isomer: $^1$H NMR (CDCl$_3$) δ 8.21 (d, 1H, J=8.0 Hz), 7.84 (d, 1H, J=8.0 Hz), 7.67 (d, 1H, J=7.0 Hz), 7.62 (bs, 1H), 7.30–7.48 (m, 8H), 7.04 (t, 1H, J=7.5 Hz), 6.86 (d, 1H, J=8.0 Hz), 5.15 (m, 1H), 3.76 (d, 2H, J=6.0 Hz), 3.58 (s, 3H), 1.80–2.10 (m, 8H). Mass Spectrum (CI) m/e 522, 524 ($^{79}$Br, $^{81}$Br, M+1).

Spectrum data for the cis isomer: $^1$H NMR (CDCl$_3$) δ 8.21 (d, 1H, J=7.8 Hz), 7.67 (d, 1H, J=7.4 Hz), 7.24–7.62 (m, 10H), 7.05 (t, 1H, J=7.6 Hz), 6.88 (d, 1H, J=8.2 Hz), 5.18 (m, 1H), 3.71 (d, 2H, J=5.9 Hz), 3.62 (s, 3H), 1.67–2.41 (m, 8H; Mass Spectrum (CI) m/e 522, 524 ($^{79}$Br, $^{81}$Br, M+1).

EXAMPLE 160 cis-1-(t-Butoxycarbonylmethyl)oxy-4-phenyl-4-(3-(2-methoxyphenyl)-3-oxo-2-azaprop-1-yl)cyclohexane

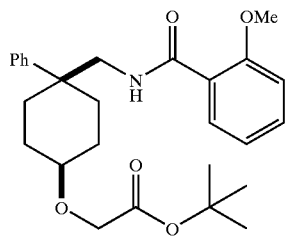

To a solution of cis-1-hydroxy-4-phenyl-4-(3-(2-methoxyphenyl)-3-oxo-2-azaprop-1-yl)cyclohexane (40.3 mg, 0.12 mmol) in 2 mL of THF at −78° C. was added LHMDS (lithium bis(trimethylsilyl)amide) (0.29 mL, 1 N, 0.29 mmol). After 20 min, t-butyl bromoacetate (0.058 mL, 0.36 mmol) was added at −78° C. and the reaction mixture was allowed to warm slowly to rt and mix for 16 h. The reaction was quenched with pH=7 buffer, filtered through silica gel and concentrated. The residue was purified by HPLC (Waters RCM, $\mu$ Porosil, 25 mm×10 cm) using a mixture of (5:4:1 hexane-methyl tert-butyl ether-acetonitrile:hexane, 4.5/8.0 mL/min) to give the title compound.

$^1$H NMR (CDCl$_3$) δ 8.20 (d, 1H, J=7.8 Hz), 7.55 (bs, 1H), 7.36–7.45 (m, 5H), 7.27 (t, 1H, J=6.8 Hz), 7.03 (t, 1H, J=7.1 Hz), 6.86 (d, 1H, J=8.1 Hz), 4.00 (s, 3H), 3.73 (d, 2H, J=5.9 Hz), 3.59 (s, 2H), 3.46 (m, 1H), 1.67–2.13 (m, 8H), 1.48 (s, 9H);Mass Spectrum (CI) m/e 454 (M+1).

EXAMPLE 161 cis 1-Benzenesulfonyloxy-4-phenyl-4-(3-(2-methoxyphenyl)-3-oxo-2-azaprop-1-yl)cyclohexane

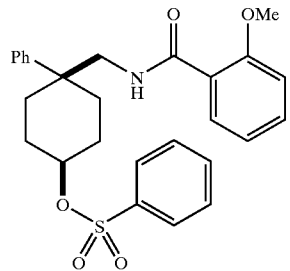

To a solution of cis 1-hydroxy-4-phenyl-4-(3-(2-methoxyphenyl)-3-oxo-2-azaprop-1-yl)cyclohexane (44.5 mg, 0.13 mmol) in 2 mL of pyridine was added DMAP (2.1 mg) and benzenesulfonyl chloride (0.087 mL, 0.65 mmol) and the reaction mixture was stirred at 65° C. for 16 h. The volatiles were removed by vacuum and the residue was filtered through silica gel and purified by HPLC (Waters RCM, $\mu$ Porosil, 25 mm×10 cm) using a mixture of (5:4:1 hexane-methyl tert-butyl ether-acetonitrile:hexane, 6.75/8.0 mL/min) to give the title compound.

$^1$H NMR (CDCl$_3$) δ 8.18 (d, 1H, J=7.8 Hz), 7.91 (d, 2H, J=8.5 Hz), 7.62 (t, 1H J=6.1 Hz), 7.57 (bs, 1H), 7.52 (t, 2H, J=6.0 Hz), 7.36–7.41 (m, 5H), 7.28 (t, 1H, J=7.3 Hz), 7.03 (t, 1H, J=7.1 Hz), 6.87 (d, 1H, J=8.0 Hz), 4.67 (m, 1H), 3.65 (d, 2H, J=5.9 Hz), 3.61 (s, 3H), 1.62–2.06 (m, 8H); Mass Spectrum (CI) m/e 480 (M+1).

EXAMPLE 162 cis-1-Benzenesulfonyloxy-4-phenyl-4-(3-(2-methoxyphenyl)-3-oxo-2-azaprop-1-yl)cyclohexane

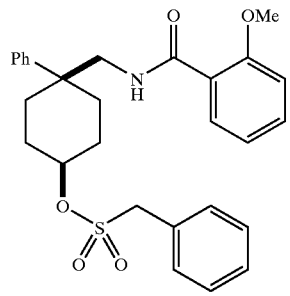

The title compound was prepared from cis-1-hydroxy-4-phenyl-4-(3-(2-methoxyphenyl)-3-oxo-2-azaprop-1-yl)cyclohexane as described in Example 163, with the exception that the reaction was stirred at rt.

$^1$H NMR (CDCl$_3$) δ 8.22 (d, 1H, J=7.8 Hz), 7.57 (bs, 1H), 7.37–7.44 (m, 10H), (m, 6H), 7.30 (t, 1H, J=7.1 Hz), 7.05 (t, 1H, J=7.3 Hz), 6.87 (d, 1H, J=8.2 Hz), 4.63 (s, 1H), 4.36 (s, 2H), 3.67 (d, 2H, J=5.7 Hz), 3.60 (s, 3H), 1.63–2.00 (m, 8H); Mass Spectrum (CI) m/e 494 (M+1).

EXAMPLE 163

1-Methylidene-4-phenyl-4-(3-(2-methoxyphenyl)-3-oxo-2-azaprop-1-yl)cyclohexane

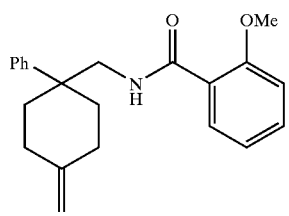

To a suspension of methyltriphenylphosphonium bromide (141.5 mg, 0.396 mmol) in 4 mL of THF was added KHMDS (potassium bis(trimethylsilyl)amide) (0.396 mmol, 0.5M in THF) at 0° C. and the solution was allowed to stir at rt for 40 min. The reaction mixture was then cooled to −78° C. and to it was added a solution of 4-phenyl-4-(3-(2-methoxyphenyl)-3-oxo-2-azaprop-1-yl)cyclohexanone (78.9 mg, 0.165 mmol) in 2 mL of THF. The mixture was then allowed to warm to rt for 2.5 h and then quenched with pH=7 buffer (2 drops). The solution was filtered through a plug of silica gel and concentrated. The residue was purified by flash chromatography (silica, EtOAc/hexanes) to give the title compound.

$^1$H NMR (CDCl$_3$) δ 8.20 (d, 1H, J=7.8 Hz), 7.59 (bs, 1H), 7.38–7.45 (m, 4H), 7.35 (t, 1H, J=8.5 Hz), 7.27 (t, 1H, J=7.1 Hz), 7.00 (t, 1H, J=7.5 Hz), 6.83 (d, 1H, J=8.3 Hz), 4.61 (s, 2H), 3.71 (d, 2H, J=6.0 Hz), 3.56 (s, 3H); Mass Spectrum (CI) m/e 336 (M+1).

EXAMPLES 164 AND 165

1-Methyl-4-phenyl-4-(3-(2-methoxyphenyl)-3-oxo-2-azaprop-1-yl)-cyclohexane

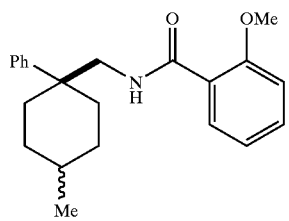

A mixture of 1-phenyl-1-(3-(2-methoxyphenyl)-3-oxo-2-azaprop-1-yl)-4-methylidenecyclohexane (Example 165, 38 mg, 0.11 mmol) and Pd/C (10%, 16.7 mg) in 15 mL of EtOAc was shaken under 50 psi of H$_2$ for 2.5 h. The mixture was filtered through a plug of celite, concentrated and the residue was purified by HPLC (Waters RCM, µ Porosil, 25 mm×10 cm) using a mixture of (5:4:1 hexane-methyl tert-butyl ether-acetonitrile:hexane, 2.0/8.9 mL/min) to afford the two isomers of the title compound.

Isomer #1: $^1$H NMR (CDCl$_3$) δ 8.22 (d, 1H, J=7.8 Hz), 7.52 (bs, 1H), 7.26–7.47 (m, 5H), 7.28 (t, 1H, J=7.4 Hz), 7.03 (t, 1H, J=7.3 Hz), 6.83 (d, 1H, J=8.5 Hz), 3.90 (d, 2H, J=5.8 Hz), 3.49 (s, 3H); 1.00 (d, 3H, J=6.1 Hz); Mass Spectrum (CI) m/e 338 (M+1).

Isomer #2: $^1$H NMR (CDCl$_3$) δ 8.22 (d, 1H, J=7.8 Hz), 7.57 (bs, 1H), 7.37–7.44 (m, 5H), 7.27 (t, 1H, J=6.9 Hz), 7.04 (t, 1H, J=7.3 Hz), 6.87 (d, 1H, J=8.2 Hz), 3.65 (s, 3H), 3.56 (d, 2H, J=6.0 Hz), 0.79 (d, 3H, J=6.4 Hz); Mass Spectrum (CI) m/e 338 (M+1).

EXAMPLE 166

1-Hydroxy-1-hydroxymethyl-4-phenyl-4-(3-(2-methoxyphenyl)-3-oxo-2-azaprop-1-yl)-cyclohexane

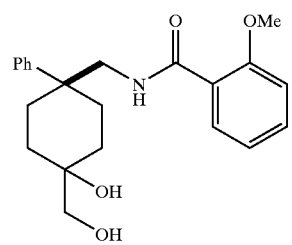

To a solution of 1-phenyl-1-(3-(2-methoxyphenyl)-3-oxo-2-azaprop-1-yl)-4-methylidenecyclohexane (Example 165, 22.3 mg, 0.66 mmol) in 1.0 mL of THF was added OsO$_4$ (33.8 mg, 0.13 mmol), pyridine (0.5 mL) and water (0.5 mL). The mixture was stirred at rt for 17 h. To the reaction mixture was then added 1 mL of saturated NaHSO$_3$ solution. After 1 h, the volatiles were removed by vacuum and the residue was loaded onto silica gel and eluted with first EtOAc/Hexane (1:1) then EtOAc to give the title compound as a 2:1 mixture of diastereomers.

$^1$H NMR (CDCl$_3$) 8.13–8.16 (m, 1H), 6.82–6.87 (m, 1H), 3.56 (s, 3H, OMe), 3.51 (s, 3H, OMe); Mass Spectrum (CI) m/e 370 (M+1).

EXAMPLES 167 AND 168

1-Hydroxy-1-(2-methoxybenzoyloxymethyl)-4-phenyl-4-(3-(2-methoxyphenyl)-3-oxo-2-azaprop-1-yl)-cyclohexane

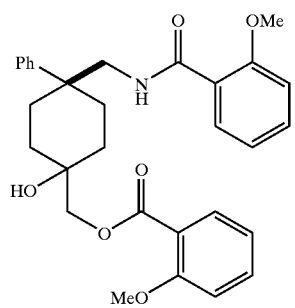

To solution of 1-hydroxy-1-hydroxymethyl-4-phenyl-4-(3-(2-methoxyphenyl)-3-oxo-2-azaprop-1-yl)-cyclohexane (Example 168, 20.2 mg, 0.055 mmol) in 2.0 mL of THF was added DMAP (2 mg), pyridine (0.054 mL, 0.67 mmol) and 2-methoxybenzoyl chloride (0.050 mL, 0.34 mmol). The solution was stirred at rt for 18 h and was quenched with methanol (0.5 mL). The volatiles were removed by vacuum and the residue was filtered through a plug of silica gel, concentrated and the residue was purified by HPLC (Waters RCM, μ Porosil, 25 mm×10 cm) using a mixture of (5:4:1 hexane-methyl tert-butyl ether-acetonitrile:hexane, 3.0/9.0 to 8.0/0.0, mL/min) to give the separated isomers of the title compound.

Spectrum data for isomer #1: $^1$H NMR (CDCl$_3$) δ 8.19 (d, 1H, J=7.8 Hz), 7.85 (d, 1H, J=7.8 Hz), 7.58 (bs, 1H), 7.36–7.50 (m, 6H), 7.29 (t, 1H, J=6.7 Hz), 7.00–7.05 (m, 2H), 6.98 (d, 1H, J=8.4 Hz), 6.84 (d, 1H, J=8.2 Hz), 4.33 (s, 2H), 3.89 (s, 3H), 3.84 (d, 2H, J=5.7 Hz), 3.53 (s, 3H), 2.53 (s, 1H), 2.16–2.21 (m, 2H), 1.90–1.95 (m, 4H), 1.74–1.78 (m, 2H); Mass Spectrum (CI) m/e 504 (M+1).

Spectrum data for isomer #2: $^1$H NMR (CDCl$_3$) δ 8.21 (d, 1H, J=7.8 Hz), 7.69 (d, 1H, J=8.0 Hz), 7.61 (bs, 1H), 7.39–7.49 (m, 6H), 7.30 (t, 1H, J=6.8 Hz), 7.05 (t, 1H, J=8.0 Hz), 6.96–6.98 (m, 2H), 6.88 (d, 1H, J=8.3 Hz), 4.06 (s, 2H), 3.87 (s, 3H), 3.67 (s, 3H), 3.64 (d, 2H, J=5.9 Hz), 2.43 (s, 1H), 2.23–2.26 (m, 2H), 2.11 (t, 2H, J=13.9 Hz), 1.71–1.73 (m, 2H), 1.46 (t, 2H, J=11.1 Hz); Mass Spectrum (CI) m/e 504 (M+1).

EXAMPLES 169 AND 170

1-Hydroxy-1-acetoxymethyl-4-phenyl-4-(3-(2-methoxyphenyl)-3-oxo-2-azaprop-1-yl)-cyclohexane

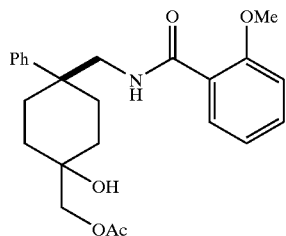

The title compounds were prepared and purified as described in Examples 169 and 170.

Spectrum data for isomer #1: $^1$H NMR (CDCl$_3$) δ 8.17 (d, 1H, J=7.8 Hz), 7.57 (bs, 1H), 7.37–7.45 (m, 5H), 7.28 (t, 1H, J=7.1 Hz), 7.01 (t, 1H, J=7.5 Hz), 6.83 (d, 1H, J=8.2 Hz), 4.08 (s, 2H), 3.80 (d, 2H, J=6.0 Hz), 3.50 (s, 3H), 2.10 (s, 3H), 1.64–2.14 (m, 8H); Mass Spectrum (CI) m/e 412 (M+1).

Spectrum data for isomer #2: $^1$H NMR (CDCl$_3$) δ 8.20 (d, 1H, J=7.7 Hz), 7.28–7.70 (m, 7H), 7.05 (t, 1H, J=7.3 Hz), 6.88 (d, 1H, J=8.2 Hz), 3.84 (s, 3H), 3.67 (s, 1H), 3.62 (d, 2H, J=6.0 Hz), 2.04 (s, 3H); Mass Spectrum (CI) m/e 412 (M+1).

EXAMPLE 171

1-Methoxycarbonylmethylidenyl-4-phenyl-4-(3-(2-methoxyphenyl)-3-oxo-2-azaprop-1-yl)-cyclohexane

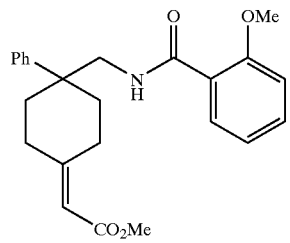

To a solution of methyl diethylphosphonoacetate (0.088 mL, 0.48 mmol) in 2 mL of THF was added lithium bis(trimethylsilyl)amide (0.48 mL, 1N, 0.48 mmol in THF) at 0° C. and the reaction mixture stirred for 50 min The solution was then added to a solution of 4-phenyl-4-(3-(2-methoxyphenyl)-3-oxo-2-azaprop-1-yl)cyclohexanone (67.1 mg, 0.20 mmol) in 2 mL of THF at −78° C. and the solution was allowed to warm to rt overnight. The solution was then filtered through a plug of silica gel, concentrated and was purified by flash chromatography (silica, EtOAc/Hexane, 3:7) to give the title compound.

$^1$H NMR (CDCl$_3$) δ 8.17 (d, 1H, J=7.8 Hz), 7.59 (broad t, 1H, J=5.3 Hz), 7.39–7.44 (m, 4H), 7.36 (t, 1H, J=8.9 Hz), 7.29 (t, 1H, J=7.1 Hz), 7.01 (t, 1H, J=7.5 Hz), 6.84 (d, 1H, J=8.2 Hz), 5.61 (s, 1H), 3.64 (s, 3H), 3.59 (s, 3H); Mass Spectrum (CI) m/e 394 (M+1).

EXAMPLE 172

1-Carboxymethylidenyl-4-phenyl-4-(3-(2-methoxyphenyl)-3-oxo-2-azaprop-1-yl)-cyclohexane

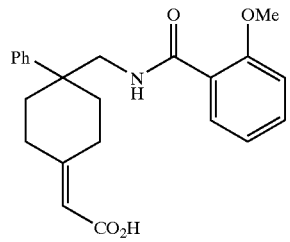

To a solution of 1-methoxycarbonylmethylidenyl-4-phenyl-4-(3-(2-methoxyphenyl)-3-oxo-2-azaprop-1-yl)-cyclohexane (32.2 mg, 0.082 mmol) in 3.0 mL of methanol was added lithium hydroxide monohydrate (6.9 mg, 0.164 mmol) and water (1 mL) and the reaction mixture was heated at 60° C. for 8 h. To the solution was then added 2N HCl to bring the pH=3.0 and volatiles were removed by vacuum. The white solid was dissolved in CH$_2$Cl$_2$ and filtered through celite (to remove LiCl) and evaporated to give the title compound.

$^1$H NMR (CDCl$_3$) δ 8.20 (d, 1H, J=7.5 Hz), 7.66 (bs, 1H), 7.28–7.47 (m, 6H), 7.05 (t, 1H, J=8.3 Hz), 6.87 (d, 1H, J=8.2 Hz), 5.66 (s, 1H), 3.62 (s, 3H); Mass Spectrum (CI) m/e 380 (M+1).

EXAMPLE 173 AND 174

1-Methoxycarbonylmethyl-4-phenyl-4-(3-(2-methoxyphenyl)-3-oxo-2-azaprop-1-yl)-cyclohexane

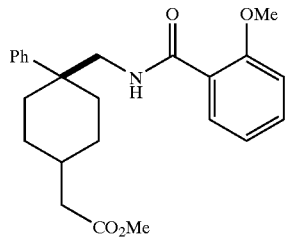

To a solution of 1-methoxycarbonylmethylidenyl-4-phenyl-4-(3-(2-methoxyphenyl)-3-oxo-2-azaprop-1-yl)-cyclohexane (29.2 mg, 0.074 mmol) in a mixture of EtOAc/methanol (5 mL/5 mL) was added Pd/C (10%) (32 mg) and the reaction mixture was shaken under 50 psi of $H_2$ for 16 h. The mixture was filtered through a plug of celite, concentrated and the residue was purified by HPLC (Waters RCM, μ Porosil, 25 mm×10 cm) using a mixture of (5:4:1 hexane-methyl tert-butyl ether-acetonitrile:hexane, 2.25/8.0 to 3.6/7.0 mL/min) to give the separated isomers of the title compound.

Spectrum data for isomer #1: $^1$H NMR (CDCl$_3$) δ 8.20 (d, 1H, J=7.8 Hz), 7.52 (bs, 1H), 7.27–7.45 (m, 6H), 7.03 (t, 1H, J=7.3 Hz), 6.82 (d, 1H, J=8.2 Hz), 3.89 (d, 2H, J=5.8 Hz), 3.68 (s, 3H), 3.49 (s, 3H), 2.34 (d, 2H, J=7.1 Hz), 1.51–2.13 (m, 9H); Mass Spectrum (CI) m/e 396 (M+1).

Spectrum data for isomer #2: $^1$H NMR (CDCl$_3$) δ 8.21 (d, 1H, J=7.6 Hz), 7.57 (bs, 1H), 7.27–7.42 (m, 6H), 7.06 (t, 1H, J=7.6 Hz), 6.89 (d, 1H, J=8.2 Hz), 3.67 (s, 3H), 3.62 (s, 3H), 3.56 (d, 2H, J=5.9 Hz), 2.42 (d, 2H, J=13.8 Hz), 2.09 (d, 2H, J=7.1 Hz), 1.00–1.93 (m, 7H); Mass Spectrum (CI) m/e 396 (M+1).

EXAMPLE 175

1-t-Butoxycarbonylmethyl-4-phenyl-4-(3-(2-methoxyphenyl)-3-oxo-2-azaprop-1-yl)-cyclohexane

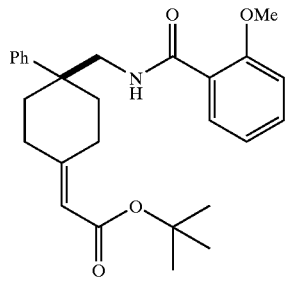

The title compound was prepared as described in Example 173. $^1$H NMR (CDCl$_3$) δ 8.19 (d, 1H, J=7.8 Hz), 7.60 (bs, 1H), 7.28–7.47 (m, 6H), 7.05 (t, 1H, J=7.5 Hz), 6.87 (d, 1H, J=8.5 Hz), 5.56 (s, 1H), 3.78 (d of d, 1H, J=13.3, 6.2 Hz), 3.67 (d of d 1H, J=13.3, 6.2 Hz), 3.62 (s, 3H), 3.27–3.29 (m, 1H), 1.87–2.56 (m, 6H), 1.47 (s, 9H); Mass Spectrum (CI) m/e 436 (M+1).

EXAMPLES 176 AND 177

1-t-Butoxycarbonylmethyl-4-phenyl-4-(3-(2-methoxyphenyl)-3-oxo-2-azaprop-1-yl)-cyclohexane

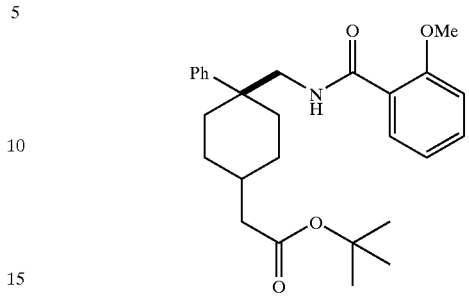

A solution of 1-t-butoxycarbonylmethylidenyl-4-phenyl-4-(3-(2-methoxyphenyl)-3-oxo-2-azaprop-1-yl)-cyclohexane (28.5 mg, 0.065 mmol) and Pd/C (10 mg, 10%) in 10 mL of EtOAc was shaken under 50 psi of hydrogen for 48 h. The mixture was filtered through a plug of silica gel, concentrated and the residue was purified by HPLC (Waters RCM, μ Porosil, 25 mm×10 cm) using a mixture of (5:4:1 hexane-methyl tert-butyl ether-acetonitrile:hexane, 4.5/8.0 mL/min) to give the separated isomers at C1.

Spectra data for isomer #1: $^1$H NMR (CDCl$_3$) δ 8.19 (d, 1H, J=7.8 Hz), 7.52 (bs, 1H), 7.36–7.45 (m, 5H), 7.28 (t, 1H, J=7.1 Hz), 7.03 (t, 1H, J=7.6 Hz), 6.82 (d, 1H, J=8.3 Hz), 3.89 (d, 2H, J=5.7 Hz), 3.49 (s, 3H), 2.24 (d, 2H, J=6.9 Hz), 2.12 (d, 2H, J=12.6 Hz), 1.42–1.81 (m, 7H), 1.46 (s, 9H); Mass Spectrum (CI) m/e 438 (M+1).

Spectra data for isomer #2. $^1$H NMR (CDCl$_3$) δ 8.20 (d, 1H, J=7.8 Hz), 7.57 (bs, 1H), 7.25–7.42 (m, 6H), 7.03 (t, 1H, J=7.3 Hz), 6.87 (d, 1H, J=8.2 Hz), 3.65 (s, 3H), 3.55 (d, 2H, J=5.9 Hz), 2.41 (d, 2H, J=11.9 Hz), 1.98 (d, 2H, J=7.1 Hz), 1.84–1.86 (m, 1H), 1.60–1.66 (m, 4H), 1.39 (s, 9H), 1.02–1.07 (m, 2H); Mass Spectrum (CI) m/e 438 (M+1).

EXAMPLE 178

1-(-Benzylaminocarbonylmethylidenyl)-4-phenyl-4-(3-(2-methoxyphenyl)-3-oxo-2-azaprop-1-yl)-cyclohexane

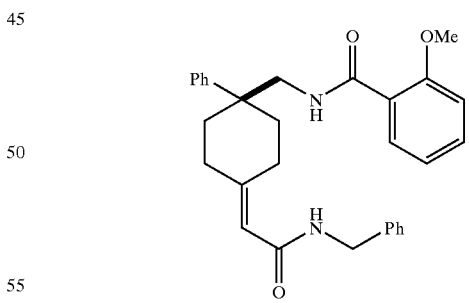

A solution of 1-carboxymethylidenyl-4-phenyl-4-(3-(2-methoxyphenyl)-3-oxo-2-azaprop-1-yl)-cyclohexane (Example 174, 43.4 mg, 0.11 mmol), EDC (32.9 mg, 0.17 mg), DMAP (34.9 mg, 0.29 mmol) and benzylamine (0.025 mL, 0.23 mmol) in 2 mL CH$_2$Cl$_2$ was stirred at rt for 24 h. The reaction mixture was then filtered through a plug of silica gel, concentrated and the residue was purified by HPLC (Waters RCM, μ Porosil, 25 mm×10 cm) using a mixture of (5:4:1 hexane-methyl tert-butyl ether-acetonitrile:hexane, 6.75/6.0 mL/min) to give the title compound.

¹H NMR (CDCl₃) δ 8.16 (d, 1H, J=7.8 Hz), 7.60 (bs, 1H), 7.22–7.45 (m, 11H), 7.02 (t, 1H, J=7.6 Hz), 6.86 (d, 1H, J=8.2 Hz), 6.25 (t, 1H, J=5.7 Hz), 5.58 (s, 1H), 4.43 (d, 2H, J=5.7 Hz), 3.77 (d of d, 1H, J=13.3, 6.2 Hz), 3.59–3.62 (m, 1H), 3.60 (s, 3H), 3.33–3.38 (m, 1H), 2.56–2.62 (m, 1H), 2.13–2.27 (m, 4H), 1.83–1.90 (m, 2H); Mass Spectrum (CI) m/e 469 (M+1).

EXAMPLE 179

1-(-Benzylaminocarbonylmethyl)-4-phenyl-4-(3-(2-methoxyphenyl)-3-oxo-2-azaprop-1-yl)-cyclohexane

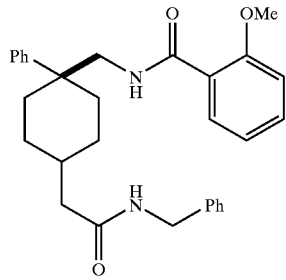

The title compound as a mixture of isomers was prepared from 1-(-benzylaminocarbonylmethylidenyl)-4-phenyl-4-(3-(2-methoxyphenyl)-3-oxo-2-azaprop-1-yl)-cyclohexane as described in Examples 178 and 179.

¹H NMR (CDCl₃) δ 8.17 (d, 1H, J=7.8 Hz), 7.54 (bs, 1H), 7.23–7.44 (m, 11H), 7.02 (t, 1H, J=7.6 Hz), 6.82 (d, 1H, J=8.5 Hz), 6.19 (bs, 1H), 4.45 (d, 2H, J=5.8 Hz), 3.87 (d, 2H, J=5.7 Hz), 3.48 (s, 3H), 2.22 (d, 2H, J=7.0 Hz), 2.10 (d, 2H, J=13.3 Hz), 1.46–1.96 (m, 7H); Mass Spectrum (CI) m/e 471 (M+1).

EXAMPLE 180

1-(-Phenylaminocarbonylmethylidenyl)-4-phenyl-4-(3-(2-methoxyphenyl)-3-oxo-2-azaprop-1-yl)-cyclohexane

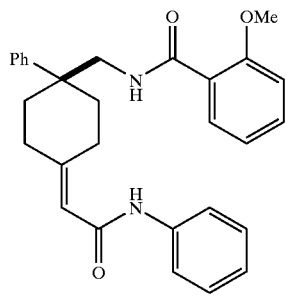

The title compound was prepared as described in Example 180. ¹H NMR (CDCl₃) δ 8.53 (bs, 1H), 8.20 (d, 1H, J=7.8 Hz), 7.69 (bs, 1H), 7.62 (d, 2H, J=7.6 Hz), 7.24–7.42 (m, 8H), 7.01–7.05 (m, 2H), 6.87 (d, 1H, J=8.5 Hz), 6.25 (t, 1H, J=5.7 Hz), 5.78 (s, 1H), 3.80 (d of d, 1H, J=13.5, 6.5 Hz), 3.61 (d of d, 1H, J=13.5, 6.5 Hz), 3.60 (s, 3H), 3.41–3.46 (m, 1H), 2.59–2.62 (m, 1H), 2.12–2.26 (m, 4H), 1.83–1.87 (m, 2H); Mass Spectrum (CI) m/e 455 (M+1).

EXAMPLES 181 AND 182

1-(-Phenylaminocarbonylmethylidenyl)-4-phenyl-4-(3-(2-methoxyphenyl)-3-oxo-2-azaprop-1-yl)-cyclohexane

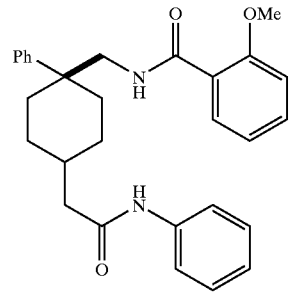

The title compound (isomers #1 and #2) was prepared from 1-(-phenylaminocarbonylmethylidenyl)-4-phenyl-4-(3-(2-methoxyphenyl)-3-oxo-2-azaprop-1-yl)-cyclohexane as described in Examples 178 and 179.

Isomer #1. ¹H NMR (CDCl₃) δ 8.28 (bs, 1H), 8.21 (d, 1H, J=7.8 Hz), 7.67 (d, 2H, J=7.54 (bs, 1H), 7.27–7.42 (m, 8H), 7.03–7.10 (m, 2H), 6.84 (d, 1H, J=8.0 Hz), 3.89 (d, 2H, J=6.8 Hz), 3.49 (s, 3H), 2.29 (d, 2H, J=7.1 Hz), 2.09 (d, 2H, J=13.2 Hz), 1.42–1.99 (m, 7H); Mass Spectrum (CI) m/e 457 (M+1).

Isomer #2. ¹H NMR (CDCl₃) δ 8.17 (d, 1H, J=8.0 Hz), 7.78 (bs, 1H), 7.60 (bs, 1H), 7.51 (d, 2H, J=8.0 Hz), 7.25–7.41 (m, 8H), 7.06 (t, 1H, J=7.5 Hz), 7.01 (t, 1H, J=7.3 Hz), 6.88 (d, 1H, J=8.3 Hz), 3.67 (s, 3H), 3.52 (d, 2H, J=6.0 Hz), 2.39 (d, 2H, J=12.8 Hz), 2.08 (d, 2H, J=7.1 Hz), 1.00–2.08 (m, 7H); Mass Spectrum (CI) m/e 457 (M+1).

EXAMPLE 183

1-Carboxymethyl-4-phenyl-4-(3-(2-methoxyphenyl)-3-oxo-2-azaprop-1-yl)-cyclohexane

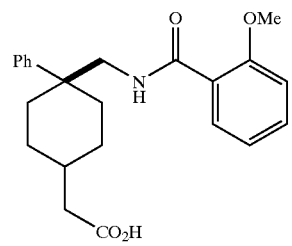

A mixture of 1-carboxymethylidenyl-4-phenyl-4-(3-(2-methoxyphenyl)-3-oxo-2-azaprop-1-yl)-cyclohexane (Example 174, 64 mg, 0.17 mmol) and Pd/C (10 mg, 10%), in 5.0 mL of EtOAc was shaken under 50 psi of hydrogen for 24 h. The mixture was filtered through a plug of silica gel and concentrated to give the title compound as a mixture of isomers.

EXAMPLES 184 AND 185

1-(N-Allylaminocarbamoylmethyl)-4-phenyl-4-(3-(2-methoxyphenyl)-3-oxo-2-azaprop-1-yl)-cyclohexane

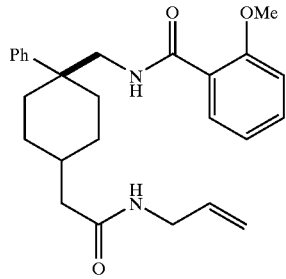

To a solution of 1-carboxymethyl-4-phenyl-4-(3-(2-methoxyphenyl)-3-oxo-2-azaprop-1-yl)-cyclohexane Example 185, 0.17 mmole) in 5 mL of $CH_2Cl_2$ was added EDC (48.1 mg, 0.25 mmol), DMAP (51.3 mg, 0.42 mmol) and allylamine (0.047 mL, 0.34 mmol). After it was stirred at rt for 60 h, the mixture was filtered through a plug of silica gel, concentrated and the residue was purified by HPLC (Waters RCM, $\mu$ Porosil, 25 mm×10 cm) using a mixture of (5:4:1 hexane-methyl tert-butyl ether-acetonitrile:hexane, 9.9/2.0 mL/min) to give the title compound as isomers #1 and #2.

Spectra data for isomer #1: $^1$H NMR (CDCl$_3$) δ 8.16 (d, 1H, J=7.7 Hz), 7.53 (bs, 1H), 7.34–7.42 (m, 5H), 7.26 (t, 1H, J=6.7 Hz), 7.01 (t, 1H, J=7.3 Hz), 6.81 (d, 1H, J=8.2 Hz), 6.22 (t, 1H, J=5.3 Hz), 5.79–5.87 (m, 1H), 5.17 (d, 1H, J=17.1 Hz), 5.09 (d, 1H, J=10.3 Hz), 3.86–3.88 (m, 4H), 3.46 (s, 3H), 2.19 (d, 2H, J=7.1 Hz), 2.09 (d, 2H, J=13.0 Hz), 1.44–1.92 (m, 7H); Mass Spectrum (CI) m/e 421 (M+1).

Spectra data for isomer #2: $^1$H NMR (CDCl$_3$) δ 8.12 (d, 1H, J=7.8 Hz), 7.56 (bs, 1H), 7.21–7.37 (m, 6H), 6.96 (t, 1H, J=7.5 Hz), 6.85 (d, 1H, J=8.3 Hz), 6.15 (t, 1H, J=5.4 Hz), 5.69–5.77 (m, 1H), 5.08 (d, 1H, J=17.2 Hz), 5.02 (d, 1H, J=10.3 Hz), 3.76 (t, 2H, J=5.5 Hz), 3.63 (s, 3H), 3.47 (d, 2H, J=5.9 Hz), 2.36 (d, 2H, J=12.8 Hz), 0.93–1.91 (m, 7H); Mass Spectrum (CI) m/e 421 (M+1).

EXAMPLES 186 AND 187

4-Phenyl-4-(3-(2-methoxyphenyl)-3-oxo-2-azaprop-1-yl)-cyclohexyl-1-oxirane

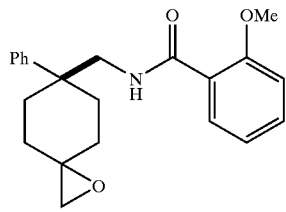

A solution of 1-methylidene-4-phenyl-4-(3-(2-methoxyphenyl)-3-oxo-2-azaprop-1-yl)cyclohexane (Example 165, 51.7 mg, 0.15 mmol) and mCPBA (106 mg, 0.62 mmol) in 5 mL of $CH_2Cl_2$ was stirred at rt for 16 h. It was then poured into ether and washed with $K_2CO_3$ (2×) and brine (1×), dried over MgSO$_4$, filtered through a plug of silica gel and concentrated. The residue was purified by HPLC (Waters RCM, $\mu$ Porosil, 25 mm×10 cm) using a mixture of (5:4:1 hexane-methyl tert-butyl ether-acetonitrile:hexane, 7.75/8.0 mL/min) to give the title compound, isomers #1 and #2.

Spectrum data for isomer #1: $^1$H NMR (CDCl$_3$) δ 8.20 (d, 1H, J=7.8 Hz), 7.62 (bs, 1H), 7.28–7.47 (m, 6H), 7.03 (t, 1H, J=7.5 Hz), 6.85 (d, 1H, J=8.2 Hz), 3.80 (d, 2H, J=6.2 Hz), 3.56 (s, 3H), 2.64 (s, 2H), 1.58–2.31 (m, 8H). Mass Spectrum (CI) m/e 352 (M+1).

Spectrum data for isomer #2: $^1$H NMR (CDCl$_3$) δ 8.19 (d, 1H, J=7.8 Hz), 7.63 (bs, 1H), 7.37–7.48 (m, 5H), 7.31 (t, 1H, J=7.1 Hz), 7.03 (t, 1H, J=7.1 Hz), 6.88 (d, 1H, J=8.2 Hz), 3.68 (d, 2H, J=5.9 Hz), 3.66 (s, 3H), 2.57 (s, 2H), 1.39–2.33 (m, 8H); Mass Spectrum (CI) m/e 352 (M+1).

EXAMPLE 188

1-(But-3-en-1-yl)-1-hydroxy-4-phenyl-4-(3-(2-methoxyphenyl)-3-oxo-2-azaprop-1-yl)-cyclohexane: Isomer 2

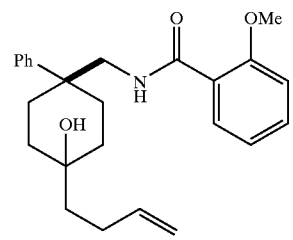

To a solution of 14-phenyl-4-(3-(2-methoxyphenyl)-3-oxo-2-azaprop-1-yl)-cyclohexyl-1-oxirane (isomer #2, Example 189, 15.8 mg, 0.045 mmol) in 2 mL of THF was added allylmagnesium bromide (0.22 mL, 1N, 0.22 mmol) and the reaction mixture was stirred at rt for 100 min. The mixture was quenched with pH=7 buffer, filtered through silica gel and concentrated. The residue was purified by HPLC (Waters RCM, $\mu$ Porosil, 25 mm×10 cm) using a mixture of (5:4:1 hexane-methyl tert-butyl ether-acetonitrile:hexane, 7.75/6.0 mL/min) to give the title compound.

$^1$H NMR (CDCl$_3$) δ 8.21 (d, 1H, J=7.8 Hz), 7.60 (bs, 1H), 7.39–7.46 (m, 5H), 7.29 (t, 1H, J=7.3 Hz), 7.05 (t, 1H, J=7.3 Hz), 6.88 (d, 1H, J=8.4 Hz), 5.74–5.82 (m, 1H), 4.97 (d of d, 1H, J=17.2, 1.6 Hz), 4.90 (d, 1H, J=10.3 Hz), 3.67 (s, 3H), 3.61 (d, 2H, J=5.9 Hz), 1.35–2.20 (m, 13H); Mass Spectrum (CI) m/e 394 (M+1).

EXAMPLE 189

1-(But-3-en-1-yl)-1-hydroxy-4-phenyl-4-(3-(2-methoxyphenyl)-3-oxo-2-azaprop-1-yl)-cyclohexane: Isomer 1

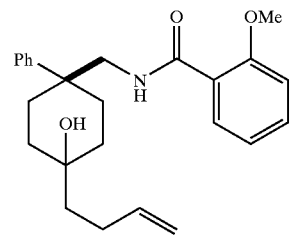

The title compound was prepared from 4-phenyl-4-(3-(2-methoxyphenyl)-3-oxo-2-azaprop-1-yl)-cyclohexyl-1- oxirane (isomer # 1, Example 189 (26.5 mg, 0.075 mmol) as described in Example 190.

¹H NMR (CDCl₃) δ 8.19 (d, 1H, J=7.7 Hz), 7.56 (bs, 1H), 7.36–7.46 (m, 5H), 7.28 (t, 1H, J=7.1 Hz), 7.03 (t, 1H, J=7.6 Hz), 6.83 (d, 1H, J=8.5 Hz), 5.84–5.92 (m, 1H), 5.03 (d, 1H, J=17.2 Hz), 4.97 (d, 1H, J=10.1 Hz), 3.80 (d, 2H, J=6.0 Hz), 3.51 (s, 3H), 1.58–2.23 (m, 13H); Mass Spectrum (CI) m/e 394 (M+1).

EXAMPLE 190

4-Phenyl-4-(3-(2-methoxyphenyl)-3-oxo-2-azaprop-1-yl)-cyclohex-1-ene

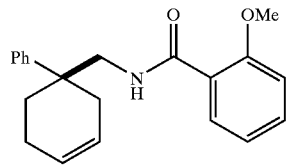

A solution of trans-1-methanesulfonyloxy-4-phenyl-4-(3-(2-methoxyphenyl)-3-oxo-2-azaprop-1-yl)cyclohexane (Example 154, 20.6 mg, 0.049 mmol) and NaI (24.2 mg, 0.16 mmol) in 5 mL of HMPA was heated at 120° C. for 14 h. The mixture was poured into ether, washed with Na₂S₂O₃ (1×) and brine (3×), dried over Na₂SO₄, filtered through a plug of silica gel and concentrated. The residue was purified by HPLC (Waters RCM, μ Porosil, 25 mm×10 cm) using a mixture of (5:4:1 hexane-methyl tert-butyl ether-acetonitrile:hexane, 7.75/8.0 mL/min) to give the title compound.

¹H NMR (CDCl₃) δ 8.20 (d, 1H, J=7.4 Hz), 7.61 (bs, 1H), 7.27–7.45 (m, 6H), 7.03 (t, 1H, J=7.6 Hz), 6.84 (d, 1H, J=8.2 Hz), 5.66–5.78 (m, 2H), 3.82 (d of d, 1H, J=6.6, 13.5 Hz), 3.76 (d of d, 1H, J=6.6, 13.5 Hz), 3.53 (s, 3H), 2.55 (d, 1H, J=17.9 Hz), 2.35 (d, 1H, J=17.9 Hz), 1.80–2.22 (m, 6H); Mass Spectrum (CI) m/e 322 (M+1).

EXAMPLES 191 AND 192

4-Phenyl-4-(3-(2-methoxyphenyl)-3-oxo-2-azaprop-1-yl)-cyclohexyl-1-hydroxy-1-hydroxymethyl-acetone Acetal

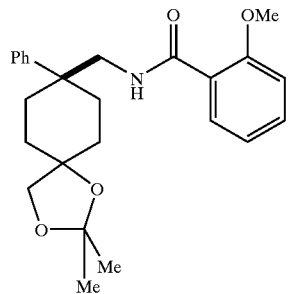

A solution of 1-hydroxy-1-hydroxymethyl-4-phenyl-4-(3-(2-methoxyphenyl)-3-oxo-2-azaprop-1-yl)-cyclohexane (Example 168, 18.5 mg, 0.05 mmol), dimethoxypropane (1.0 mL, 8.1 mmol) and TsOH H₂O (2.3 mg, 0.01 mmol) in 2 mL of DMF was stirred at rt for 14 h. The volatiles were removed and the residue was filtered through silica gel and concentrated. The residue was purified by HPLC (Waters RCM, μ Porosil, 25 mm×10 cm) using a mixture of (5:4:1 hexane-methyl tert-butyl ether-acetonitrile:hexane, 4.5/8.0 mL/min) to give the title compound as isomers #1 and #2.

Spectrum data for isomer #1: ¹H NMR (CDCl₃) δ 8.21 (d, 1H, J=7.8 Hz), 7.58 (bs, 1H), 7.38–7.46 (m, 5H), 7.29 (t, 1H, J=8.3 Hz), 7.05 (t, 1H, J=7.4 Hz), 6.88 (d, 1H, J=8.5 Hz), 3.66 (d, 2H, J=5.9 Hz), 3.65 (s, 3H), 3.62 (s, 2H), 2.08–2.15 (m, 4H), 1.77 (d, 2H, J=13.5 Hz), 1.42–1.46 (m, 2H), 1.40 (s, 6H); Mass Spectrum (CI) m/e 410 (M+1).

Spectrum data for isomer #2: ¹H NMR (CDCl₃) δ 8.20 (d, 1H, J=7.8 Hz), 7.58 (bs, 1H), 7.38–7.45 (m, 5H), 7.27 (t, 1H, J=7.0 Hz), 7.04 (t, 1H, J=7.1 Hz), 6.86 (d, 1H, J=8.0 Hz), 3.86 (s, 2H), 3.70 (d, 2H, J=5.9 Hz), 3.58 (s, 3H), 1.69–2.27 (m, 8H), 1.35 (s, 6H); Mass Spectrum (CI) m/e 410 (M+1).

EXAMPLES 193 AND 194

4-Phenyl-4-(3-(2-methoxyphenyl)-3-oxo-2-azaprop-1-yl)-cyclohexyl-1-hydroxy-1-hydroxymethyl-sulfolane

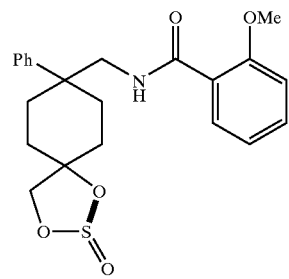

To a solution of 1-hydroxy-1-hydroxymethyl-4-phenyl-4-(3-(2-methoxyphenyl)-3-oxo-2-azaprop-1-yl)-cyclohexane (Example 168, 68.3 mg, 0.19 mmol) in 2.0 mL of pyridine was added SOCl₂ (0.2 mL) at 0° C. and the solution was stirred 0.5 h. The solution was poured into CH₂Cl₂ and washed with NaHCO₃, dried over Na₂SO₄, filtered, concentrated and purified by HPLC (Waters RCM, μ Porosil, 25 mm×10 cm) using a mixture of (5:4:1 hexane-methyl tert-butyl ether-acetonitrile:hexane, 3.15/8.0 to 9.0/0.0 mL/min) to give the separated iosmers.

Spectrum data for isomer #1: ¹H NMR (CDCl₃) δ 8.20 (d, 1H, J=7.8 Hz), 7.63 (bs, 1H), 7.31–7.46 (m, 6h), 7.05 (t, 1H, J=7.6 Hz), 6.90 (d, 1H, J=8.5 Hz), 4.30 (d, 1H, J=8.7 Hz), 4.01 (d, 1H, J=8.7 Hz), 3.68 (s, 3H), 3.58–3.67 (m, 2H), 2.03–2.36 (m, 5H), 1.84–1.87 (m, 1H), 1.76 (t, 1H, J=13.1 Hz), 1.44 (t, 1H, J=13.3 Hz); Mass Spectrum (CI) m/e 416 (M+1).

Spectrum data for isomer #2: ¹H NMR (CDCl₃) δ 8.18 (d, 1H, J=7.8 Hz), 7.62 (bs, 1H), 7.31–7.50 (m, 6H), 7.06 (t, 1H, J=8.0 Hz), 6.86 (d, 1H, J=7.8 Hz), 4.51 (d, 1H, J=8.6 Hz), 4.33 (d, 1H, J=8.6 Hz), 3.80 (d, 2H, J=5.3 Hz), 3.55 (s, 3H), 1.84–2.31 (m, 8H); Mass Spectrum (CI) m/e 416 (M+1).

EXAMPLE 195

1-Hydroxymethyl-4-phenyl-4-(3-(2-methoxyphenyl)-3-oxo-2-azaprop-1-yl)-cyclohexane

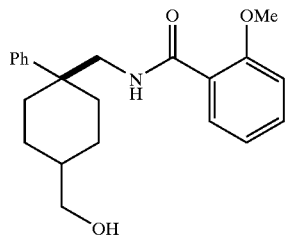

To a solution of 1-methylidene-4-phenyl-4-(3-(2-methoxyphenyl)-3-oxo-2-azaprop-1-yl)cyclohexane (Example 165, 117 mg, 0.35 mmol) was added 9-BBN (7 mL, 0.5 N, 3.5 mmol) in THF. The reaction mixture was stirred at rt for 1 h, and then heated to 45° C. for 3 h. To the solution was then added NaOH (3 mL, 10%) and $H_2O_2$ (4 mL, 30%) and the mixture was heated at 45° C. for 14 h. The reaction mixture was poured into $CH_2Cl_2$ and washed with 2N HCl and dried over $Na_2SO_4$, filtered and concentrated. The residue was purified by flash chromatography (silica, EtOAc/hexane, 2:1) to give the title compound as a 2:1 mixture of two diastereomers.

Mass Spectrum (CI) m/e 354 (M+1).

EXAMPLES 196 AND 197

1-(N-Allylcarbamoyloxymethyl)-4-phenyl-4-(3-(2-methoxyphenyl)-3-oxo-2-azaprop-1-yl)-cyclohexane

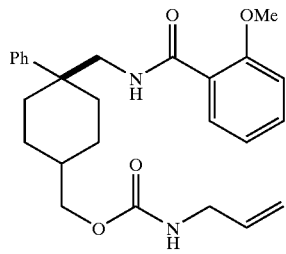

To a solution of the isomeric mixture of 1-hydroxymethyl-4-phenyl-4-(3-(2-methoxyphenyl)-3-oxo-2-azaprop-1-yl)-cyclohexane (Example 197, 32.6 mg, 0.092 mmol) in 2 mL of $CH_2Cl_2$ was added DMAP (28.2 mg, 0.23 mmol) and 4-nitrobenzylchloroformate (37.2 mg, 0.18 mmol) and the reaction mixture was stirred at rt for 16 h. Allyl amine (0.5 mL) was then added and the reaction mixture was stirred at rt for 30 min. The volatiles were removed and the residue was dissolved in ether and washed with 2N HCl, then $NaHCO_3$ and brine, dried over $Na_2SO_4$, filtered through silica gel, filtered and concentrated. The residue was purified by HPLC (Waters RCM, μ Porosil, 25 mm×10 cm) using a mixture of (5:4:1 hexane-methyl tert-butyl ether-acetonitrile:hexane, 4.5/8.0 mL/min) to give the separate isomers of the title compound.

Spectra data for isomer #1: $^1$H NMR (CDCl$_3$) δ 8.19 (d, 1H, J=7.8 Hz), 7.53 (bs, 1H), 7.35–7.45 (m, 5H), 7.29 (t, 1H, J=6.9 Hz), 7.03 (t, 1H, J=7.8 Hz), 6.82 (d, 1H, J=8.5 Hz), 5.83–5.91 (m, 1H), 5.21 (d of d, 1H, J=17.1, 1.3 Hz), 5.14 (d of d, 1H, J=10.3, 1.4 Hz), 4.88 (bs, 1H), 4.03 (d, 2H, J=5.2 Hz), 3.89 (d, 2H, J=5.8 Hz), 3.82 (bs, 1H), 3.49 (s, 3H), 2.16 (d, 2H, J=13.0 Hz), 1.54–1.77 (m, 7H); Mass Spectrum (CI) m/e 437 (M+1).

Spectra data for isomer #2: $^1$H NMR (CDCl$_3$) δ 8.20 (d, 1H, J=7.8 Hz), 7.57 (bs, 1H), 7.35–7.44 (m, 6H), 7.04 (t, 1H, J=7.6 Hz), 6.88 (d, 1H, J=8.2 Hz), 5.80–5.84 (m, 1H), 5.15 (d, 1H, J=17.2 Hz), 5.09 (d, 1H, J=9.9 Hz), 4.82 (bs, 1H), 3.77–3.79 (m, 3H), 3.64 (s, 3H), 3.56 (d, 2H, J=6.0 Hz), 2.44 (d, 2H, J=13.0 Hz), 1.01–1.74 (m, 7H); Mass Spectrum (CI) m/e 437 (M+1).

EXAMPLE 198

1-Acetoxymethyl-4-phenyl-4-(3-(2-methoxyphenyl)-3-oxo-2-azaprop-1-yl)-cyclohex-1-ene

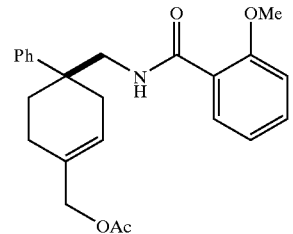

To a solution of 1-hydroxy-1-acetoxymethyl)-4-phenyl-4-(3-(2-methoxyphenyl)-3-oxo-2-azaprop-1-yl)-cyclohexane (Example 171, isomer #1, 19.5 mg, 0.047 mmol) in 2 mL of pyridine was added $SOCl_2$ (0.2 mL, 2.7 mmol) at 0° C. and the mixture was stirred at rt for 1 h. It was then poured into $NaHCO_3$, extracted with $CH_2Cl_2$ (2×), dried over $MgSO_4$ filtered and concentrated. The residue was purified by HPLC (Waters RCM, μ Porosil, 25 mm×10 cm) using a mixture of (5:4:1 hexane-methyl tert-butyl ether-acetonitrile:hexane, 7.75/6.0 mL/min) to give the title compound. $^1$H NMR (CDCl$_3$) δ 8.18 (d, 1H, J=7.8 Hz), 7.60 (bs, 1H), 7.26–7.41 (m, 6H), 7.03 (t, 1H, J=7.6 Hz), 6.83 (d, 1H, J=8.3 Hz), 5.81 (s, 1H), 4.39–4.45 (m, 2H), 3.80 (d of d, 1H, J=6.4, 13.2 Hz), 3.75 (d of d, 1H, J=6.4, 13.2 Hz), 3.15 (s, 3H), 2.61 (d, 1H, J=17.7 Hz), 2.38 (d, 1H, J=17.7), 2.04 (s, 3H), 1.77–2.16 (m, 4H); Mass Spectrum (CI) m/e 394 (M+1).

EXAMPLES 199 AND 200

1-Acetoxymethyl-4-phenyl-4-(3-(2-methoxyphenyl)-3-oxo-2-azaprop-1-yl)-cyclohexane

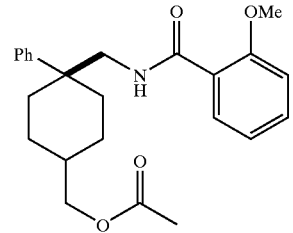

A solution of 1-acetoxymethyl-4-phenyl-4-(3-(2-methoxyphenyl)-3-oxo-2-azaprop-1-yl)-cyclohex-1-ene (Example 200, 11.5 mg, 0.029 mmol) in 5 mL of EtOAc was shaken with Pd/C (5 mg, 10%) under 50 psi of hydrogen for 14 h. The mixture was filtered through silica gel, concentrated and purified by HPLC (Waters RCM, μ Porosil, 25 mm×10 cm) using a mixture of (5:4:1 hexane-methyl tert-butyl ether-acetonitrile:hexane, 4.5/8.0 mL/min) to give the 2 isomers of the title compound Isomer #1: $^1$H NMR (CDCl$_3$) δ 8.20 (d, 1H, J=8.0 Hz), 7.53 (bs, 1H), 7.28–7.46 (m, 6H), 7.04 (t, 1H, J=7.6 Hz), 6.83 (d, 1H, J=8.2 Hz), 4.02 (d, 2H, J=6.4 Hz), 3.89 (d, 2H, J=5.8 Hz), 3.50 (s, 3H), 2.16 (d, 2H, J=12.9 Hz), 2.09 (s, 3H), 1.56–1.79 (m, 6H); Mass Spectrum (CI) m/e 396 (M+1).

Isomer #2 (CDCl$_3$) δ 8.21 (d, 1H, J=7.8 Hz), 7.57 (bs, 1H), 7.27–7.43 (m, 6H), 7.06 (t, 1H, J=7.1 Hz), 6.89 (d, 1H, J=8.3 Hz), 3.78 (d, 2H, J=6.6 Hz), 3.67 (s, 3H), 3.58 (d, 2H, J=5.9 Hz), 3.50 (s, 3H), 2.46 (d, 2H, J=12.6 Hz), 2.01 (s, 3H), 1.59–1.81 (m, 5H), 0.99–1.07 (m, 2H); Mass Spectrum (CI) m/e 396 (M+1).

EXAMPLES 201 AND 202 cis and trans-1,2-Epoxy-4-phenyl-4-(3-(2-methoxyphenyl)-3-oxo-2-azaprop-1-yl)-cyclohexane

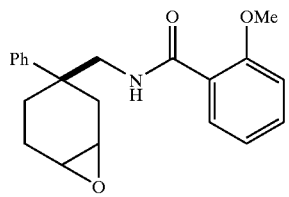

A solution of 4-phenyl-4-(3-(2-methoxyphenyl)-3-oxo-2-azaprop-1-yl)-cyclohex-1-ene (Example 192, 146.3 mg, 0.46 mmol) and mCPBA (156.8 mg, 0.92 mmol) in 8.0 mL of CH$_2$Cl$_2$ was stirred at rt for 18 h. The reaction mixture was poured into ether, washed with NaHCO$_3$ (3×), dried over Na$_2$SO$_4$, filtered through a plug of silica gel and concentrated The residue was purified by HPLC (Waters RCM, μ Porosil, 25 mm×10 cm) using a mixture of (5:4:1 hexane-methyl tert-butyl ether-acetonitrile:hexane, 1.0/8.0 mL/min) to give the separated cis and trans isomers.

Spectrum data for cis isomer, $^1$H NMR (CDCl$_3$) δ 8.17 (d, 1H, J=7.8 Hz), 7.60 (bs, 1H), 7.35–7.44 (m, 5H), 7.30 (t, 1H, J=7.1 Hz), 7.02 (t, 1H, J=7.1 Hz), 6.84 (d, 1H, J=8.2 Hz), 3.84 (d of d, 1H, J=13.5, 8.0 Hz), 3.54 (s, 3H), 3.48 (d of d, 1H, J=13.5, 3.7 Hz), 3.31 (d of d, 1H, J=5.5, 4.3 Hz), 2.98 (m, 1H), 2.69 (d of d of d, 1H, J=15.7, 5.7, 2.5 Hz), 2.02 (d, 1H, J=16.0 Hz), 1.94 (d, 1H, J=15.1 Hz), 1.77 (t of d, 1H, J=13.1, 4.5 Hz), 1.68–1.71 (m, 1H), 1.32–1.39 (m, 1H); Mass Spectrum (CI) m/e 338 (M+1).

Spectrum data for trans isomer, $^1$H NMR (CDCl$_3$) δ 8.19 (d, 1H, J=7.8 Hz), 7.61 (bs, 1H), 7.27–7.43 (m, 6H), 7.05 (t, 1H, J=8.0 Hz), 6.84 (d, 1H, J=8.2 Hz), 3.94 (d of d, 1H, J=13.7, 6.6 Hz), 3.71 (d of d, 1H, J=13.8, 4.9 Hz), 3.49 (s, 3H), 3.34 (m, 1H), 3.27 (t, 1H, J=4.3 Hz), 2.29 (d of d, 1H, J=15.6, 5.5 Hz), 2.13–2.24 (m, 3H), 1.79–1.84 (m, 2H); Mass Spectrum (CI) m/e 338 (M+1).

EXAMPLE 203 cis-1-Hydroxy-2-trans-allyl-4-phenyl-4-(3-(2-methoxyphenyl)-3-oxo-2-azaprop-1-yl)-cyclohexane

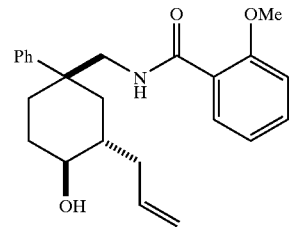

To a solution of cis-1,2-epoxy-4-phenyl-4-(3-(2-methoxyphenyl)-3-oxo-2-azaprop-1-yl)-cyclohexane (Example 203, 11.5 mg, 0.034 mmol) in 2.0 mL of THF was added allyl magnesium bromide (0.4 mL, 1N, 0.4 mmol) and the mixture was stirred at rt for 3 h. It was quenched with 4 drops of pH=7 buffer, filtered through a plug of silica gel and concentrated. The residue was purified by HPLC (Waters RCM, μ Porosil, 25 mm×10 cm) using a mixture of (5:4:1 hexane-methyl tert-butyl ether-acetonitrile:hexane, 4.5/6.0 mL/min) to give the title compound.

$^1$H NMR (CDCl$_3$) δ 8.20 (d, 1H, J=7.8 Hz), 7.61 (bs, 1H), 7.27–7.45 (m, 6H), 7.05 (t, 1H, J=7.3 Hz), 6.88 (d, 1H, J=8.2 Hz), 5.73–5.81 (m, 1H), 4.98 (d, 1H, J=15.6 Hz), 4.96 (d, 1H,=9.1 Hz), 3.67 (s, 3H), 3.63 (d of d, 1H, J=13.0, 6.2 Hz), 3.56 (d of d, 1H, J=13.3, 5.9 Hz), 3.32 (t of d, 1H, J=10.7, 3.0 Hz), 2.66 (d of t, 1H, J=13.3, 2.9 Hz), 2.36–2.45 (m, 2H), 1.99 (bs, 1H), 1.40–1.82 (m, 5H), 0.97 (q, 1H, J=14.6 Hz); Mass Spectrum (CI) m/e 380 (M+1).

EXAMPLE 204 cis-1-Hydroxy-3-phenyl-3-(3-(2-methoxyphenyl)-3-oxo-2-azaprop-1-yl)-cyclohexane

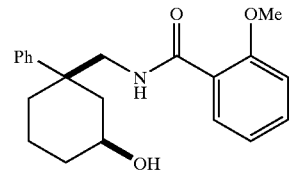

To a solution of cis-1,2-epoxy-4-phenyl-4-(3-(2-methoxyphenyl)-3-oxo-2-azaprop-1-yl)-cyclohexane (Example 203, 11.4 mg, 0.034 mmol) in 2.0 mL of iPrOH was added NaBH$_4$ (25.4 mg, 0.68 mmol) and the reaction mixture was heated at 90° C. for 8 h. It was then diluted with CH$_2$Cl$_2$, filtered through a plug of silica gel and concentrated. The residue was purified by HPLC (Waters RCM, μ Porosil, 25 mm×10 cm) using a mixture of (5:4:1 hexane-methyl tert-butyl ether-acetonitrile:hexane, 4.5/6.0 mL/min) to give the title compound.

$^1$H NMR (CDCl$_3$) δ 8.19 (d, 1H, J=7.8 Hz), 7.63 (bs, 1H), 7.26–7.44 (m, 6H), 7.05 (t, 1H, J=7.6 Hz), 6.88 (d, 1H, J=8.3 Hz), 3.72 (d of d, 1H, J=13.3, 6.0 Hz), 3.68 (m, 1H), 3.65 (s, 3H), 3.56 (d of d, 1H, J=13.3, 5.7 Hz), 2.57 (d, 1H, J=12.9 HZ), 2.27 (d, 1H, J=13.3 Hz), 1.29–1.87 (m, 7H); Mass Spectrum (CI) m/e 340 (M+1).

EXAMPLE 205 cis-1-Acetoxy-3-phenyl-3-(3-(2-methoxyphenyl)-3-oxo-2-azaprop-1-yl)-cyclohexane

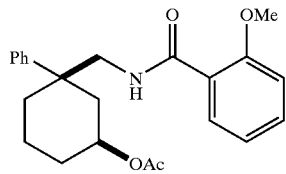

To a solution of cis-1-hydroxy-3-phenyl-3-(3-(2-methoxyphenyl)-3-oxo-2-azaprop-1-yl)-cyclohexane (Example 206, 6.0 mg, 0.018 mmol) in 2.0 mL of $CH_2Cl_2$ was added DMAP (2 mg, 0.016 mmol), pyridine (0.04 mL, 0.49 mmol) and $Ac_2O$ (0.02 mL, 0.21 mmol) and the mixture was stirred at rt for 14 h. The volatiles were removed, and the residue was purified by flash chromatography (silica, EtOAc/hexane, 3:7) to give the title compound.

$^1$H NMR (CDCl$_3$) δ 8.19 (d, 1H, J=7.8 Hz), 7.57 (bs, 1H), 7.53 (d, 2H, J=7.3 Hz), 7.44 (t, 2H, J=7.6 Hz), 7.41 (t, 1H, J=7.1 Hz), 7.29 (t, 1H, J=7.3 Hz), 7.05 (t, 1H, J=7.1 Hz), 6.88 (d, 1H, J=8.3 Hz), 4.74–4.81 (m, 1H), 3.70 (d of d, 1H, J=13.2, 6.8 Hz), 3.66 (s, 3H), 3.52 (d of d, 1H, J=13.3, 5.3 Hz), 2.73 (d, 1H, J=11.4 Hz), 2.35 (d, 1H, J=13.7 Hz), 2.04 (s, 3H), 1.26–1.91 (m, 6H); Mass Spectrum (CI) m/e 382 (M+1).

EXAMPLE 206

3-Phenyl-3-(3-(2-methoxyphenyl)-3-oxo-2-azaprop-1-yl)-cyclohexanone

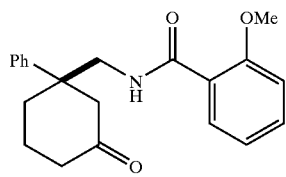

A solution of cis-1-hydroxy-3-phenyl-3-(3-(2-methoxyphenyl)-3-oxo-2-azaprop-1-yl)-cyclohexane (Example 206, (18.0 mg, 0.053 mmol) and PCC (42 mg, 0.020 mmol) in 3.0 mL of $CH_2Cl_2$ was stirred at rt for 80 min. The volatiles were removed and the residue was purified by flash chromatography (silica, acetone/hexane, 1:2) to give the title compound.

$^1$H NMR (CDCl$_3$) δ 8.16 (d, 1H, J=7.8 Hz), 7.61 (bs, 1H), 7.27–7.42 (m, 6H), 7,53 (t, 1H, J=7.5 Hz), 6.85 (d, 1H, J=8.3 Hz), 3.92 (d of d, 1H, J=13.5, 7.3 Hz), 3.66 (d of d, 1H, J=13.5, 4.5 Hz), 3.56 (s, 3H), 3.06 (d, 1H, J=14.8 Hz), 2.58 (d, 1H, J=14.8 Hz), 1.51–2.37 (m, 6H); Mass Spectrum (CI) m/e 338 (M+1).

EXAMPLE 207 cis-1-N-Allylcarcamoyloxy-3-phenyl-3-(3-(2-methoxyphenyl)-3-oxo-2-azaprop-1-yl)-cyclohexane

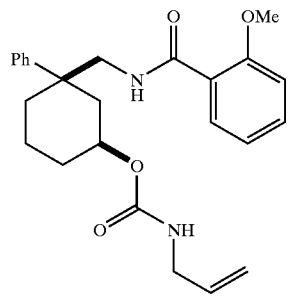

The title compound was prepared from cis-1-hydroxy-3-phenyl-3-(3-(2-methoxyphenyl)-3-oxo-2-azaprop-1-yl)-cyclohexane as described in Example 198.

$^1$H NMR (CDCl$_3$) δ 8.17 (d, 1H, J=8.0 Hz), 7.61 (bs, 1H), 7.52 (d, 2H, J=7.6 Hz), 7.43 (t, 2H, J=7.3 Hz), 7.39 (t, 1H, J=7.1 Hz), 7.28 (t, 1H, J=7.3 Hz), 7.03 (t, 1H, J=7.1 Hz), 6.87 (d, 1H, J=8.3 Hz), 5.79–5.87 (m, 1H), 5.18 (d, 1H, J=17.1 Hz), 5.09 (d, 1H, J=10.3 Hz), 4.71–4.77 (m, 1H), 3.78–3.84 (m, 4H), 3.63 (s, 3H), 3.50 (d of d, 1H, J=13.3, 4.6 Hz), 2.68 (d, 1H, J=10.3), 2.24 (d, 1H, J=12.4 Hz), 1.27–1.87 (m, 6H); Mass Spectrum (CI) m/e 423 (M+1).

EXAMPLE 208 trans 1-(N-((2-Hydroxy-1,1-dimethyl)ethyl)carbamoyloxy)-4-phenyl-4-(3-(2-methoxyphenyl)-3-oxo-2-azapropyl)cyclohexane

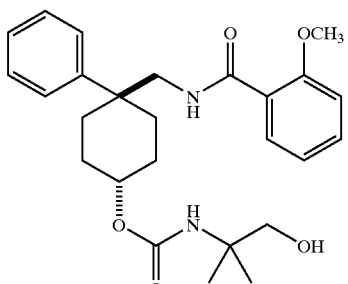

$^1$H NMR (CDCl$_3$) δ 1.2 (br s, 6H), 1.45 (m, 2H), 1.7 (m, 2H), 1.9 (m, 2H), 2.3 (m, 2H), 3.52 (s, 2H), 3.60 (m, 6H), 4.68 (brs, 1H), 4.85 (br s, 1H), 6.85 (d, 1H), 7.0 (t, 1H), 7.27 (m, 1H), 7.4 (m, 4H), 7.58 (t, 1H), 8.16 (dd, 1H); Mass Spectrum (PB-NH3/CI): m/e 455 (M+1).

EXAMPLE 209 trans 1-(N-((2-Hydroxy-1-(S)-t-butyl)ethyl)
carbamoyloxy)-4-phenyl-4-(3-(2-methoxyphenyl)-3-
oxo-2-azapropyl)cyclohexane

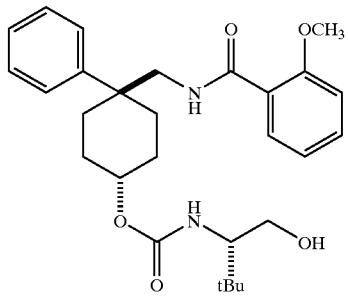

$^1$H NMR (CDCl$_3$) δ 0.8 (s, 9H), 1.42 (m, 2H), 1.68 (m, 2H), 1.9 (m, 2H), 2.28 (m, 2H), 3.44 (m, 2H), 3.58 (m, 5H), 3.75 (m, 1H), 4.70 (brs, 1H), 4.83 (br s, 1H), 6.83 (d, 1H), 6.9 (t, 1H), 7.26 (m, 1H), 7.4 (m, 4H), 7.6 (t, 1H), 8.16 (dd, 1H); Mass Spectrum (PB-NH3/CI): m/e 483 (M+1).

EXAMPLE 210 trans 1-(N-((R)-Prolinolyl)carbamoyloxy)-4-phenyl-
4-(3-(2-methoxyphenyl)-3-oxo-2-azapropyl)
cyclohexane

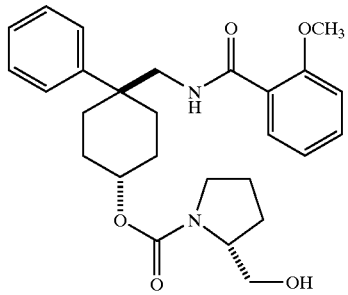

$^1$H NMR (CDCl$_3$) δ 1.4–2.35 (m, 12H), 3.22 (m, 2H), 3.35 (m, 2H), 3.5–3.7 (m, 6H), 4.80 (brs, 1H), 6.85 (d, 1H), 7.2 (t, 1H), 7.3 (m, 1H), 7.42 (m, 4H), 7.58 (t, 1H), 8.18 (dd, 1H); Mass Spectrum (PB-NH3/CI): m/e 467 (M+1).

EXAMPLE 211 trans 1-(N-((S)-Prolinolyl)carbamoyloxy)-4-phenyl-
4-(3-(2-methoxyphenyl)-3-oxo-2-azapropyl)
cyclohexane

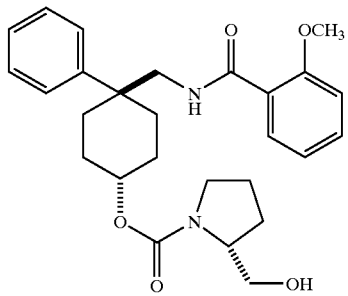

$^1$H NMR (CDCl$_3$) δ Same as for Example 212; Mass Spectrum (PB-NH3/CI): m/e 467 (M+1).

EXAMPLE 212 trans 1-(N-((S)-Isoleucinolyl)carbamoyloxy)-4-
phenyl-4-(3-(2-methoxyphenyl)-3-oxo-2-azapropyl)
cyclohexane

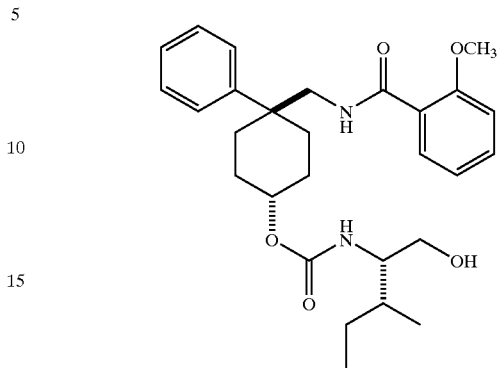

$^1$H NMR (CDCl$_3$) δ 0.8 (m, 6H), 1.06 (m, 1H), 1.44 (m, 3H), 1.55 (m, 1H), 1.7 (br t, 2H), 1.9 (m, 2H), 2.28 (br d, 2H), 3.46 (m, 2H), 3.6 (m, 6H), 4.70 (brs, 1H), 4.95 (d, 1H), 6.85 (d, 1H), 6.98 (t, 1H), 7.26 (m, 1H), 7.4 (m, 4H), 7.58 (t, 1H), 8.14 (dd, 1H); Mass Spectrum (PB-NH3/CI): m/e 483 (M+1).

EXAMPLE 213 trans 1-(N-((S)-Leucinolyl)carbamoyloxy)-4-phenyl-
4-(3-(2-methoxyphenyl)-3-oxo-2-azapropyl)
cyclohexane

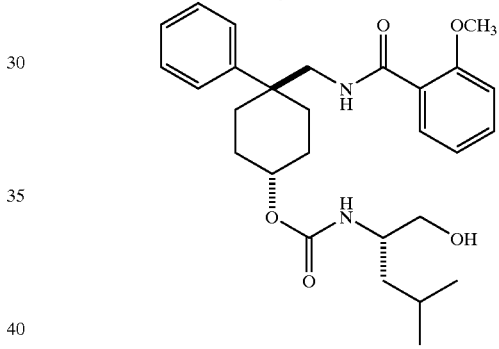

$^1$H NMR (CDCl$_3$) δ 0.86 (m, 6H), 1.26 (m, 3H), 1.44 (m, 2H), 1.58 (m, 1H), 1.7 (br t, 2H), 1.92 (m, 2H), 2.3 (br d, 2H), 3.46 (m, 2H), 3.6 (m, 4H), 3.7 (m, 2H), 4.70 (brs, 1H), 4.84 (d, 1H), 6.84 (d, 1H), 6.99 (t, 1H), 7.28 (m, 1H), 7.4 (m, 4H), 7.59 (t, 1H), 8.15 (dd, 1H); Mass Spectrum (PB-NH3/CI): m/e 483 (M+1).

EXAMPLE 214 trans 1-(N-((R)-Leucinolyl)carbamoyloxy)-4-
phenyl-4-(3-(2-methoxyphenyl)-3-oxo-2-azapropyl)
cyclohexane

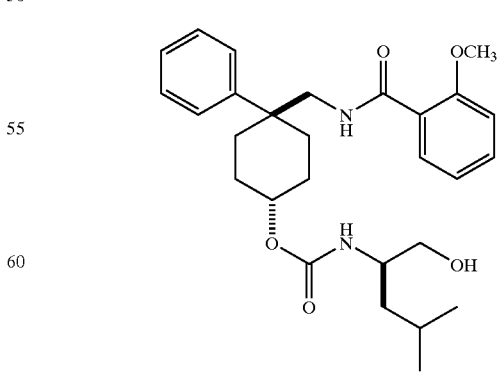

$^1$H NMR (CDCl$_3$) same as Example 215; Mass Spectrum (PB-NH3/CI): m/e 483 (M+1).

EXAMPLE 215 trans 1-(N-(Valinolyl)carbamoyloxy)-4-phenyl-4-(3-(2-methoxyphenyl)-3-oxo-2-azapropyl)cyclohexane

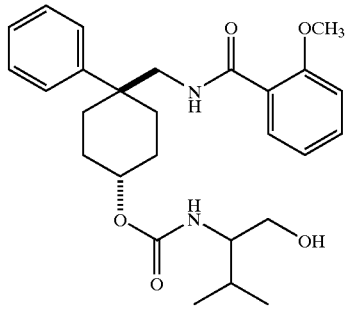

$^1$H NMR (CDCl$_3$) δ 0.86 (dd, 6H), 1.42 (m, 2H), 1.68 (m, 2H), 1.8 (m, 1H), 1.9 (m, 2H), 2.3 (br d, 2H), 3.4 (m, 2H), 3.6 (m, 6H), 4.70 (brs, 1H), 4.96 (d, 1H), 6.84 (d, 1H), 6.98 (t, 1H), 7.26 (m, 1H), 7.4 (m, 4H), 7.59 (br t, 1H), 8.15 (dd, 1H); Mass Spectrum (PB-NH3/CI): m/e 469 (M+1).

EXAMPLE 216 trans 1-N-(Norphenylephrinyl)carbamoyloxy)-4-phenyl-4-(3-(2-methoxyphenyl)-3-oxo-2-azapropyl)cyclohexane

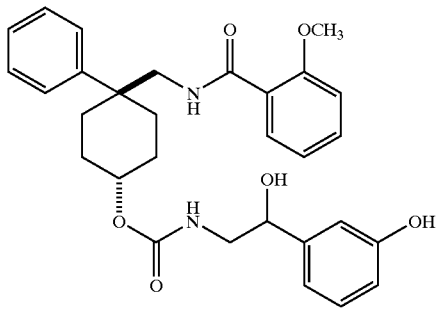

$^1$H NMR (CDCl$_3$) δ 1.36 (m, 2H), 1.59 (m, 2H), 1.8 (m, 2H), 2.2 (m, 2H), 3.2 (m, 2H), 3.4 (m, 2H), 3.56 (m, 1H), 3.6 (m, 3H), 4.60 (brs, 1H), 4.66 (br s, 1H), 6.76 (m, 1H), 6.85 (m, 2H), 7.0 (t, 1H), 7.26 (m, 1H), 7.4 (m, 6H), 7.64 (br t, 1H), 8.15 (d, 1H); Mass Spectrum (PB-NH3/CI): m/e 536 (M+1).

EXAMPLE 217 trans 1-(N-(Imidazol-2-ylmethyl)carbamoyloxy)-4-phenyl-4-(3-(2-methoxyphenyl)-3-oxo-2-azapropyl)cyclohexane

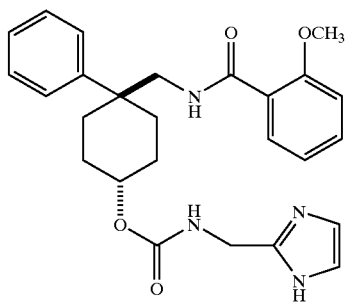

Step 1 trans 1-(N-(2-Oxoethyl)carbamoyloxy)-4-phenyl-4-(3-(2-methoxyphenyl)-3-oxo-2-azapropyl)cyclohexane

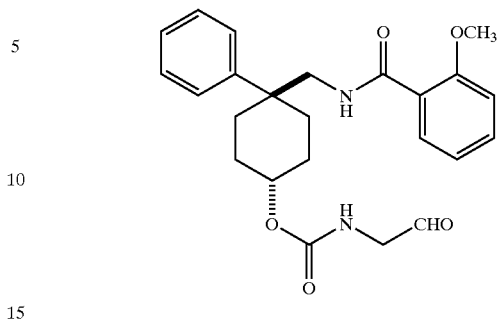

To a solution of 0.06 mL of oxalyl chloride (0.7 mmol) in 1 mL of CH$_2$Cl$_2$ at −78° C. was added dropwise 0.09 mL of DMSO (1.3 mmol). After stirring for 15 min, a solution of 0.224 gm of trans 1-(N-(2-hydroxyethyl)carbamoyloxy)-4-phenyl-4-(3-(2-methoxyphenyl)-3-oxo-2-azapropyl)cyclohexane (Example 13, 0.528 mmol) in 2 mL of CH$_2$Cl$_2$ was slowly added. After stirring for 1 hr, 0.37 mL of triethylamine (2.65 mmol) was added and the reaction mixture was allowed to warm to rt. After 1 hr, the reaction mixture was made acidic by addition of 1.6 mL of HCl in ether (1 M), and was then concentrated. The residue was dissolved in EtOAc, washed with water and brine, dried over Na$_2$SO$_4$, filtered and concentrated. The material was used without further purification.

Step 2 trans 1-(N-(Imidazol-2-ylmethyl)carbamoyloxy)-4-phenyl-4-(3-(2-methoxyphenyl)-3-oxo-2-azapropyl)cyclohexane To a solution of 0.093 gm of trans 1-(N-(2-oxoethyl)carbamoyloxy)-4-phenyl-4-(3-(2-methoxyphenyl)-3-oxo-2-azapropyl)cyclohexane (0.22 mmol) in 4 mL of methanol was added 0.75 mL of concentrated NH$_4$OH. After stirring for 15 min at rt, 0.25 mL of glyoxal (40%w/w, 2.2 mmol) was then added and the reaction mixture was stirred at rt for 12 hr. The reaction mixture was concentrated and redissolved in ethyl acetate. The ethyl acetate solution was washed with water, dried over Na$_2$SO$_4$, filtered and the filtrate was concentrated. The residue was purified by chromatography (HPLC, C18 NOVA RCM, 0.2% TFA in 20%–60% gradient of CH$_3$CN in H$_2$O) to give the title compound.

$^1$H NMR (CDCl$_3$) δ 1.4 (m, 2H), 1.7 (m, 2H), 1.84 (m, 2H), 2.28 (m, 2H), 3.2 (m, 2H), 3.62 (m, 3H), 3.66 (m, 5H), 4.60 (brs, 1H), 4.68 (br s, 1H), 6.9 (d, 1H), 7.04 (t, 1H), 7.1 (br s, 1H), 7.26 (m, 2H), 7.3 (t, 1H), 7.42 (m, 4H), 7.72 (m, 1H), 8.1 (d, 1H); Mass Spectrum (PB-NH3/CI): m/e 463 (M+1).

EXAMPLE 218 trans 1-(N-(2-Hydroxy-2-phenylethyl)carbamoyloxy)-4-phenyl-4-(3-(2-methoxyphenyl)-3-oxo-2-azapropyl)cyclohexane

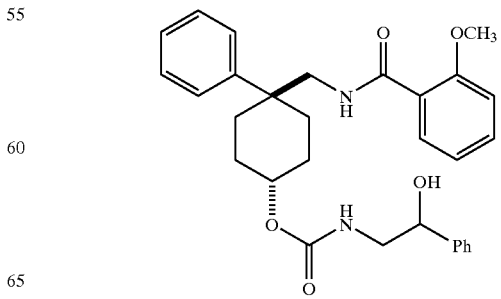

To a solution of 0.158 gm of trans 1-(N-(2-oxoethyl) carbamoyloxy)-4-phenyl-4-(3-(2-methoxyphenyl)-3-oxo-2-azapropyl)cyclohexane (Example 219, Step 1, 0.314 mmol) in 4 mL of THF at −78° C. was added 0.63 mL of phenyl magnesium bromide (Aldrich, 1M in THF, 0.63 mmol). After stirring for 2 hr, another 0.63 mL of phenyl magnesium bromide was added to complete the reaction. After two more hours, the reaction was quenched with NH$_4$Cl, and diluted with water. The mixture was extracted with EtOAc and the combined organic fractions were washed with water and brine, dried over Na$_2$SO$_4$, filtered and the filtrate was concentrated. The residue was purified by chromoatography (HPLC, NOVA RCM silica, 25% to 50% gradient of methyl-t-butyl ether:CH$_3$CN, 3:1 in hexanes) to give the title compound.

$^1$H NMR (CDCl$_3$) δ 1.5 (m, 2H), 1.75 (m, 2H), 1.95 (m, 2H), 2.3 (m, 2H), 3.26 (m, 2H), 3.5 (m, 2H), 3.64 (m, 5H), 4.68 (m, 1H), 5.0 (m, 1H), 6.88 (d, 1H), 7.04 (t, 1H), 7.1 (br s, 1H), 7.26 (m, 2H), 7.3 (t, 1H), 7.2–7.5 (m, 10H), 7.59 (m, 1H), 8.18 (d, 1H); Mass Spectrum (PB-NH3/CI): m/e 503 (M+1).

EXAMPLE 219 trans 1-(N-(2,3-Dihydroxypropyl)carbamoyloxy)-4-phenyl-4-(3-(2-methoxyphenyl)-3-oxo-2-azapropyl) cyclohexane

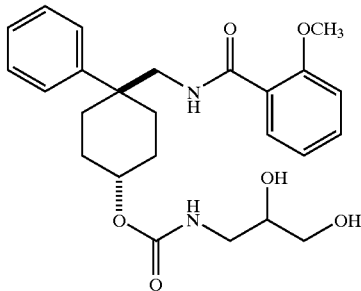

To a solution of 0.117 gm of trans 1-(N-allylcarbamoyloxy)-4-phenyl-4-(3-(2-methoxyphenyl)-3-oxo-2-azapropyl)cyclohexane (Example 28, 0.277 mmol) and 0.129 gm of N-methylmorpholine-N-oxide (1.1 mmol) in 10 mL of THF was added 0.07 mL Of OsO$_4$ (0.4 M in THF, 0.028 mmol). and the reaction mixture was stirred for 4 hr at rt. The reaction was quenched with 4 mL of sat. NaHSO$_3$ solution and the mixture was extracted with EtOAc. The combined organic fractions were washed with brine, dried over Na$_2$SO$_4$, filtered and the filtrate was concentrated. The residue was purified by chromatography (silica, 40% acetone:CH$_2$Cl$_2$) to give the title compound. $^1$H NMR (CDCl$_3$) δ 1.48 (m, 2H), 1.74 (m, 2H), 1.94 (m, 2H), 2.3 (m, 2H), 3.26 (m, 2H), 3.5–3.66 (m, 7H), 3.72 (m, 1H), 4.76 (m, 1H), 5.06 (m, 1H), 6.88 (d, 1H), 7.04 (t, 1H), 7.3 (m, 1H), 7.44 (m, 4H), 7.6 (m, 1H), 8.18 (dd, 1H); Mass Spectrum (PB-NH3/CI): m/e 457 (M+1).

EXAMPLE 220 trans 1-(N-(t-Butoxycarbonylmethyl) carbamoyloxy)-4-phenyl-4-(3-(2-methoxyphenyl)-3-oxo-2-azapropyl)cyclohexane

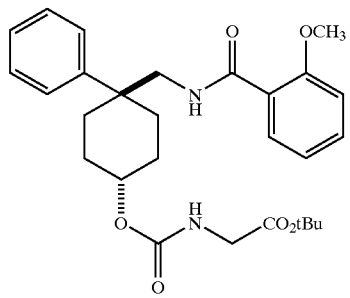

The title compound was prepared from trans 1-((4-Nitrophenoxy)carbonyloxy)-4-phenyl-4-(3-(2-methoxyphenyl)-3-oxo-2-azapropyl)cyclohexane (Example 2) according to procedures described in Example 3 using glycine t-butylester.

$^1$H NMR (CDCl$_3$) δ 1.48 (m, 2H), 1.76 (m, 2H), 1.94 (m, 2H), 2.16 (s, 9H), 2.3 (m, 2H), 3.26 (m, 2H), 3.5–3.66 (m, 7H), 3.72 (m, 1H), 4.76 (m, 1H), 5.06 (m, 1H), 6.88 (d, 1H), 7.04 (t, 1H), 7.3 (m, 1H), 7.44 (m, 4H), 7.6 (m, 1H), 8.18 (dd, 1H); Mass Spectrum (PB-NH3/CI): m/e 497 (M+1).

EXAMPLE 221 trans 1-(N-(Carboxymethyl)carbamoyloxy)-4-phenyl-4-(3-(2-methoxyphenyl)-3-oxo-2-azapropyl) cyclohexane

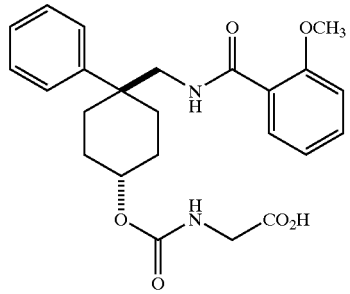

To a solution of 0.075 gm of trans 1-(N-(t-butoxycarbonylmethyl)carbamoyloxy)-4-phenyl-4-(3-(2-methoxyphenyl)-3-oxo-2-azapropyl)cyclohexane (Example 222, 0.15 mmol) in 1 mL of CH$_2$Cl$_2$ was added 0.4 mL of trifluoroacetic acid ((1.3 mmol) and the reaction mixture was stirred at rt for 4 hr. The reaction mixture was concentrated, redissolved in methanol, filtered through a pad of celite and reconcentrated to give the title compound which was used without further purification.

$^1$H NMR (CDCl$_3$) δ 1.6 (m, 2H), 1.76 (m, 2H), 1.94 (m, 2H), 2.3 (m, 2H), 3.64 (m, 6H), 3.68 (m, 2H), 4.76 (m, 1H), 5.06 (m, 1H), 6.89 (d, 1H), 7.06 (t, 1H), 7.18 (m, 1H), 7.44 (m, 4H), 7.8 (m, 1H), 8.14 (dd, 1H); Mass Spectrum (PB-NH3/CI): m/e 441 (M+1).

EXAMPLE 222 trans 1-(N-(Carbomethoxymethyl)carbamoyloxy)-4-phenyl-4-(3-(2-methoxyphenyl)-3-oxo-2-azapropyl)cyclohexane

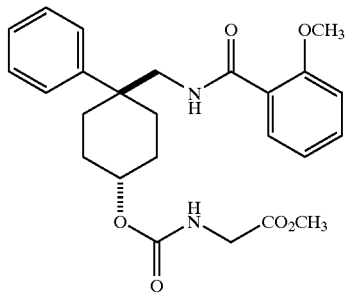

To a solution of 0.006 gm of trans 1-(N-(carboxymethyl) carbamoyloxy)-4-phenyl-4-(3-(2-methoxyphenyl)-3-oxo-2-azapropyl)cyclohexane (Example 223, 0.014 mmol) in 0.1 mL of $CH_2Cl_2$ and 0.1 1 mL of methanol was added 0.24 mL of trimethylsilyldiazomethane (Aldrich, 2M in hexanes, 0.48 mmol). After 1 hr, the reaction mixture was concentrated and purified by chromotography (HPLC, NOVA RCM silica, 80:20 to 100:0 75%/25% tBuOMe/$CH_3CN$ in hexanes) to give the title compound.

$^1$H NMR (CDCl$_3$) δ 1.52 (m, 2H), 1.76 (m, 2H), 1.94 (m, 2H), 2.32 (m, 2H), 3.64 (m, 6H), 3.74 (m, 3H), 3.94 (d, 2H), 4.79 (m, 1H), 5.02 (m, 1H), 6.88 (d, 1H), 7.03 (t, 1H), 7.3 (m, 1H), 7.44 (m, 4H), 7.59 (m, 1H), 8.2 (dd, 1H); Mass Spectrum (PB-NH3/CI): m/e 455 (M+1).

EXAMPLE 223 trans 1-(N-(N-Allylaminocarbonylmethyl)carbamoyloxy)-4-phenyl-4-(3-(2-methoxyphenyl)-3-oxo-2-azapropyl)cyclohexane

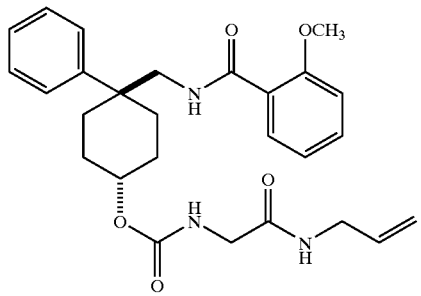

To a solution of 0.115 gm of trans 1-(N-(carboxymethyl)carbamoyloxy)-4-phenyl-4-(3-(2-methoxyphenyl)-3-oxo-2-azapropyl)cyclohexane (Example 223, 0.26 mmol) in 3 mL of $CH_2Cl_2$ at 0° C. was added 0.0635 gm of 1(3-dimethylaminopropyl)-3-ethyl-carbodiimide hydrochloride (Aldrich, 0.33 mmol). After stirring for 30 min, 0.025 mL of allylamine (0.33 mmol) was added and the reaction mixture was stirred for 12 hr at rt. The reaction mixture was diluted with ether and washed with 2N HCl, sat. NaHCO$_3$ and brine. The organic fraction was dried over MgSO$_4$, filtered and the filtrate was concentrated. The residue was purified by crystallization from ethyl acetate.

$^1$H NMR (CDCl$_3$) δ 1.52 (m, 2H), 1.75 (m, 2H), 1.96 (m, 2H), 2.32 (m, 2H), 3.62 (m, 3H), 3.65 (m, 3H), 3.82 (m, 2H), 3.9 (m, 2H), 4.8 (m, 1H), 5.15 (m, 1H), 5.8 (m, 1H), 6.1 (m, 2H), 6.84 (d, 1H), 7.05 (t, 1H), 7.3 (m, 1H), 7.44 (m, 4H), 7.59 (m, 1H), 8.2 (dd, 1H); Mass Spectrum (PB-NH3/CI): m/e 480 (M+1).

EXAMPLE 224 trans 1-(N-(N-Benzylaminocarbonylmethyl)carbamoyloxy)-4-phenyl-4-(3-(2-methoxyphenyl)-3-oxo-2-azapropyl)cyclohexane

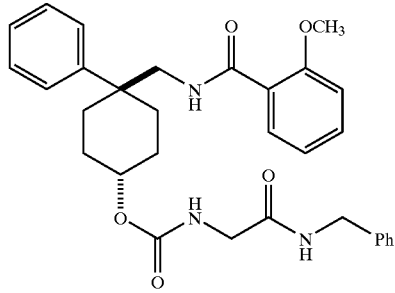

The title compound was prepared as described in Example 225 using benzylamine. After standard workup, the crude product was purified by trituration in EtOAc.

$^1$H NMR (CDCl$_3$) δ 1.48 (m, 2H), 1.74 (m, 2H), 1.93 (m, 2H), 2.3 (m, 2H), 3.63 (m, 6H), 3.84 (m, 2H), 4.44 (m, 2H), 4.77 (m, 1H), 5.16 (m, 1H), 6.88 (d, 1H), 7.06 (t, 1H), 7.28 (m, 5H), 7.44 (m, 5H), 7.58 (m, 1H), 8.2 (dd, 1H); Mass Spectrum (PB-NH3/CI): m/e 480 (M+1).

EXAMPLE 225 trans 1-(N-(N,N-Dimethylaminocarbonylmethyl)carbamoyloxy)-4-phenyl-4-(3-(2-methoxyphenyl)-3-oxo-2-azapropyl)cyclohexane

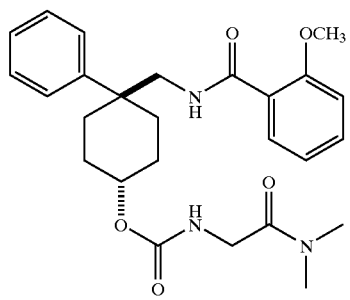

The title compound was prepared as described in Example 225 using N,N,-dimethylamine.

$^1$H NMR (CDCl$_3$) δ 1.5 (m, 2H), 1.74 (m, 2H), 1.95 (m, 2H), 2.32 (m, 2H), 2.95 (ds, 6H), 3.62 (s, 3H), 3.64 (m, 3H) 3.95 (m, 2H), 4.78 (m, 1H), 6.87 (d, 1H), 7.04 (t, 1H), 7.3 (m, 1H), 7.44 (m, 4H), 7.58 (m, 1H), 8.2 (dd, 1H); Mass Spectrum (PB-NH3/CI): m/e 468 (M+1).

EXAMPLE 226 trans 1-(N-(N-Methylaminocarbonylmethyl)carbamoyloxy)-4-phenyl-4-(3-(2-methoxyphenyl)-3-oxo-2-azapropyl)cyclohexane

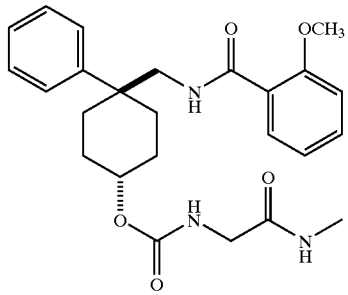

To a solution of 0.05 gm of trans 1-(N-(carboxymethyl)carbamoyloxy)-4-phenyl-4-(3-(2-methoxyphenyl)-3-oxo-2-azapropyl)cyclohexane (Example 223, 0.11 mmol) in 1 mL of $CH_2Cl_2$ was added 0.023 gm) carbonyldiimidazole (0.14 mmol). After stirring for 1 hr at rt, methylamine gas was bubbled into the reaction mixture for 5 min. After 1 hr, the reaction mixture was diluted with 2N HCl solution. The mixture was extracted with ether and the combined organic fractions were washed with brine, dried over $Na_2SO_4$, filtered and the filtrate was concentrated. The residue was purified by chromatography (HPLC NOVA RCM, 80% to 100% gradient of t-butylmethylether:$CH_3CN$, 3:1 in hexanes) to give the title compound.

$^1$H NMR (CDCl$_3$) δ 1.52 (m, 2H), 1.74 (m, 2H), 1.95 (m, 2H), 2.32 (m, 2H), 2.1 (br s, 3H), 3.62 (s, 3H), 3.64 (m, 3H) 3.8 (m, 2H), 4.79 (m, 1H), 5.16 (m, 1H), 6.88 (d, 1H), 7.05 (t, 1H), 7.3 (m, 1H), 7.44 (m, 4H), 7.59 (m, 1H), 8.2 (dd, 1H); Mass Spectrum (PB-NH3/CI): m/e 454 (M+1).

The compounds in Tables 1, 2 and 3 below were also made using the protocols described in the schemes and examples above. The third row lists the source of the carboxylic acid that was coupled with the amine to yield the corresponding amide.

TABLE 1

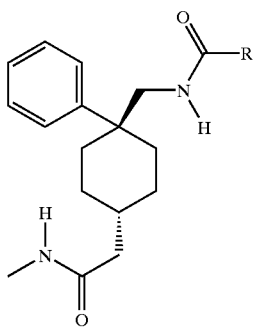

| R | Physical Data | Source of Carboxylic Acid |
|---|---|---|
| ![structure] | 79–81 ° C. | Commercially available |
| ![structure] | 125–127° C. | Commercially available |

TABLE 1-continued

| R | Physical Data | Source of Carboxylic Acid |
|---|---|---|
| 3'-chlorobiphenyl-3-yl | (300 MHz, CDCl3)d7.74(s, 1H), 7.68–7.62(m, 1H), 7.57–7.31(m, 11H), 5.71–5.69(m, 1H), 4.78–4.75(m, 1H), 4.43–4.40(m, 1H), 3.57(d, J=6.41Hz, 2H), 2.74(d, J=4.58Hz, 2H), 2.65(bs, 1H), 2.38–2.34(m, 2H), 1.97–1.93(m, 2H), 1.81–1.72(m, 2H), 1.51–1.44(m, 2H). | Prepared analogously to 3'-methylbiphenyl-3-carboxylic acid described in J. Med. Chem. (1996), 39(1), 217–23 |
| 4'-chlorobiphenyl-3-yl | (300 MHz, CDCl3)d7.79(s, 1H), 7.66–7.62(m, 1H), 7.50–7.41(m, 10H), 7.34–7.31(m, 1H), 5.75–5.71(m, 1H), 4.77–4.74(m, 1H), 4.43–4.39(m, 1H), 3.56(d, J=6.10Hz, 2H), 2.74(d, J=4.89Hz, 2H), 2.63(bs, 1H), 2.37–2.33(m, 2H), 1.97–1.92(m, 2H), 1.80–1.71(m, 2H), 1.50–1.43(m, 2H). | Prepared analogously to 3'-methylbiphenyl-3-carboxylic acid described in J. Med. Chem. (1996), 39(1), 217–23 |
| 3'-methylbiphenyl-3-yl | (300 MHz, CDCl3)d7.79(s, 1H), 7.68(d, J=6.10Hz, 1H), 7.50–7.18(m, 11H), 5.74–5.70(m, 1H), 4.78–4.72(m, 1H), 4.44–4.40(m, 1H), 3.57(d, J=6.41Hz, 2H), 2.74(d, J=4.58Hz, 2H), 2.65(bs, 1H), 2.44(s, 3H), 2.38–2.33(m, 2H), 1.98–1.94(m, 2H), 1.80–1.71(m, 2H), 1.50–1.43(m, 2H). | J. Med. Chem. (1996), 39(1), 217–23 |
| 4'-methylbiphenyl-3-yl | (300 MHz, CDCl3)d7.78(s, 1H), 7.67(d, J=6.10Hz, 1H), 7.50–7.39(m, 7H), 7.31–7.25(m, 4H), 5.74–5.70(m, 1H), 4.79–4.73(m, 1H), 4.45–4.43(m, 1H), 3.56(d, J=6.11Hz, 2H), 2.74(d, J=4.78Hz, 2H), 2.65(bs, 1H), 2.41(s, 3H), 2.35(bd, J=10.38Hz, 2H), 1.97–1.90(m, 2H), 1.80–1.70(m, 2H), 1.50–1.43(m, 2H). | Prepared analogously to 3'-methylbiphenyl-3-carboxylic acid described in J. Med. Chem. (1996), 39(1), 217–23 |

TABLE 1-continued
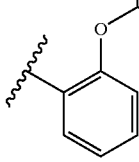
| R | Physical Data | Source of Carboxylic Acid |
|---|---|---|
| 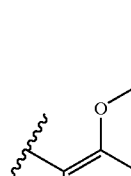 | 129–131 °C. | Synth. Commun. (1995), 25(7), 1077–83. |
| 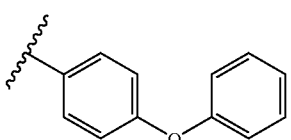 | 119–122° C. | Prepared analogously to 2-(3-chlorophenyloxy)benzoic acid described in Synth. Commun. (1995), 25(7), 1077–83. |
| 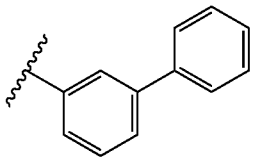 | 187–189 °C. | Commercially available |
| 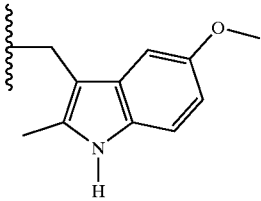 | 83–86° C. | Chem. Pharm. Bull. (1997), 45(11), 1870–1874. |
| 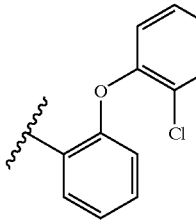 | 105–107 °C. | Commercially available |
|  | 151–153° C. | J. Org. Chem. (1972), 37(25), 4022–6. |

TABLE 1-continued
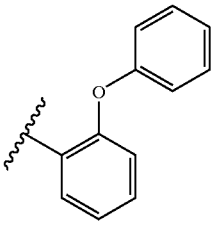
| R | Physical Data | Source of Carboxylic Acid |
|---|---|---|
| 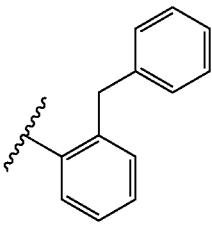 | 178.5–180.5 °C. | Commercially available |
| 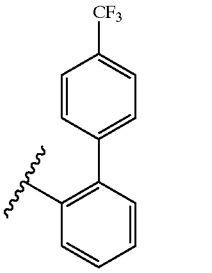 | 147–149 °C. | Commercially available |
| 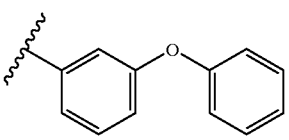 | 188–190 °C. | Commercially available |
| 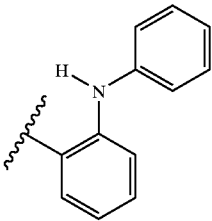 | 173–175 °C. | Commercially available |
| | MS (FAB+) 458 | Commercially available |

TABLE 2

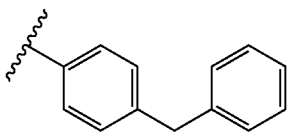

| R | Physical Data | Source of Carboxylic Acid |
|---|---|---|
| 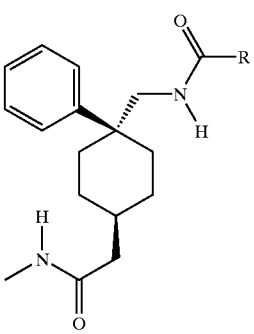 | M.p. 184.5–185.5 °C. | Commercially available |
| 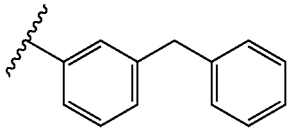 | 83.5–85 °C. | Acta Chem. Scand. (1995), 49(8), 599–608 |
| 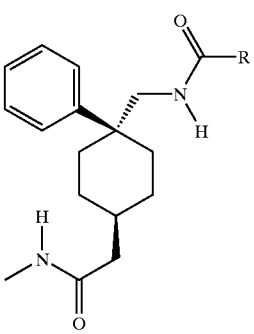 | $^1$H NMR(300 MHz, CDCl$_3$)d: 7.66–7.26(m, 14H, Ar); 5.75(s, 1H, NH); 4.76(brs, 1H, OCHCH$_2$); 4.49(s, 1H, NH); 3.56(d, J=5.8Hz, 2H, CCH$_2$NH); 2.74(d, J=4.6Hz, 3H, CH$_3$NH); 2.35(d, J=12.5Hz, 2H, CH$_2$); 1.95(d, J=7.63Hz, 2H, CH$_2$); 1.75(t, J=12.0Hz, 2H, CH$_2$); 1.45(q, J=10.1Hz, 2H, CH$_2$). | Commercially available |
| 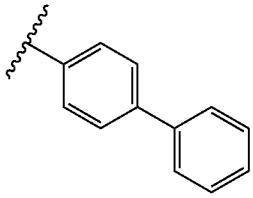 | $^1$H NMR(300 MHz, CDCl$_3$)d: 8.16(d, J=4.9Hz, 1H, Pyr); 7.72(t, J=8.6Hz, 1H, Pyr); 7.42–7.22(m, 9H, Ar); 7.02(t, J=6.4Hz, 1H, Ar); 6.94(d, J=8.2Hz, 1H, Ar); 5.69(t, J=5.8Hz, 1H, NH); 4.74(brs, 1H, OCHCH$_2$); 4.48(s, 1H, NH); 3.52(d, J=6.1Hz, 2H, CCH$_2$NH); 2.72(d, J=4.6Hz, 3H, CH$_3$NH); 2.22(d, J=14.0Hz, 2H, CH$_2$); 1.93(d, J=9.2Hz, 2H, CH$_2$); 1.72(t, J=8.8Hz, 2H, CH$_2$); 1.42(q, J=10.2Hz, 2H, CH$_2$). | Commercially available |

TABLE 3

| Compound | Physical Data | Source of Carboxylic Acid |
|---|---|---|
| 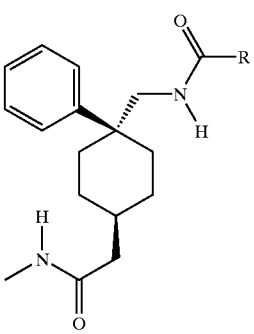 | 99–101° C. | Commercially available |

What is claimed is:

1. A compound of structural Formula I:

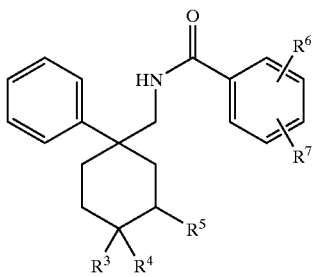

or a pharmaceutically acceptable salt, crystal form, or hydrate, wherein:

n is: 0, 1, 2 or 3;
r is: 0 or 1;
s is: 0 or 1;
$R^6$ and $R^7$ are independently:
  (1) halo, wherein halo is fluoro, chloro, bromo, or iodo,
  (2) hydroxy,
  (3) $O[(C=O)O_r]_s(C_1-C_6)$-alkyl,
  (4) $-(O)_r(C_0-C_6)$-alkyl-aryl, wherein aryl is phenyl or naphthyl unsubstituted or substituted with up to three substitutents selected from $(C_1-C_3)$alkyl, trifluoromethyl, and halo;
  (5) $NR^8R^9$,
  (6) hydrogen, or
  (7) $R^6$ and $R^7$ can an be taken together when on adjacent carbons to form a fused benzo, dihydrofuranyl, furanyl, pyrrolidyl, dihydropyrrolidyl or 1,3-dioxolan group;
$R^3$ and $R^4$ are independently:
  (1) halo, wherein halo is fluoro, chloro, bromo, or iodo,
  (2) hydroxy,
  (3) cyano,
  (4) $CO_2(C_1-C_6)$-alkyl,
  (5) $NR^8R^9$,
  (6) $O(CO)NR^8R^9$,
  (7) $NR^8(CO)NR^8R^9$,
  (8) hydrogen,
  (9) $(C_1-C_{10})$-alkyl, wherein alkyl includes cyclic as well as acyclic groups and is unsubstituted or substituted with one or two of the substituents selected from the group consisting of:
    (a) halo, wherein halo is fluoro, chloro, bromo, or iodo,
    (b) hydroxy,
    (c) $O[(C=O)O_r]_s(C_1-C_6)$-alkyl,
    (d) aryl-$(C_1-C_6)$-alkyloxy,
    (e) $O(CO)NR^8R^9$,
    (f) CHO,
    (g) $CO_2H$,
    (h) $CO_2(C_1-C_6)$-alkyl, and
    (i) $CONR^8R^9$,
  (10) $O[(C=O)O_r]_s(C_1-C_6)$-alkyl, alkyl as defined above,
  (11) $O[(C=O)O_r]_s(C_2-C_6)$-alkenyl, as defined above,
  (12) $O[(C=O)O_r]_s$aryl, aryl as defined above,
  (13) $O[(C=O)O_r]_s$heteroaryl, heteroaryl as defined above, or
  (14) $O(CO)NH(CH_2-CO-NR^8R^9)$;
$R^3$ can also be any of the following when $R^4$ is absent:
  (15) oxo,
  (16) $=CH_2$, or
$R^3$ and $R^4$ can be taken together to form a spiro-fused heterocyclyl group, wherein heterocyclyl is as defined above, or
$R^3$ and $R^5$ can be taken together to form a fused oxirane;
$R^5$ is:
  (1) hydrogen,
  (2) halogen,
  (3) $(C_2-C_6)$-alkenyl,
  (4) hydroxy,
  (5) $O(CO)NR^8R^9$,
  (6) oxo, or
$R^5$ and $R^3$ can be taken together to form a fused oxirane; and
$R^8$ and $R^9$ are independently selected from the group consisting of:
  (1) hydrogen,
  (2) $[(C=O)O_r]_s$aryl, wherein aryl is as defined above,
  (3) $[(C=O)O_r]_s(C_2-C_8)$-alkenyl, wherein alkenyl is as defined above,
  (4) $[(C=O)O_r]_s(C_1-C_8)$-alkyl, wherein alkyl is as defined above,
  (5) $(C=O)_rS(O)_n(C_1-C_8)$-alkyl, wherein alkyl is as defined above,
  (6) $(C=O)_rS(O)_n$aryl, wherein aryl is as defined above, and
  (7) heterocyclyl, wherein heterocyclyl is defined above.

2. The compound of structural formula I

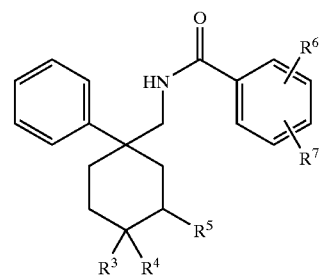

wherein:

$R^6$ and $R^7$ are independently:
  (1) halo, wherein halo is fluoro, chloro, bromo, or iodo,
  (2) hydroxy,
  (3) $(C_1-C_6)$-alkyloxy, wherein the alkyl is cyclic or straight-chained,
  (4) acetoxy,
  (5) $NR^8R^9$,
  (6) $-(O)_r(C_0-C_3)$-aryl, wherein aryl is phenyl or naphthyl unsubstituted or substituted with up to three substitutents selected from $(C_1-C_3)$alkyl, trifluoromethyl, and halo,
  (7) hydrogen, or
  (8) $R^6$ and $R^7$ can an be taken together to form a fused benzo, dihydrofuranyl, furanyl, pyrrolidyl, dihydropyrrolidyl or 1,3-dioxolan group;
$R^3$ and $R^4$ are independently:
  (1) halo, wherein halo is fluoro, chloro, bromo, or iodo,
  (2) hydroxy,
  (3) $(C=O)O(C_1-C_6)$-alkyl,
  (4) $CH_2CO_2-(C_1-C_6)$-alkyl,
  (5) cyano,
  (6) benzyloxy,
  (7) $CH_2OAc$,
  (8) OAc, (9) $(C_1-C_6)$-alkyl, wherein alkyl can be unsubstituted or substituted with bromide
(10) $NR^8R^9$,
(11) $O(CO)NR^8R^9$,
(12) $NR^8(CO)NR^8R^9$,
(13) hydrogen,
(14) $CH_2OH$,
(15) $CH_2O(C=O)$phenyl, wherein phenyl is unsubstituted or monosubstituted with methoxy,
(16) $O(C=O)$-phenyl, wherein phenyl is unsubstituted or monosubstituted with bromide,
(17) $O(C=O)O$-phenyl, wherein phenyl is unsubstituted or monosubstituted with nitro,
(18) $CH_2(CO)NR^8R^9$,
(19) $O(C=O)O-(C_2-C_6)$-alkenyl,
(20) $O(C=O)-(C_1-C_3)$-alkyl, wherein the alkyl can be unsubstituted or substituted with bromide or $-CO_2CH_3$,
(21) $O(C_1-C_6)$-alkyl, wherein alkyl can be unsubstituted or substituted with phenyl,
(22) $O(C=O)O-(C_1-C_6)$-alkyl,
(23) $CH_2O(CO)NR^8R^9$, or
(24) $CH_2(C=O)O-(C_1-C_6)$-alkyl, $R^3$ can also be any of the following when $R^4$ is absent:
(25) oxo,
(26) $=CH_2$,
(27) $=CH-CO_2-(C_1-C_6)$-alkyl,
(28) $=CH-(CO)-NR^8R^9$, or
(29) $=CH-CO_2H$, or $R^3$ and $R^4$ can be taken together to form a spiro-fused heterocyclyl group, wherein heterocyclyl is defined as:
(30) oxirane,
(31) 1,3-dioxolan,
(32) 2,2-dimethyl-1,3-dioxolan, or
(33) glycol sulfite, or $R^3$ and $R^5$ can be taken together to form a fused oxirane;
$R^5$ is:
(1) hydrogen,
(2) halogen,
(3) $(C_2-C_6)$-alkenyl,
(4) hydroxy,
(5) $O(CO)NR^8R^9$,
(6) oxo, or $R^5$ and $R^3$ can be taken together to form a fused oxirane;
$R^8$ and $R^9$ are independently selected from the group consisting of:
(1) hydrogen,
(2) $(C=O)O(C_1-C_6)$-alkyl, wherein alkyl is optionally substituted with phenyl or methoxy,
(3) $(C=O)$phenyl, wherein phenyl is optionally substituted with bromide or methoxy,
(4) $(C_1-C_6)$-alkyl, wherein alkyl is optionally substituted with phenyl, methoxy, hydroxy, $OCH_2OCH_3$, benzyl$SO_3$, phenyl$SO_3$, or carboxymethyl,
(5) $(C_2-C_6)$-alkenyl,
(6) $(C=O)O$-phenyl, wherein phenyl is optionally substituted with nitro,
(7) $(C=O)O(C_2-C_6)$-alkenyl,
(8) $(C=O)(C_1-C_3)$-alkyl, wherein alkyl is optionally substituted with phenyl,
(9) $(C=O)(C_2-C_4)$-alkenyl,
(10) phenyl,
(11) $SO_2$-phenyl,
(12) $SO_2$-benzyl,
(13) $CH_2(CO)CH_3$,
(14) $CH_2(CO)NH$-benzyl,
(15) $CH_2(CO)NH$-allyl,
(16) $CH_2(CO)N(CH_3)_2$,
(17) $CH_2(CO)NH(CH_3)$,

(18) 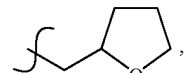

(19) 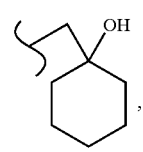

(20) 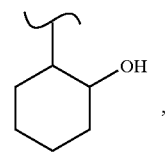

(21) 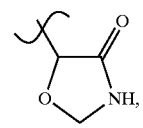

(22) 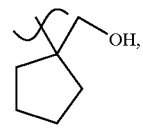

(23) 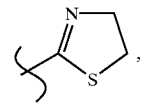

(24) $CH_2CH_2NHCO_2(C_1-C_3)$alkyl,
(25) $CH_2CH_2O(CO)NHCH_3$,
(26) $CH_2CH_2O(CO)NH$-allyl,
(27) $CH_2CH_2NH(SO_2)CH_3$,
(28) $CH_2CH_2NH_2$,
(29) $CH_2CH_2NH(CO)CH_2CH_3$, and
(30) benzyl.

3. A compound selected from the group consisting of:

trans 1-(N-ethylcarbamoyloxy)-4-phenyl-4-(3-(2-methoxyphenyl)-3-oxo-2-azaprop-1yl)cyclohexane, trans 1-(N-allylcarbamoyloxy)-4-phenyl-4-(3-(2-hydroxy-5-fluorophenyl)-3-oxo-2-azaprop-1-yl)cyclohexane, trans 1-(N-n-propylcarbamoyloxy)-4-phenyl-4-(3-(2-methoxyphenyl)-3-oxo-2-azaprop-1-yl)cyclohexane, trans 1-(N-methylcarbamoyloxy)-4-phenyl-4-(3-(2-methoxyphenyl)-3-oxo-2-azaprop-1-yl)cyclohexane, and trans 1-(N-allylcarbamoyloxy)-4-phenyl-4-(3-(2-methoxyphenyl)-3-oxo-2-azapropyl)cyclohexane, or a pharmaceutically acceptable salt thereof.

4. The compound of claim 2 with the following structural formula:

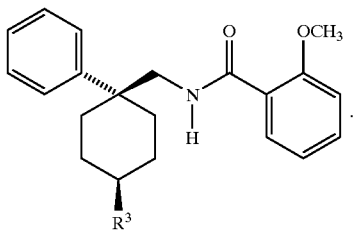

5. The compound of claim 2 with the following structural formula:

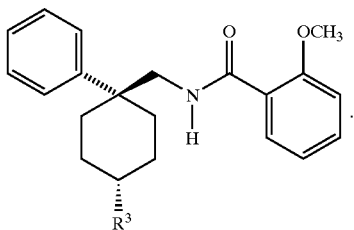

6. The compound of claim 2 with the following structural formula:

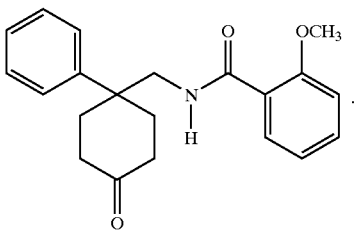

7. A method of treating a condition in a mammal, the treatment of which is effected or facilitated by $K_v1.3$ inhibition, which comprises administering a $K_v1.3$ inhibiting amount of the compound of claim 1.

8. The method of treating a condition in a mammal the treatment of which is effected or facilitated by $K_v1.3$ inhibition, as recited in claim 7, wherein the condition is selected from the group consisting of: resistance by transplantation of organs or tissue, graft-versus-host diseases brought about by medulla ossium transplantation, rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scieroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy, disease caused by histamine or leukotriene-$C_4$ release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augention of chemotherapeutic effect, cytomegalovirus infection, HCMV infection, AIDS, cancer, senile dementia, trauma, and chronic bacterial infection.

9. The method as recited in claim 7, wherein the condition is an autoimmune disease.

10. A method of preventing or treating resistance to transplantation or transplantation rejection of organs or tissues in a patient in need thereof, which comprises administering a therapeutically effective amount of the compound in claim 1.

11. A method of suppressing the immune system in a subject in need thereof, which comprises administering an immune suppressing amount of the compound in claim 1.

12. A pharmaceutical formulation comprising a pharmaceutically acceptable carrier and the compound of Formula I, as recited in claim 1 or a pharmaceutically acceptable crystal form or hydrate thereof.

13. A pharmaceutical composition made by combining the compound of claim 1 and a pharmaceutically acceptable carrier.

14. The pharmaceutical formulation of claim 12, comprising in addition, a second immunosuppressive agent.

15. A pharmaceutical composition made by combining the compound of claim 1, a pharmaceutically acceptable carrier, and a second immunosuppressive agent.

16. The pharmaceutical formulation as recited in claim 14 wherein the second immunosuppressive agent is selected from a group consisting of azathioprine, brequinar sodium, deoxyspergualin, mizaribine, mycophenolic acid morpholino ester, cyclosporin, FK-506 and rapamycin.

17. The method of claim 11, comprising the coadministration of a second immunosuppressive agent.

18. A method of preventing or treating resistance by transplantation of organs or tissue, graft-versus-host diseases brought about by medulla ossium transplantation, rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma and dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy, disease caused by histamine or leukotriene-$C_4$ release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augention of chemotherapeutic effect cytomegalovirus infection, HCMV infection, AIDS, cancer, senile dementia, trauma, and chronic bacterial infection which comprises administering the compound of claim 1.

19. A method of treating a condition in a mammal, the treatment of which is effected or facilitated by $K_v1.3$ inhibition, which comprises administering a pharmaceutical formulation comprising a pharmaceutical carrier and the compound in claim 1, in an amount that is effective at inhibiting $K_v1.3$.

20. A method of treating a condition in a mammal, the treatment of which is effected or facilitated by $K_v1.3$ inhibition, comprising coadministering a therapeutically effective amount of the compound in claim 1, with a second immunosuppressive agent.

21. A method of treating a condition in a mammal, the treatment of which is effected or facilitated by $K_v1.5$ inhibition, which comprises administering a compound of claim 1 in an amount that is effective at inhibiting $K_v1.5$.

22. A method of treating a condition in a mammal, the treatment of which is effected or facilitated by $K_v1.5$ inhibition, which comprises administering a pharmaceutical formulation comprising a pharmaceutical carrier and a compound of claim 1, in an amount that is effective at inhibiting $K_v1.5$.

23. A method of preventing or treating cardiac arrhythmias in a mammal, which comprises administering a therapeutically effective amount of a compound of claim 1.

* * * * *